Figure 2:
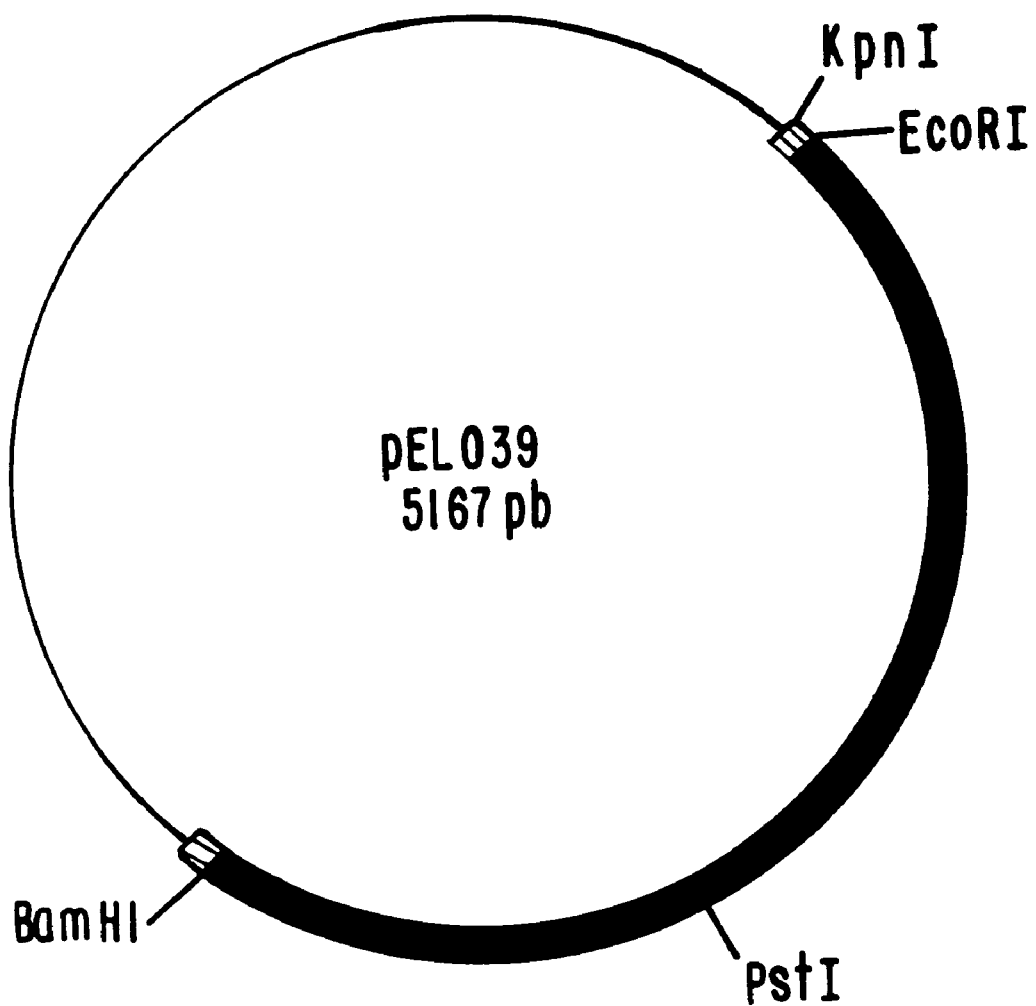

United States Patent [19]
Audonnet et al.

[11] Patent Number: 5,980,906
[45] Date of Patent: Nov. 9, 1999

[54] LIVE RECOMBINANT AVIAN VACCINE USING AN AVIAN HERPESVIRUS AS VECTOR

[75] Inventors: Jean-Christophe Francis Audonnet, Lyons; Michel Joseph Marie Bublot, St-Genis-les-Ollieres; Raphaël Jean Darteil; Carole Véronique Duinat, both of Lyons; Eliane Louise Françoise Laplace, Oullins; Michel Albert Emile Riviere, Ecully, all of France

[73] Assignee: Rhone Merieux, Lyons, France

[21] Appl. No.: 08/578,096

[22] Filed: Dec. 26, 1995

[30] Foreign Application Priority Data

Dec. 30, 1994 [FR] France ................... 94 16017

[51] Int. Cl.[6] .................... C12N 7/01; A39K 39/245; A39K 39/295
[52] U.S. Cl. ..................... 424/199.1; 424/204.1; 424/229.1; 435/235.1; 435/320.1; 435/69.1; 435/69.3; 435/71.1
[58] Field of Search .............. 424/184.1, 199.1, 424/204.1, 186.1, 229.1; 435/69.1, 69.3, 71.1, 235.1, 320.1; 530/403; 536/23.72

[56] References Cited

FOREIGN PATENT DOCUMENTS

90/02802  3/1990  WIPO ............... C12N 15/38

OTHER PUBLICATIONS

Nash et al. "the UL55 and Ul56 genes of herpes simplex virus type 1 are not required for viral replication, intraperitoneal virulence or establishment of latency in mice". Virology, vol. 204, pp. 794–798, 1994.

Marshall et al. "plasmid associated effects on test gene expression and marek's disease virus plaque formation during recombination trials". Journal of Virological Methods. vol. 40, pp. 195–204, 1992.

Jagadish et al. "birnavbirus precusor polyprotein is processed in *E coli* by its own virus encoded polypeptide". Journal of Virology. vol. 62, No. 3, pp. 1048–1087, Mar. 1988.

Bradley et al. "loss of Marek's disease virus tumorgenicity is associated with the truncation od RNAs transcribed with BamHI–H". Journal of Virology. vol. 63, No. 10, pp. 4129–4135, Oct. 1989.

Isfort et al. "integration of multiple chicken retroviruses into multiple chicken herpesviruses: herpesviral gD as a common target of intergration". Virology. vol. 203, pp. 125–133, 1994.

Buckmaster et al. "gene sequence and mapping data from Marek's disease virus Herpesvirus of turkey: implications for herpesvirus classification". Journal General Virology. vol. 69, pp. 2033–2042, 1988.

Harty et al. "transcriptional and translational analysis of the UL2 gene of equine herpesvirus 1: a homolog of UL55 of herpes simplex virus type 1 that is maintained in the genome of defective interfering particles". Journal of Virology. vol. 67, No. 4, p, Apr. 1993.

Igarashi et al. "restriction enzyme map of herpesvirus of turkey DNA and its collinear relationship with Marek's disease virus DNA". Virology. vol. 157, pp. 351–358, 1987.

Sinclair et al. "charaterization of a herpes simplex virus type 1 deletion variant (1703) which under–produces vmw63 during immediate early conditions of infection". Journal General Virology. vol. 75, pp. 1083–1089, 1994.

*Primary Examiner*—Mary E. Mosher
*Assistant Examiner*—Datquan Lee
*Attorney, Agent, or Firm*—Fromer Lawrence & Haug LLP; William S Frommer; Thomas J Kowalski

[57] ABSTRACT

The live recombinant avian vaccine comprises, as vector, an avian herpesvirus comprising at least one nucleotide sequence coding for and expressing an antigenic polypeptide of an avian pathogenic agent, inserted into the region lying between the ATG of ORF UL55 and the junction of $U_L$ with the adjacent repeat region, under the control of the CMV immediate early promoter. The vector is preferably chosen from the group consisting of Marek's disease viruses (MDV and HVT), infectious laryngotracheitis virus ILTV and herpes of ducks. A polyvalent vaccine formula comprises at least two vaccines of this type, with different inserted sequences.

29 Claims, 39 Drawing Sheets

FIG. 1A

```
   1 GGATCCATCAGCAATGCGGGCTGTAGTCCCGATTCCCGTTTCAAATGAAGGTGCTCCAAC
 159◄    AspMetLeuLeuAlaProGlnLeuGlySerGluArgLysLeuHisLeuHisGluLeuV
  61 ACGGTCTTCAAAGCAACCGGCATACCAGCAAACACAGACTGCAACTCCCCGCTGCAATGA
 139◄alThrLysLeuAlaValProMetGlyAlaPheValSerGlnLeuGluGlySerCysHisA
 121 TTGGTTATAAACAGTAATCTGTCTTCTGGAAGTATATTTCGCCCGACAATCCACGGCGCC
 119◄snThrIlePheLeuLeuArgAspGluProLeuIleAsnArgGlyValIleTrpProAlaG
 181 CCCAAAGTTAAAAACCATCCATGTGTATTTGCGTCTTCTCTGTTAAAAGAATATTGACTG
  99◄lyLeuThrLeuPheTrpGlyHisThrAsnAlaAspGluArgAsnPheSerTyrGlnSerA
 241 GCATTTTCCCGTTGACCGCCAGATATCCAAAGTACAGCACGATGTTGCACGGACGACTTT
  79◄laAsnGluArgGlnGlyGlySerIleTrpLeuValAlaArgHisGlnValSerSerLysA
 301 GCAGTCACCAGCCTTCCTTTCCACCCCCCACCAACAAAATGTTTATCGTAGGACCCATA
  59◄laThrValLeuArgGlyLysTrpGlyGlyValLeuLeuIleAsnIleThrProGlyMetA
 361 TCCGTAATAAGGATGGGTCTGGCAGCAACCCCATAGGCGCCTCGGCGTGGTAGTTCTCGA
  39◄spThrIleLeuIleProArgAlaAlaValGlyTyrAlaGlyArgArgProLeuGluArgP
 421 GGATACATCCAAAGAGGTTGAGTATTCTCTCTACACTTCTTGTTAAATGGAAAGTGCATT
  19◄roTyrMetTrpLeuProGlnThrAsnGluArgCysLysLysAsnPheProPheHisMet
 481 TGCTTGTTCTTACAATCGGCCCGAGTCTCGTTCACAGCGCCTCGTTCACACTTAAACCAC
 541 AAATAGTCTACAGGCTATATGGGAGCCAGACTGAAACTCACATATGACTAATATTCGGGG
 601 GTGTTAGTCACGTGTAGCCCATTGTGTGCATATAACGATGTTGGACGCGTCCTTATTCGC
 661 GGTGTACTTGATACTATGGCAGCGAGCATGGGATATTCATCCTCGTCATCGTTAACATCT
               1►MetAlaAlaSerMetGlyTyrSerSerSerSerSerLeuThrSer
 721 CTACGGGTTCAGAATGTTTGGCATGTCGTCGATCCTTTGCCCATCGTTGCAAATTACAAG
  16►LeuArgValGlnAsnValTrpHisValValAspProLeuProIleValAlaAsnTyrLys
 781 TCCGATCGCCATGACCGCGATAAGCCTGTACCATGTGGCATTAGGGTGACATCTCGATCA
  36►SerAspArgHisAspArgAspLysProValProCysGlyIleArgValThrSerArgSer
 841 TACATTATAAGACCAACGTGCGAGTCTTCCAAAGACCTGCACGCCTTCTTCTTCGGATTG
  56►TyrIleIleArgProThrCysGluSerSerLysAspLeuHisAlaPhePhePheGlyLeu
 901 TCAACGGGTTCTTCAGAATCTATGCCCATATCTGGCGTTGAGACCATTGTGCGTTTAATG
  76►SerThrGlySerSerGluSerMetProIleSerGlyValGluThrIleValArgLeuMet
 961 AACAATAAAGCGGCATGCCATGGAAAGGAGGGCTGCAGATCTCCATTTTCTCACGCCACT
  96►AsnAsnLysAlaAlaCysHisGlyLysGluGlyCysArgSerProPheSerHisAlaThr
1021 ATCCTGGACGCTGTAGACGATAATTATACCATGAATATAGAGGGGGTATGTTTCCACTGC
 116►IleLeuAspAlaValAspAspAsnTyrThrMetAsnIleGluGlyValCysPheHisCys
1081 CACTGTGATGATAAGTTTTCTCCAGATTGTTGGATATCTGCATTTTCTGCTGCCGAACAA
 136►HisCysAspAspLysPheSerProAspCysTrpIleSerAlaPheSerAlaAlaGluGln
1141 ACTTCATCGCTATGCAAAGAGATGCGTGTGTACACGCNGCCGTTGAGTATACGGGAAACT
 156►ThrSerSerLeuCysLysGluMetArgValTyrThr???ProLeuSerIleArgGluThr
1201 AAATGTTCATAGAGGTCTTTGGCTATATGTTATTAAATAAAATAATTGACCAGTGAACA
 176►LysCysSer
1261 ATTTGTTTAATGTTAGTTTATTCAATGCATTGGTTGCAAATATTCATTACTTCTCCAATG
1321 CCAGGTCATTCTTTAGCGAGTGATGTTATGACATTGCTGTGAAAATTACTACAGGATATA
1381 TTTTTAAGATGCAGGAGTAACAATGTGCATAGTAGGCGTAGTTATCGCAGACGTGCAACG
         185◄SerAlaProThrValIleHisMetThrProThrThrIleAlaSerThrCysArg
             1►MetCysIleValGlyValValIleAlaAspValGlnAr
1441 CTTCGCATTTGAGTTACCGAAGTGCCCAACAGTGCTGCGGTTATGGTTTATGCGCACAGA
 167◄LysAlaAsnSerAsnGlyPheHisGlyValThrSerArgAsnHisAsnIleArgValSer
  13►gPheAlaPheGluLeuProLysCysProThrValLeuArgLeuTrpPheMetArgThrGl
1501 ATCCATGCATGTCCTAATTGAACCATCCGATTTTTCTTTTAATCGCGATCGTTGTTTGGG
 147◄AspMetCysThrArgIleSerGlyAspSerLysGluLysLeuArgSerArgGlnLysPro
  33►uSerMetHisValLeuIleGluProSerAspPheSerPheAsnArgAspArgCysLeuGl
1561 CAACTGCGTTATTTCAGATCTAAAAATTTACCCTTTATGACCATCACATCTCTCTGGCT
 127◄LeuGlnThrIleGluSerArgPhePheLysGlyLysIleValMetValAspArgGlnSer
  53►yAsnCysValIleSerAspLeuLysAsnLeuProPheMetThrIleThrSerLeuTrpLe
```

FIG. 1B

```
1621 CATACCCGCTTGGATAAGATATCATGTAGATTCCGCCCTAAGAAATGCAAACTAACATT
 107◄MetGlyArgLysSerLeuIleAspHisLeuAsnArgGlyLeuPheHisLeuSerValAsn
  73►uIleProArgLeuAspLysIleSerCysArgPheArgProLysLysCysLysLeuThrLe
1681 ATTGTCGGTTCCATATACACTTCCATCTTGTCCTTCGAAAATAACAAACTCGCGCAATAG
  87◄AsnAspThrGlyTyrValSerGlyAspGlnGlyGluPheIleValPheGluArgLeuLeu
  93►uLeuSerValProTyrThrLeuProSerCysProSerLysIleThrAsnSerArgAsnAr
1741 ACCGTCCGTACATGCATGGCCGATGTGTGTCAACATCATTGGTCTGCTAGATCCCGATGG
  67◄GlyAspThrCysAlaHisGlyIleHisThrLeuMetMetProArgSerSerGlySerPro
 113►gProSerValHisAlaTrpProMetCysValAsnIleIleGlyLeuLeuAspProAspGl
1801 GACGAATCGTACAGTCGTCGCTCCAGCATTGGCAAAAATCCCCAGATACCCTCCATGCGG
  47◄ValPheArgValThrThrAlaGlyAlaAsnAlaPheIleGlyLeuTyrGlyGlyHisPro
 133►yThrAsnArgThrValValAlaProAlaLeuAlaLysIleProArgTyrProProCysGl
1861 CAAATCTAAATTGCGACCCCGAAGAGACTGCACCAAAGTCTTATCGACGCACGCTGATTT
  27◄LeuAspLeuAsnArgGlyArgLeuSerGlnValLeuThrLysAspValCysAlaSerLys
 153►yLysSerLysLeuArgProArgArgAspCysThrLysValLeuSerThrHisAlaAspPh
1921 TTTTGAACAGCGGGAGCCCATTATCTTCAGTGGAGCGTAGACGGGCGAGGCTAATTATGT
   7◄LysSerCysArgSerGlyMet
 173►ePheGluGlnArgGluProIleIlePheSerGlyAla
1981 GACATAGCAACACTGCATGTATGTTTTTATAAATCAATAAGAGTACATAATTTATTACGT
2041 ATCATTTCCGTTTGTAATATACTGTATACATCATCCACACTATTAGTCAGCACTAGCGCG
2101 CGGGCGCACGTTACAATAGCAGCGTGCCCGTTATCTATATTGTCCGATATTTACACATAA
2161 CATTTCATCGACATGATTAAATACCTAAGTACTGCACACAGATGTTTAATGTATATCGTC
2221 ATATAAATTATATCGCTAGGACAGACCCAAACGACCTTTATCCCAAACAGTCAGATCCTC
2281 TTCTCAAGTGTCGATTTCTGTTATGGAATATGCATACCCTGGCCCAGAAATTGCACGCAC
 265◄ThrAspIleGluThrIleSerTyrAlaTyrGlyProGlySerIleAlaArgVal
2341 GAGCGTAGTGAATGCGTCATTGGTTTTACATTTAAAGGCTAAATGCACAAATTCTTTAGA
 247◄LeuThrThrPheAlaAspAsnThrLysCysLysPheAlaLeuHisValPheGluLysSer
2401 CGACAGCACATCGTTAAATAGCATCTCTAGCGTTCTTATGAATGCTAAGCATTGGAGTCC
 227◄SerLeuValAspAsnPheLeuMetGluLeuThrArgIlePheAlaLeuCysGlnLeuGly
2461 TCCTGGTCGGCCACAATAACAGCTGAGTATCATACCCTGAGCTCCGGGGTTGTCGCACAT
 207◄GlyProArgGlyCysTyrCysSerLeuIleMetGlyGlnAlaGlyProAsnAspCysMet
2521 AGCGGATTCGTATAAACATAGGATTTTCCGCGAATCCATCAGTTGCAAAAATCTGTTAGG
 187◄AlaSerGluTyrLeuCysLeuIleLysArgSerAspMetLeuGlnLeuPheArgAsnPro
2581 CTCCATCAACAACGCTGGATTTACTTCAGATCCACGCGTAAAGTAATGGTGCTCGAATAC
 167◄GluMetLeuLeuAlaProAsnValGluSerGlyArgThrPheTyrHisHisGluPheVal
2641 CGTTTTTAGAGTTGTCGGCATTTCAAGGAACAAAGAATTCATTTCTTCATTGCAACGACG
 147◄ThrLysLeuThrThrProMetGluLeuPheLeuSerAsnMetGluGluAsnCysArgArg
2701 CGCCAGAAATCCCAAGACCTCTTTGGGTAGTATGTTCTTGCCTATAAAACACGGCGTTCC
 127◄AlaLeuPheGlyLeuValGluLysProLeuIleAsnLysGlyIlePheCysProThrGly
2761 AAGTGCCAGGAACCACGCATGTGTTACTGTTGGGCGTATTCAGAAATAAAGCGGGGTTT
 107◄LeuAlaLeuPheTrpAlaHisThrValThrProAlaTyrGluSerIlePheArgProLys
2821 ATGCGGCTTTTGAAGCTCGGATATCCAAAGTATCGCTTGCTGATGAACGAGCGATGTAGC
  87◄HisProLysGlnLeuGluSerIleTrpLeuIleAlaGlnGlnHisValLeuSerThrAla
2881 TGTTACAAAACCTCCTTTCCATCCTCCAGTCAACATAATATTTATCGGCCTACCTATGTC
  67◄ThrValPheGlyGlyLysTrpGlyGlyThrLeuMetIleAsnIleProArgGlyIleAsp
2941 CGTAATAAGTATTGGTCGGGCAATTATTCCGTATGAGGTCTTGCAGGAATAAGCTCTTAG
  47◄ThrIleLeuIleProArgAlaIleIleGlyTyrSerThrLysCysSerTyrAlaArgLeu
3001 GGACAGCCAGCTTGGATATGGTGCGAAACAGACCTTCTCGGCTTCAGAATGTCGCTCCGC
  27◄SerLeuTrpSerProTyrProAlaPheCysValLysGluAlaGluSerHisArgGluAla
3061 AGTCTCTTCGTGTCGGTGCATCTTAGATCCACCATCAATGTGTGCAGCATTGACTCCCGC
   7◄ThrGluGluHisArgHisMet
```

FIG. IC

```
3121 CCGTCGAATATTCCTTTTGTTACGATGCAGTAATGAGCACGATCATGGGCGGGGCGATGA
3181 CGTTCTATTTGCATGTCTGCGAACAATTTGCGTCAGTCATACAGCTATGGAGTGGGCCAT
3241 TTCTGGCGTCAACTTAAAAACGCGAACCGCAGACATATGTATTTGCATGCAAAGACGTAT
3301 CTTCGTATTTCTGGGCATCTTCAAATGCTCTGGCCAATATGGCAATGAATTTGGATTCGT
3361 TTGACGCCGATGGTATGCAGTGCAAATGTGCCAATAGCCCACATCCGAAAAAGTTATTTG
3421 TCATACAAGCAGGTGTTAAGTAGCAATCACATAAAGGCACCAGACGCCTCATGGCATCAT
3481 AATGAATAGCTCCTTCTCCCCACTGGAACCACTGACAAAATCTGCGAGTATATTCCGCAA
3541 ACCACATTTTATTTCTCATAGAAACTACCCTAAATCCTTTTAACGGGGAAGAAGAATCCT
                                755◄ IleArgLysValProPhePhePheGlyL
3601 AGATAGTGCTTGAAGTCATGACTGTTACTGCTGCAATAACACTGTATATTATTTATAAAT
 745◄euTyrHisLysPheAspHisSerAsnSerSerCysTyrCysGlnIleAsnAsnIlePheG
3661 TCCGTTTGTCTAGGTATCTGATGTAGGCATTCCGATCCCTTTACTATTGCGTCTTCACGA
 725◄luThrGlnArgProIleGlnHisLeuCysGluSerGlyLysValIleAlaAspGluArgG
3721 CCAAATGGGAATGCGCCAAAATCCCCACACCTCATCACCCTGGAGGCAGATTGTGTATTA
 705◄lyPheProPheAlaGlyPheAspGlyCysArgMetValArgSerAlaSerGlnThrAsnA
3781 TTAATATCCGCCGATTGAAGCACAAAACGGTACGGTACTGTTCCTAATTCTGGTATAGAT
 685◄snIleAspAlaSerGlnLeuValPheArgTyrProValThrGlyLeuGluProIleSerG
3841 TCTATGGTCAAAAGTCTGCATATCCCCGACATTGCCATGAGATCACACAGTCCAAGTAGC
 665◄luIleThrLeuLeuArgCysIleGlySerMetAlaMetLeuAspCysLeuGlyLeuLeuM
3901 ATGTTTATTGAGTCACTCAGACTGTCAACGTCCCTCGCCGCACCACCAATCGAAAATAAA
 645◄etAsnIleSerAspSerLeuSerAspValAspArgAlaAlaGlyGlyIleSerPheLeuT
3961 GTATCTACGCAAGTTATAGCTCCGCATTTTCTATCGCTAGCAGCAATCGCGACGCAAAAC
 625◄hrAspValCysThrIleAlaGlyCysLysArgAspSerAlaAlaIleAlaValCysPheM
4021 ATAAAGGCCATGTTGGGATTTGAACTCTCTGGGGGGCTTGTTATCTTCTGCACCGTCGCA
 605◄etPheAlaMetAsnProAsnSerSerGluProProSerThrIleLysGlnValThrAlaT
4081 GTCGCAGTTTTCCGAAATTTATGTCTAATATATTTTCCGGCCGTGCTCCAATCGGCCGAA
 585◄hrAlaThrLysArgPheLysHisArgIleTyrLysGlyAlaThrSerTrpAspAlaSerP
4141 AAGAATCTGCGTATTACCAGACTCATTGACGGGCCGATAAAGACCATAAAACAAAATTCC
 565◄hePheArgArgIleValLeuSerMetSerProGlyIlePheValMetPheCysPheGluG
4201 TGTGCACTCCCTCCTCCAGTTTTGCCATCGTCCAAGTCCCGTAACTTTTTTGCGTTTCG
 545◄lnAlaSerGlyGlyGlyThrLysGlyAspAspLeuAspArgLeuLysLysGlnThrGluL
4261 AGGAGCAAGCGTTCGTTATCCCTACCCACACTTGTTTTCCACCGTTTTCTTATTATAAGC
 525◄euLeuLeuArgGluAsnAspArgGlyValSerThrLysTrpArgLysArgIleIleLeuP
4321 GGTTGTATCGCCAACGCGTCACCGCAGGTTGTCACATACAGTGATGGCATACTTGAACGT
 505◄roGlnIleAlaLeuAlaAspGlyCysThrThrValTyrLeuSerProMetSerSerArgA
4381 GCAACAACGCGCTCGCTTTGCAAATCTAAGTCATTGACCATCAAATCGCGTTGAGAGGAT
 485◄laValValArgGluSerGlnLeuAspLeuAspAsnValMetLeuAspArgGlnSerSerL
4441 AGCCAGGCATCTTTTTTCCTAGTATGGTGACGGTGCAGCCACCCCAACTCAGTTCTTGTA
 465◄euTrpAlaAspLysLysArgThrHisHisArgHisLeuTrpGlyLeuGluThrArgThrP
4501 AAAAAAGCTATTGGCGGGAATTTATGTTCTGAGGTGCATTCTATATTTATGAGTCCATCA
 445◄hePheAlaIleProProPheLysHisGluSerThrCysGluIleAsnIleLeuGlyAspP
4561 AATGCCATTAACCAGATTCGTATTTTTTCGCTCGACCCGGCATCACTATGGATACAATAC
 425◄heAlaMetLeuTrpIleArgIleLysGluSerSerGlyAlaAspSerHisIleCysTyrA
4621 CTTTCTATGGCCCATTTCAGCTCTCGAACCAACCACACGGACAATTGACTAACATAAGTA
 405◄rgGluIleAlaTrpLysLeuGluArgValLeuTrpValSerLeuGlnSerValTyrThrH
4681 TGATCTTTATCACAGTCGCACCCATCTGAGTTATATTTATGGCATCCGAGCGCTCTTACT
 385◄isAspLysAspCysAspCysGlyAspSerAsnTyrLysHisCysGlyLeuAlaArgValT
4741 GTACGGTCGGATACACCCATGGTTTTTCCTTTATATAGTCGGGTTATAGTCTGTCGGGTT
 365◄hrArgAspSerValGlyMetThrLysGlyLysTyrLeuArgThrIleThrGlnArgThrG
4801 TGGCGGTAGCACGGAGTAGTTTGATTTTAAGAATCGAAAACCGGCTTGGAGAGACCACT
 345◄lnArgTyrCysProThrThrGlnAsnLysLeuIleSerPheArgSerProSerValValT
4861 GTCGAATATTTGTCCGTATACTCTACACGTGAGTGTTGTCCATTCCTAGGTATATTCATC
 325◄hrSerTyrLysAspThrTyrGluValArgSerHisGlnGlyAsnArgProIleAsnMetG
```

FIG. ID

```
4921 TGTTCGGATACCTTCAATTGCTGTTCAGGCATAACCTTAAAGCATATGTTATGTTGTACA
 305◄lnGluSerValLysLeuGlnGlnGluProMetValLysPheCysIleAsnHisGlnValA
4981 TCAAAACTTGGTGAGTTATGTTCGATTGCCGCGCATAAAGAATCGTACATGAGCGTTTCT
 285◄spPheSerProSerAsnHisGluIleAlaAlaCysLeuSerAspTyrMetLeuThrGluA
5041 GCTAACATACTATCTATATTCTCACACGCCCTGCATATACTGTTCCTATTCCAAATTCA
 265◄laLeuMetSerAspIleAsnGluCysAlaGlyAlaTyrValThrGlyIleGlyPheGluA
5101 CGTTTTGCCCCATCGGCTATCTGCTCCCAAAAAGTTGTAATATAGGTGCCGCTGGGTGCG
 245◄rgLysAlaGlyAspAlaIleGlnGluTrpPheThrThrIleTyrThrGlySerProAlaP
5161 AAATTTTCATCAGTTGTATTCCTGATAAACTGAATCACTTTACATAATTTTTGCCACATA
 225◄heAsnGluAspThrThrAsnArgIlePheGlnIleValLysCysLeuLysGlnTrpMetA
5221 TCTGCGTGCAGCCATAGTATCGAACCCGTGGGCTCGGAGACGACAGTGCGTACAATGGGT
 205◄spAlaHisLeuTrpLeuIleSerGlyThrProGluSerValValThrArgValIleProI
5281 ATTTTACCTTTCCCCAACAAAATAATGGTATACAAGTTAGGTCCGTACCTAGACCTTAAT
 185◄leLysGlyLysGlyLeuLeuIleIleThrTyrLeuAsnProGlyTyrArgSerArgLeuT
5341 GTTTCCAATTCTTCTGAATCACTGCACTCTCGTAGGGGAGTAACGGTAATAATTTCGTCT
 165◄hrGluLeuGluGluSerAspSerCysGluArgLeuProThrValThrIleIleGluAspA
5401 CTGAGCCCCGTTTTGCGTTGAAAACTAATCACATTAGATAATGTGCAATCGGTTTCTTTT
 145◄rgLeuGlyThrLysArgGlnPheSerIleValAsnSerLeuThrCysAspThrGluLysI
5461 ATCCGGATACATCTAAGTATTATGACATCGGTGGTCATTGTTTCCATCAACGACCATCTT
 125◄leArgIleCysArgLeuIleIleValAspThrThrMetThrGluMetLeuSerTrpArgL
5521 TTACGATCGCCCATACTACTCATGGACGTTGTCGGTGTTGAAAAATCACCAGAATTGCAA
 105◄ysArgAspGlyMetSerSerMetSerThrThrProThrSerPheAspGlySerAsnCysA
5581 CGGATCTCTGGGTACCATGCTGCTGATGGAATTGGCGGTTTTAATTGTTGTTTCAGTCTA
  85◄rgIleGluProTyrTrpAlaAlaSerProIleProProLysLeuGlnGlnLysLeuArgA
5641 TTATTGCTATCTTTGGCGGGGTTGAATAATGTGGGGGAGAGTGATTGCAGGAATCCGAA
  65◄snAsnSerAspLysAlaProAsnPheLeuThrProProSerHisAsnCysSerAspSerH
5701 TGGGTCAATAAAACGACCGTGCTCCGTTCTGCCGGCGCCGATCCGATTGAAGCTATATAC
  45◄isThrLeuLeuValValThrSerArgGluAlaProAlaSerGlyIleSerAlaIleTyrL
5761 TTCGCTTCTCTCCCCACTTTTCCAATTTGATCCGGAAATAAAACGGCCCCGGACAACAGT
  25◄ysAlaGluArgGlyValLysGlyIleGlnAspProPheLeuValAlaGlySerLeuLeuI
5821 ATCGTACGATCCGGATCC
   5◄leThrArgAspProAsp
```

FIG. 16

FIG. 21

```
   1 TGCTACCTGATGTACAAGCAAAAGGCACAACAAAGACCTTGTTATGGCTTGGGAATAAT
  61 ACCCTTGATCAGATGAGAGCCACTACAAAAATATGAATACAAACGAGAGGCGGAGGTATC
 121 CCCAATAGCAATTTGCGTGTAAATTCTGGCAACCTGTTAATTAGAAGAATTAAGAAAAAA
 181 CCACTGGATGTAAGTGACAAACAAGCAATACACGGGTAGAACGGTCGGAGAAGCCACCCC
 241 TCAATCGGGAATCAGGCCTCACAACGTCCTTTCTACCGCATCATCAATAGCAGACTTCGG
 301 TCATGGACCGTGCAGTTAGCAGAGTTGCGCTAGAGAATGAAGAAAGAGAAGCAAAGAATA
      1▶MetAspArgAlaValSerArgValAlaLeuGluAsnGluGluArgGluAlaLysAsnT
 361 CATGGCGCTTTGTATTCCGGATTGCAATCTTACTTTTAATAGTAACAACCTTAGCCATCT
    20▶hrTrpArgPheValPheArgIleAlaIleLeuLeuLeuIleValThrThrLeuAlaIleS
 421 CTGCAACCGCCCTGGTATATAGCATGGAGGCTAGCACGCCTGGCGACCTTGTTGGCATAC
    40▶erAlaThrAlaLeuValTyrSerMetGluAlaSerThrProGlyAspLeuValGlyIleP
 481 CGACTATGATCTCTAAGGCAGAAGAAAAGATTACATCTGCACTCAGTTCTAATCAAGATG
    60▶roThrMetIleSerLysAlaGluGluLysIleThrSerAlaLeuSerSerAsnGlnAspV
 541 TAGTAGATAGGATATATAAGCAGGTGGCCCTTGAGTCTCCATTGGCGTTGCTAAACACTG
    80▶alValAspArgIleTyrLysGlnValAlaLeuGluSerProLeuAlaLeuLeuAsnThrG
 601 AATCTGTAATTATGAATGCAATAACGTCTCTCTCTTATCAAATCAATGGAGCTGCAAATA
   100▶luSerValIleMetAsnAlaIleThrSerLeuSerTyrGlnIleAsnGlyAlaAlaAsnA
                                  BspHI
 661 ATAGCGGGTGTGGGGCACCTGTTCATGACCCAGATTATATCGGGGGGATAGGCAAAGAAC
   120▶snSerGlyCysGlyAlaProValHisAspProAspTyrIleGlyGlyIleGlyLysGluL
 721 TTATTGTGGATGACGCTAGTGATGTCACATCATTCTATCCCTCTGCGTTCCAAGAACACC
   140▶euIleValAspAspAlaSerAspValThrSerPheTyrProSerAlaPheGlnGluHisL
 781 TGAACTTTATCCCGGCACCTACTACAGGATCAGGTTGCACTCGGATACCCTCATTCGACA
   160▶euAsnPheIleProAlaProThrThrGlySerGlyCysThrArgIleProSerPheAspI
 841 TAAGCGCTACCCACTACTGTTACACTCACAATGTGATATTATCTGGTTGCAGAGATCACT
   180▶leSerAlaThrHisTyrCysTyrThrHisAsnValIleLeuSerGlyCysArgAspHisS
 901 CACACTCATATCAGTACTTAGCACTTGGCGTGCTTCGGACATCTGCAACAGGGAGGGTAT
   200▶erHisSerTyrGlnTyrLeuAlaLeuGlyValLeuArgThrSerAlaThrGlyArgValP
 961 TCTTTTCTACTCTGCGTTCCATCAATTTGGATGACAGCCAAAATCGGAAGTCTTGCAGTG
   220▶hePheSerThrLeuArgSerIleAsnLeuAspAspSerGlnAsnArgLysSerCysSerV
1021 TGAGTGCAACTCCCTTAGGTTGTGATATGCTGTGCTCTAAAATCACAGAGACTGAGGAAG
   240▶alSerAlaThrProLeuGlyCysAspMetLeuCysSerLysIleThrGluThrGluGluG
                                  ClaI
1081 AGGATTATAGTTCAATTACGCCTACATCGATGGTGCACGGAAGGTTAGGGTTTGACGGTC
   260▶luAspTyrSerSerIleThrProThrSerMetValHisGlyArgLeuGlyPheAspGlyG
1141 AATACCATGAGAAGGACTTAGACGTCATAACTTTATTTAAGGATTGGGTGGCAAATTACC
   280▶lnTyrHisGluLysAspLeuAspValIleThrLeuPheLysAspTrpValAlaAsnTyrP
1201 CAGGAGTGGGGGTGGGTCTTTTATTAACAACCGCGTATGGTTCCCAGTCTACGGAGGGC
   300▶roGlyValGlyGlyGlySerPheIleAsnAsnArgValTrpPheProValTyrGlyGlyL
1261 TAAAACCCAATTCGCCTAGTGACACCGCACAAGAAGGGAGATATGTAATATACAAGCGCT
   320▶euLysProAsnSerProSerAspThrAlaGlnGluGlyArgTyrValIleTyrLysArgT
1321 ACAATGACACATGCCCAGATGAACAAGATTACCAGATTCGGATGGCTAAGTCTTCATATA
   340▶yrAsnAspThrCysProAspGluGlnAspTyrGlnIleArgMetAlaLysSerSerTyrL
1381 AGCCTGGGCGGTTTGGTGGAAAACGCGTACAGCAGGCCATCTTATCTATCAAGGTGTCAA
   360▶ysProGlyArgPheGlyGlyLysArgValGlnGlnAlaIleLeuSerIleLysValSerT
1441 CATCTTTGGGCGAGGACCCGGTGCTGACTGTACCGCCTAATACAATCACACTCATGGGGG
   380▶hrSerLeuGlyGluAspProValLeuThrValProProAsnThrIleThrLeuMetGlyA
1501 CCGAACGGAGAGTTCTCACAGTAGGGACATCTCATTTCTTGTACCAGCGAGGGTCTTCAT
   400▶laGluArgArgValLeuThrValGlyThrSerHisPheLeuTyrGlnArgGlySerSerT
```

FIG. 25A

```
1561 ACTTCTCTCCTGCTTTATTATACCCTATGACAGTCAACAACAAAACGGCTACTCTTCATA
 420▶yrPheSerProAlaLeuLeuTyrProMetThrValAsnAsnLysThrAlaThrLeuHisS
1621 GTCCTTACACATTCAATGCTTTCACTAGGCCAGGTAGTGTCCCTTGTCAGGCATCAGCAA
 440▶erProTyrThrPheAsnAlaPheThrArgProGlySerValProCysGlnAlaSerAlaA
1681 GATGCCCAACTCATGTGTCACTGGAGTTTATACTGATCCGTATCCCTTAGTCTTCCATA
 460▶rgCysProAsnSerCysValThrGlyValTyrThrAspProTyrProLeuValPheHisA
1741 GGAACCATACCTTGCGGGGGGTATTCGGGACAATGCTTGATGATGAACAAGCAAGACTTA
 480▶rgAsnHisThrLeuArgGlyValPheGlyThrMetLeuAspAspGluGlnAlaArgLeuA
                  PstI
1801 ACCCTGTATCTGCAGTATTTGATAACATATCCCGCAGTCGCATAACCCGGGTAAGTTCAA
 500▶snProValSerAlaValPheAspAsnIleSerArgSerArgIleThrArgValSerSerS
1861 GCCGTACTAAGGCAGCATACACGACATCGACATGTTTTAAAGTTGTCAAGACCAATAAAA
 520▶erArgThrLysAlaAlaTyrThrThrSerThrCysPheLysValValLysThrAsnLysT
1921 CATATTGCCTCAGCATTGCAGAAATATCCAATACCCTCTTCGGGGAATTCAGGATCGTTC
 540▶hrTyrCysLeuSerIleAlaGluIleSerAsnThrLeuPheGlyGluPheArgIleValP
1981 CTTTACTAGTTGAGATTCTCAAGGATGATGGGATTTAAGAAGCCAGGTCTGGCCAGTTGA
 560▶roLeuLeuValGluIleLeuLysAsp
2041 GTCAACTGCGAGAGGGTCGGAAAGATGACATTGTGTCACCTTTTTTTTGTAATGCCAAGG
2101 ATCAAACTGGATACCGGCGCGAGCCCGAATCCTATGCTGCCAGTCAGCCATAATCAGATA
2161 GTACTAATATGATTAGTCTTAATCTTGTCGATAGTAACTTGGTTAAGAAAAAATATGAGT
2221 GGTAGTGAGATACACAGCTAAACAACTCACGAGAGATAGCACGGGTAGGACATGGCGAGC
2281 TCCGGTCCCGAAAGGGCAG..GCATCAGATTATCCTACCAGAGTCACATCTGTCCTCACCA
2341 TTGGTCAAGCACAAACTGCTCTATTACTGGAAATTAACTGGCGTACCGCTTCCTGACGAA
2401 TGTGACTTCGACCACCTCATTATCAGCCGACAATGGAAGAAAATACTTGAATCGGCCACT
2461 CCTGACACTGAGAGGATGATAAAGCTCGGGCGGGCAGTACACCAGACTCTCGACCACCGC
2521 C
```

FIG. 25B

FIG. 34

```
              10        20        30        40        50        60
               |         |         |         |         |         |
  1 GAATTCCATCACCCCCTGCCGATCTTGCACGCGGGGACGAGCAAAGCGTGCGGTGCGGGC
 61 AGAAAGACAAGGATGGCTGTGGGTTGAAAGATGAAAAACAAATCGCGGTTGTGGGTCATG
121 AGTGGAGGGAGGGTGCCATCTGTGATGCCGAGAGGTCAAACTATGTTATAAAGAAAAACG
181 ATGGGTGGGAAATATAATAAAGCAACCGAAATGGTACATAAAAACTAAAAATACCTACAC
241 GGTTACACCACCGATCAGGCGAAGAAGTTCCAAACGATTAACAACCGGGACGAGACGTTG
301 CCGTTCGATCCAGGTCTCTGCTTTTTTGTATCTCTTATCCTATACCGCCGCCTCCCGTCC
361 GACGAGAGCAAGTCGCACCGCCACTCGAGGCCACAAGAAATTACGATTCTTATACGGGTG
421 GGCGTACCGCCTACTCGAACTATCACGTGATGTGTATGCAAATGAGCAGTGCGAACGCGT
481 CAGCGTTCGCACTGCGAACCAATAATATATTATATTATATTATATTATTGGACTCTGGTG
541 CGAACGCCGAGGTGAGCCAATCGGATATGGCGATATGTTATCACGTGACATGTACCGCCC
601 CAAATTCGCACTTGAGTGTTGGGGGTACATGTGGGGCGGCTCGGCTCTTGTGTATAAAA
661 GAGCGGCGGTTGCGAGGTTCCTTCTCTCTTCGCGATGCTCTCTCAGAATGGCACGGCCGA
721 TCCCCCATATATTTCCTGAAGGAACGCATAGCTAGGCGACGAACGAGCTGAATTTCTCCC
781 TTCATCAAATAAGTAATAAA
```

FIG. 39

SEQUENCE LISTING (1) GENERAL INFORMATION:

(iii) NUMBER OF SEQUENCES: 28

(2) INFORMATION FOR SEQ ID NO: 1:

```
    (i) SEQUENCE CHARACTERISTICS:
        (A) LENGTH: 5838 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Herpesvirus of turkey
        (B) STRAIN: FC126

(ix) FEATURE:
        (A) NAME/KEY: CDS
        (B) LOCATION:676..1209
        (D) OTHER INFORMATION:/function= "unknown"
            /product= "ORF1"

(ix) FEATURE:
        (A) NAME/KEY: CDS
        (B) LOCATION:complement (1387..1941)
        (D) OTHER INFORMATION:/function= "unknown"
            /product= "ORF2"

(ix) FEATURE:
        (A) NAME/KEY: CDS
        (B) LOCATION:complement (3573..5838)
        (D) OTHER INFORMATION:/function= "unknown"
            /product= "ORF3"

(ix) FEATURE:
        (A) NAME/KEY: CDS
        (B) LOCATION:1403..1957
        (D) OTHER INFORMATION:/function= "unknown"
            /product= "ORF4"

(ix) FEATURE:
        (A) NAME/KEY: CDS
        (B) LOCATION:complement (2287..3081)
        (D) OTHER INFORMATION:/function= "unknwn"
            /product= "ORF5"

(ix) FEATURE:
        (A) NAME/KEY: CDS
        (B) LOCATION:complement (1..479)
        (D) OTHER INFORMATION:/function= "unknown"
            /product= "ORF6"

(xi) SEQUENCE DESCRIPTION: SEQ ID NO: 1:
```

```
GGATCCATCA GCAATGCGGG CTGTAGTCCC GATTCCCGTT TCAAATGAAG GTGCTCCAAC      60

ACGGTCTTCA AAGCAACCGG CATACCAGCA AACACAGACT GCAACTCCCC GCTGCAATGA     120

TTGGTTATAA ACAGTAATCT GTCTTCTGGA AGTATATTTC GCCCGACAAT CCACGGCGCC     180

CCCAAAGTTA AAAACCATCC ATGTGTATTT GCGTCTTCTC TGTTAAAAGA ATATTGACTG     240

GCATTTTCCC GTTGACCGCC AGATATCCAA AGTACAGCAC GATGTTGCAC GGACGACTTT     300

GCAGTCACCA GCCTTCCTTT CCACCCCCCC ACCAACAAAA TGTTTATCGT AGGACCCATA     360

TCCGTAATAA GGATGGGTCT GGCAGCAACC CCATAGGCGC CTCGGCGTGG TAGTTCTCGA     420

GGATACATCC AAAGAGGTTG AGTATTCTCT CTACACTTCT TGTTAAATGG AAAGTGCATT     480

TGCTTGTTCT TACAATCGGC CCGAGTCTCG TTCACAGCGC CTCGTTCACA CTTAAACCAC     540

AAATAGTCTA CAGGCTATAT GGGAGCCAGA CTGAAACTCA CATATGACTA ATATTCGGGG     600

GTGTTAGTCA CGTGTAGCCC ATTGTGTGCA TATAACGATG TTGGACGCGT CCTTATTCGC     660

GGTGTACTTG ATACTATGGC AGCGAGCATG GGATATTCAT CCTCGTCATC GTTAACATCT     720

CTACGGGTTC AGAATGTTTG GCATGTCGTC GATCCTTTGC CCATCGTTGC AAATTACAAG     780

TCCGATCGCC ATGACCGCGA TAAGCCTGTA CCATGTGGCA TTAGGGTGAC ATCTCGATCA     840

TACATTATAA GACCAACGTG CGAGTCTTCC AAAGACCTGC ACGCCTTCTT CTTCGGATTG     900
```

```
TCAACGGGTT CTTCAGAATC TATGCCCATA TCTGGCGTTG AGACCATTGT GCGTTTAATG      960

AACAATAAAG CGGCATGCCA TGGAAAGGAG GGCTGCAGAT CTCCATTTTC TCACGCCACT     1020

ATCCTGGACN CTGTAGACGA TAATTATACC ATGAATATAG AGGGGGTATG TTTCCACTGC     1080

CACTGTGATG ATAAGTTTTC TCCAGATTGT TGGATATCTG CATTTTCTGC TGCCGAACAA     1140

ACTTCATCGC TATGCAAAGA GATGCGTGTG TACACGCNGC CGTTGAGTAT ACGGGAAACT     1200

AAATGTTCAT AGAGGTCTTT GGGCTATATG TTATTAAATA AAATAATTGA CCAGTGAACA     1260

ATTTGTTTAA TGTTAGTTTA TTCAATGCAT TGGTTGCAAA TATTCATTAC TTCTCCAATG     1320

CCAGGTCATT CTTTAGCGAG TGATGTTATG ACATTGCTGT GAAAATTACT ACAGGATATA     1380

TTTTTAAGAT GCAGGAGTAA CAATGTGCAT AGTAGGCGTA GTTATCGCAG ACGTGCAACG     1440

CTTCGCATTT GAGTTACCGA AGTGCCCAAC AGTGCTGCGG TTATGGTTTA TGCGCACAGA     1500

ATCCATGCAT GTCCTAATTG AACCATCCGA TTTTTCTTTT AATCGCGATC GTTGTTTGGG     1560

CAACTGCGTT ATTTCAGATC TAAAAAATTT ACCCTTTATG ACCATCACAT CTCTCTGGCT     1620

CATACCCCGC TTGGATAAGA TATCATGTAG ATTCCGCCCT AAGAAATGCA AACTAACATT     1680

ATTGTCGGTT CCATATACAC TTCCATCTTG TCCTTCGAAA ATAACAAACT CGCGCAATAG     1740

ACCGTCCGTA CATGCATGGC CGATGTGTGT CAACATCATT GGTCTGCTAG ATCCCGATGG     1800

GACGAATCGT ACAGTCGTCG CTCCAGCATT GGCAAAAATC CCCAGATACC CTCCATGCGG     1860

CAAATCTAAA TTGCGACCCC GAAGAGACTG CACCAAAGTC TTATCGACGC ACGCTGATTT     1920

TTTTGAACAG CGGGAGCCCA TTATCTTCAG TGGAGCGTAG ACGGGCGAGG CTAATTATGT     1980

GACATAGCAA CACTGCATGT ATGTTTTTAT AAATCAATAA GAGTACATAA TTTATTACGT     2040

ATCATTTCCG TTTGTAATAT ACTGTATACA TCATCCACAC TATTAGTCAG CACTAGCGCG     2100

CGGGCGCACG TTACAATAGC AGCGTGCCCG TTATCTATAT TGTCCGATAT TTACACATAA     2160

CATTTCATCG ACATGATTAA ATACCTAAGT ACTGCACACA GATGTTTAAT GTATATCGTC     2220

ATATAAATTA TATCGCTAGG ACAGACCCAA ACGACCTTTA TCCCAAACAG TCAGATCCTC     2280

TTCTCAAGTG TCGATTTCTG TTATGGAATA TGCATACCCT GGCCCAGAAA TTGCACGCAC     2340

GAGCGTAGTG AATGCGTCAT TGGTTTTACA TTTAAAGGCT AAATGCACAA ATTCTTTAGA     2400

CGACAGCACA TCGTTAAATA GCATCTCTAG CGTTCTTATG AATGCTAAGC ATTGGAGTCC     2460

TCCTGGTCGG CCACAATAAC AGCTGAGTAT CATACCCTGA GCTCCGGGGT TGTCGCACAT     2520

AGCGGATTCG TATAAACATA GGATTTTCCG CGAATCCATC AGTTGCAAAA ATCTGTTAGG     2580

CTCCATCAAC AACGCTGGAT TTACTTCAGA TCCACGCGTA AAGTAATGGT GCTCGAATAC     2640

CGTTTTTAGA GTTGTCGGCA TTTCAAGGAA CAAAGAATTC ATTTCTTCAT TGCAACGACG     2700

CGCCAGAAAT CCCAAGACCT CTTTGGGTAG TATGTTCTTG CCTATAAAAC ACGGCGTTCC     2760

AAGTGCCAGG AACCACGCAT GTGTTACTGT TGGGGCGTAT TCAGAAATAA AGCGGGGTTT     2820

ATGCGGCTTT TGAAGCTCGG ATATCCAAAG TATCGCTTGC TGATGAACGA GCGATGTAGC     2880

TGTTACAAAA CCTCCTTTCC ATCCTCCAGT CAACATAATA TTTATCGGCC TACCTATGTC     2940

CGTAATAAGT ATTGGTCGGG CAATTATTCC GTATGAGGTC TTGCAGGAAT AAGCTCTTAG     3000

GGACAGCCAG CTTGGATATG GTGCGAAACA GACCTTCTCG GCTTCAGAAT GTCGCTCCGC     3060

AGTCTCTTCG TGTCGGTGCA TCTTAGATCC ACCATCAATG TGTGCAGCAT TGACTCCCGC     3120

CCGTCGAATA TTCCTTTTGT TACGATGCAG TAATGAGCAC GATCATGGGC GGGGCGATGA     3180

CGTTCTATTT GCATGTCTGC GAACAATTTG CGTCAGTCAT ACAGCTATGG AGTGGGCCAT     3240

TTCTGGCGTC AACTTAAAAA CGCGAACCGC AGACATATGT ATTTGCATGC AAAGACGTAT     3300
```

```
CTTCGTATTT CTGGGCATCT TCAAATGCTC TGGCCAATAT GGCAATGAAT TTGGATTCGT    3360

TTGACGCCGA TGGTATGCAG TGCAAATGTG CCAATAGCCC ACATCCGAAA AAGTTATTTG    3420

TCATACAAGC AGGTGTTAAG TAGCAATCAC ATAAAGGCAC CAGACGCCTC ATGGCATCAT    3480

AATGAATAGC TCCTTCTCCC CACTGGAACC ACTGACAAAA TCTGCGAGTA TATTCCGCAA    3540

ACCACATTTT ATTTCTCATA GAAACTACCC TAAATCCTTT TAACGGGGAA GAAGAATCCT    3600

AGATAGTGCT TGAAGTCATG ACTGTTACTG CTGCAATAAC ACTGTATATT ATTTATAAAT    3660

TCCGTTTGTC TAGGTATCTG ATGTAGGCAT TCCGATCCCT TTACTATTGC GTCTTCACGA    3720

CCAAATGGGA ATGCGCCAAA ATCCCCACAC CTCATCACCC TGGAGGCAGA TTGTGTATTA    3780

TTAATATCCG CCGATTGAAG CACAAAACGG TACGGTACTG TTCCTAATTC TGGTATAGAT    3840

TCTATGGTCA AAAGTCTGCA TATCCCCGAC ATTGCCATGA GATCACACAG TCCAAGTAGC    3900

ATGTTTATTG AGTCACTCAG ACTGTCAACG TCCCTCGCCG CACCACCAAT CGAAAATAAA    3960

GTATCTACGC AAGTTATAGC TCCGCATTTT CTATCGCTAG CAGCAATCGC GACGCAAAAC    4020

ATAAAGGCCA TGTTGGGATT TGAACTCTCT GGGGGGCTTG TTATCTTCTG CACCGTCGCA    4080

GTCGCAGTTT TCCGAAATTT ATGTCTAATA TATTTTCCGG CCGTGCTCCA ATCGGCCGAA    4140

AAGAATCTGC GTATTACCAG ACTCATTGAC GGGCCGATAA AGACCATAAA ACAAAATTCC    4200

TGTGCACTCC CTCCTCCAGT TTTGCCATCG TCCAAGTCCC GTAACTTTTT TTGCGTTTCG    4260

AGGAGCAAGC GTTCGTTATC CCTACCCACA CTTGTTTTCC ACCGTTTTCT TATTATAAGC    4320

GGTTGTATCG CCAACGCGTC ACCGCAGGTT GTCACATACA GTGATGGCAT ACTTGAACGT    4380

GCAACAACGC GCTCGCTTTG CAAATCTAAG TCATTGACCA TCAAATCGCG TTGAGAGGAT    4440

AGCCAGGCAT CTTTTTTCCT AGTATGGTGA CGGTGCAGCC ACCCCAACTC AGTTCTTGTA    4500

AAAAAAGCTA TTGGCGGGAA TTTATGTTCT GAGGTGCATT CTATATTTAT GAGTCCATCA    4560

AATGCCATTA ACCAGATTCG TATTTTTTCG CTCGACCCGG CATCACTATG GATACAATAC    4620

CTTTCTATGG CCCATTTCAG CTCTCGAACC AACCACACGG ACAATTGACT AACATAAGTA    4680

TGATCTTTAT CACAGTCGCA CCCATCTGAG TTATATTTAT GGCATCCGAG CGCTCTTACT    4740

GTACGGTCGG ATACACCCAT GGTTTTTCCT TTATATAGTC GGGTTATAGT CTGTCGGGTT    4800

TGGCGGTAGC ACGGAGTAGT TTGATTTTTA AGAATCGAAA ACCGGCTTGG AGAGACCACT    4860

GTCGAATATT TGTCCGTATA CTCTACACGT GAGTGTTGTC CATTCCTAGG TATATTCATC    4920

TGTTCGGATA CCTTCAATTG CTGTTCAGGC ATAACCTTAA AGCATATGTT ATGTTGTACA    4980

TCAAAACTTG GTGAGTTATG TTCGATTGCC GCGCATAAAG AATCGTACAT GAGCGTTTCT    5040

GCTAACATAC TATCTATATT CTCACACGCC CCTGCATATA CTGTTCCTAT TCCAAATTCA    5100

CGTTTTGCCC CATCGGCTAT CTGCTCCCAA AAAGTTGTAA TATAGGTGCC GCTGGGTGCG    5160

AAATTTTCAT CAGTTGTATT CCTGATAAAC TGAATCACTT TACATAATTT TTGCCACATA    5220

TCTGCGTGCA GCCATAGTAT CGAACCCGTG GGCTCGGAGA CGACAGTGCG TACAATGGGT    5280

ATTTTACCTT TCCCCAACAA AATAATGGTA TACAAGTTAG GTCCGTACCT AGACCTTAAT    5340

GTTTCCAATT CTTCTGAATC ACTGCACTCT CGTAGGGGAG TAACGGTAAT AATTTCGTCT    5400

CTGAGCCCCG TTTTGCGTTG AAAACTAATC ACATTAGATA ATGTGCAATC GGTTTCTTTT    5460

ATCCGGATAC ATCTAAGTAT TATGACATCG GTGGTCATTG TTTCCATCAA CGACCATCTT    5520

TTACGATCGC CCATACTACT CATGGACGTT GTCGGTGTTG AAAAATCACC AGAATTGCAA    5580

CGGATCTCTG GGTACCATGC TGCTGATGGA ATTGGCGGTT TTAATTGTTG TTTCAGTCTA    5640

TTATTGCTAT CTTTGGCGGG GTTGAATAAT GTGGGGGGAG AGTGATTGCA GGAATCCGAA    5700
```

```
TGGGTCAATA AAACGACCGT GCTCCGTTCT GCCGGCGCCG ATCCGATTGA AGCTATATAC    5760

TTCGCTTCTC TCCCCACTTT TCCAATTTGA TCCGGAAATA AAACGGCCCC GGACAACAGT    5820

ATCGTACGAT CCGGATCC                                                  5838
```

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 2:

```
CATTATAAGA CCAACGTGCG AGTC                                             24
```

(2) INFORMATION FOR SEQ ID NO: 3:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 3:

```
GTTCACGTCG ACAATTATTT TATTTAATAA C                                     31
```

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 4:

```
AAGATAATGG GCTCCCGCTG TTC                                              23
```

(2) INFORMATION FOR SEQ ID NO: 5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 5:

```
TAATTGTCGA CCCCGGGGAA TTCGTTTAAT GTTAGTTTAT TC                         42
```

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

```
GAAATGCAAA CTAACATTAT TGTC                                                            24

(2) INFORMATION FOR SEQ ID NO: 7:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

GTGTAAATAG TCGACAATAT AGATAACGGG C                                                    31

(2) INFORMATION FOR SEQ ID NO: 8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

CTATATTGTC GACCCCGGGG AATTCATCGA CATGATTAAA TAC                                        43

(2) INFORMATION FOR SEQ ID NO: 9:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

CAATGAAGAA ATATTTTCTT TGTTCCTTGA AATGC                                                 35

(2) INFORMATION FOR SEQ ID NO: 10:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

CCGAATTCAT ATAAGCTTAC GTG                                                             23

(2) INFORMATION FOR SEQ ID NO: 11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

TCGACACGTA AGCTTATATG AATTCGGCAT G                                                    31
```

(2) INFORMATION FOR SEQ ID NO: 12:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

CGAATTCACT AGTGTGTGTC TGCAGGCGGC CGCGTGTGTG TCGACGGTAC      50

(2) INFORMATION FOR SEQ ID NO: 13:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

CGTCGACACA CACGCGGCCG CCTGCAGACA CACACTAGTG AATTCGAGCT      50

(2) INFORMATION FOR SEQ ID NO: 14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

GACTGGTACC GCGGCCGCAT GCACTTTTTA GGCGGAATTG      40

(2) INFORMATION FOR SEQ ID NO: 15:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

TTCGGGACAT TTTCGCGG      18

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

TATATGGCGT TAGTCTCC      18

(2) INFORMATION FOR SEQ ID NO: 17:

(i) SEQUENCE CHARACTERISTICS:
        (A) LENGTH: 41 base pairs
        (B) TYPE: nucleic acid (C) STRANDEDNESS: single
        (D) TOPOLOGY: linear (ii) MOLECULE TYPE: other nucleic acid (xi) SEQUENCE DESCRIPTION: SEQ ID NO: 17:

TTGCGAGCTC GCGGCCGCTT ATTACACAGC ATCATCTTCT G                            41

(2) INFORMATION FOR SEQ ID NO: 18:

(i) SEQUENCE CHARACTERISTICS:
        (A) LENGTH: 2521 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Newcastle disease virus
        (B) STRAIN: TEXAS (ix) FEATURE:
        (A) NAME/KEY: CDS
        (B) LOCATION:303..2015
        (D) OTHER INFORMATION:/product= "Hemagglutinin
            neuraminidase"
            /gene= "HN"

(xi) SEQUENCE DESCRIPTION: SEQ ID NO: 18:

TGCTACCTGA TGTACAAGCA AAAGGCACAA CAAAAGACCT TGTTATGGCT TGGGAATAAT         60

ACCCTTGATC AGATGAGAGC CACTACAAAA ATATGAATAC AAACGAGAGG CGGAGGTATC        120

CCCAATAGCA ATTTGCGTGT AAATTCTGGC AACCTGTTAA TTAGAAGAAT TAAGAAAAAA        180

CCACTGGATG TAAGTGACAA ACAAGCAATA CACGGGTAGA ACGGTCGGAG AAGCCACCCC        240

TCAATCGGGA ATCAGGCCTC ACAACGTCCT TTCTACCGCA TCATCAATAG CAGACTTCGG        300

TCATGGACCG TGCAGTTAGC AGAGTTGCGC TAGAGAATGA AGAAAGAGAA GCAAAGAATA        360

CATGGCGCTT TGTATTCCGG ATTGCAATCT TACTTTTAAT AGTAACAACC TTAGCCATCT        420

CTGCAACCGC CCTGGTATAT AGCATGGAGG CTAGCACGCC TGGCGACCTT GTTGGCATAC        480

CGACTATGAT CTCTAAGGCA GAAGAAAAGA TTACATCTGC ACTCAGTTCT AATCAAGATG        540

TAGTAGATAG GATATATAAG CAGGTGGCCC TTGAGTCTCC ATTGGCGTTG CTAAACACTG        600

AATCTGTAAT TATGAATGCA ATAACGTCTC TCTCTTATCA AATCAATGGA GCTGCAAATA        660

ATAGCGGGTG TGGGGCACCT GTTCATGACC CAGATTATAT CGGGGGGATA GGCAAAGAAC        720

TTATTGTGGA TGACGCTAGT GATGTCACAT CATTCTATCC CTCTGCGTTC CAAGAACACC        780

TGAACTTTAT CCCGGCACCT ACTACAGGAT CAGGTTGCAC TCGGATACCC TCATTCGACA        840

TAAGCGCTAC CCACTACTGT TACACTCACA ATGTGATATT ATCTGGTTGC AGAGATCACT        900

CACACTCATA TCAGTACTTA GCACTTGGCG TGCTTCGGAC ATCTGCAACA GGGAGGGTAT        960

TCTTTTCTAC TCTGCGTTCC ATCAATTTGG ATGACAGCCA AAATCGGAAG TCTTGCAGTG       1020

TGAGTGCAAC TCCCTTAGGT TGTGATATGC TGTGCTCTAA AATCACAGAG ACTGAGGAAG       1080

AGGATTATAG TTCAATTACG CCTACATCGA TGGTGCACGG AAGGTTAGGG TTTGACGGTC       1140

AATACCATGA GAAGGACTTA GACGTCATAA CTTTATTTAA GGATTGGGTG GCAAATTACC       1200

CAGGAGTGGG GGGTGGGTCT TTTATTAACA ACCGCGTATG GTTCCCAGTC TACGGAGGGC       1260

TAAAACCCAA TTCGCCTAGT GACACCGCAC AAGAAGGGAG ATATGTAATA TACAAGCGCT       1320

```
ACAATGACAC ATGCCCAGAT GAACAAGATT ACCAGATTCG GATGGCTAAG TCTTCATATA    1380

AGCCTGGGCG GTTTGGTGGA AAACGCGTAC AGCAGGCCAT CTTATCTATC AAGGTGTCAA    1440

CATCTTTGGG CGAGGACCCG GTGCTGACTG TACCGCCTAA TACAATCACA CTCATGGGGG    1500

CCGAAGGCAG AGTTCTCACA GTAGGGACAT CTCATTTCTT GTACCAGCGA GGGTCTTCAT    1560

ACTTCTCTCC TGCTTTATTA TACCCTATGA CAGTCAACAA CAAAACGGCT ACTCTTCATA    1620

GTCCTTACAC ATTCAATGCT TTCACTAGGC CAGGTAGTGT CCCTTGTCAG GCATCAGCAA    1680

GATGCCCCAA CTCATGTGTC ACTGGAGTTT ATACTGATCC GTATCCCTTA GTCTTCCATA    1740

GGAACCATAC CTTGCGGGGG GTATTCGGGA CAATGCTTGA TGATGAACAA GCAAGACTTA    1800

ACCCTGTATC TGCAGTATTT GATAACATAT CCCGCAGTCG CATAACCCGG GTAAGTTCAA    1860

GCCGTACTAA GGCAGCATAC ACGACATCGA CATGTTTTAA AGTTGTCAAG ACCAATAAAA    1920

CATATTGCCT CAGCATTGCA GAAATATCCA ATACCCTCTT CGGGGAATTC AGGATCGTTC    1980

CTTTACTAGT TGAGATTCTC AAGGATGATG GGATTTAAGA AGCTTGGTCT GGCCAGTTGA    2040

GTCAACTGCG AGAGGGTCGG AAAGATGACA TTGTGTCACC TTTTTTTTGT AATGCCAAGG    2100

ATCAAACTGG ATACCGGCGC GAGCCCGAAT CCTATGCTGC CAGTCAGCCA TAATCAGATA    2160

GTACTAATAT GATTAGTCTT AATCTTGTCG ATAGTAACTT GGTTAAGAAA AAATATGAGT    2220

GGTAGTGAGA TACACAGCTA ACAACTCAC GAGAGATAGC ACGGGTAGGA CATGGCGAGC     2280

TCCGGTCCCG AAAGGGCAGA GCATCAGATT ATCCTACCAG AGTCACATCT GTCCTCACCA    2340

TTGGTCAAGC ACAAACTGCT CTATTACTGG AAATTAACTG GCGTACCGCT TCCTGACGAA    2400

TGTGACTTCG ACCACCTCAT TATCAGCCGA CAATGGAAGA AAATACTTGA ATCGGCCACT    2460

CCTGACACTG AGAGGATGAT AAAGCTCGGG CGGGCAGTAC ACCAGACTCT CGACCACCGC    2520

C                                                                    2521

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

CAGACCAAGC TTCTTAAATC CC                                              22

(2) INFORMATION FOR SEQ ID NO: 20:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

GTATTCGGGA CAATGC                                                     16

(2) INFORMATION FOR SEQ ID NO: 21:

(i) SEQUENCE CHARACTERISTICS:
        (A) LENGTH: 21 base pairs
        (B) TYPE: nucleic acid
        (C) STRANDEDNESS: single
```

(D) TOPOLOGY: linear (ii) MOLECULE TYPE: other nucleic acid (xi) SEQUENCE DESCRIPTION: SEQ ID NO: 21:

GTGACATCAC TAGCGTCATC C                                              21

(2) INFORMATION FOR SEQ ID NO: 22:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 22:

CCGCATCATC AGCGGCCGCG ATCGGTCATG GACAGT                              36

(2) INFORMATION FOR SEQ ID NO: 23:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 23:

TGACCCTGTC TGGGATGA                                                  18

(2) INFORMATION FOR SEQ ID NO: 24:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: other nucleic acid (xi) SEQUENCE DESCRIPTION: SEQ ID NO: 24:

GGATCCCGGT CGACACATTG CGGCCGCAAG ATGGGC                              36

(2) INFORMATION FOR SEQ ID NO: 25:

(i) SEQUENCE CHARACTERISTICS:
            (A) LENGTH: 800 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (A) ORGANISM: Marek's disease gammaherpesvirus
            (B) STRAIN: RB1B (xi) SEQUENCE DESCRIPTION: SEQ ID NO: 25:

GAATTCCATC ACCCCCTGCC GATCTTGCAC GCGGGGACGA GCAAAGCGTG CGGTGCGGGC    60

AGAAAGACAA GGATGGCTGT GGGTTGAAAG ATGAAAAACA AATCGCGGTT GTGGGTCATG    120

AGTGGAGGGA GGGTGCCATC TGTGATGCCG AGAGGTCAAA CTATGTTATA AAGAAAAACG    180

-continued

```
ATGGGTGGGA AATATAATAA AGCAACCGAA ATGGTACATA AAAACTAAAA ATACCTACAC      240

GGTTACACCA CCGATCAGGC GAAGAAGTTC CAAACGATTA ACAACCGGGA CGAGACGTTG      300

CCGTTCGATC CAGGTCTCTG CTTTTTTGTA TCTCTTATCC TATACCGCCG CCTCCCGTCC      360

GACGAGAGCA AGTCGCACCG CCACTCGAGG CCACAAGAAA TTACGATTCT TATACGGGTG      420

GGCGTACCGC CTACTCGAAC TATCACGTGA TGTGTATGCA AATGAGCAGT GCGAACGCGT      480

CAGCGTTCGC ACTGCGAACC AATAATATAT TATATTATAT TATATTATTG GACTCTGGTG      540

CGAACGCCGA GGTGAGCCAA TCGGATATGG CGATATGTTA TCACGTGACA TGTACCGCCC      600

CAAATTCGCA CTTGAGTGTT GGGGGTACAT GTGGGGCGG CTCGGCTCTT GTGTATAAAA       660

GAGCGGCGGT TGCGAGGTTC CTTCTCTCTT CGCGATGCTC TCTCAGAATG GCACGGCCGA      720

TCCCCCATAT ATTTCCTGAA GGAACGCATA GCTAGGCGAC GAACGAGCTG AATTTCTCCC     780

TTCATCAAAT AAGTAATAAA                                                 800
```

(2) INFORMATION FOR SEQ ID NO: 26:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 26:

```
GGTCTACTAG TATTGGACTC TGGTGCGAAC GC                                    32
```

(2) INFORMATION FOR SEQ ID NO: 27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 27:

```
GTCCAGAATT CGCGAAGAGA GAAGGAACCT C                                     31
```

(2) INFORMATION FOR SEQ ID NO: 28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 28:

```
GTGTCCTGCA GTCGCGAAGA GAGAAGGAAC CTC                                   33
```

LIVE RECOMBINANT AVIAN VACCINE USING AN AVIAN HERPESVIRUS AS VECTOR

The present invention relates to vaccines for avian use based on live recombinant avian herpesviruses, namely, in particular, on Marek's disease virus (MDV) and more especially on HVT virus (herpesvirus of turkeys), into which has been inserted, by genetic recombination, at least one nucleotide sequence coding for and expressing an antigenic polypeptide of an avian pathogenic agent, under conditions affording an immunization leading to an effective protection of the vaccinated animal against the said pathogenic agent. It applies, furthermore, to the infectious laryngotracheitis virus (ILTV) and herpes of ducks.

A number of recombinant avian viral vectors have already been proposed with a view to vaccinating birds against avian pathogenic agents, in particular pathogenic viruses, including the viruses of Marek's disease (MDV), of Newcastle disease (NDV), of infectious laryngotracheitis (ILTV), of Gumboro disease (infectious bursal disease, IBDV), of infectious bronchitis (IBV) and of avian anaemia (CAV).

The viral vectors used comprise avipox viruses, especially fowlpox (EP-A-0,517,292; H. -G. Heine et al., Arch. Virol. 1993. 131. 277–292; D. B. Boyle et al., Veterinary Microbiology 1994. 41. 173–181; C. D. Bayliss et al., Arch Virol. 1991. 120. 193–205), Marek's virus, in particular serotypes 2 and 3 (HVT) (WO-A-87/04463; WO-A-89/01040; WO-A-93/25665; EP-A-0,513,921; J. McMillen, Poultry Condemnation Meeting, October 1994, 359–363; P. J. A. Sondermeijer et al., Vaccine 1993. 11. 349–357; R. W. Morgan et al., Avian Diseases 1992. 36. 858–870, and 1993. 37. 1032–1040) or alternatively the ILTV and avian adenovirus viruses.

When they are used for vaccination, these recombinant viruses induce variable levels of protection, generally low or partial, even if in special rare cases a substantial protection may be demonstrated.

One of the most difficult protections to be afforded with live recombinant avian vaccines is that against the Gumboro disease virus or IBDV virus. In effect, although traditional inactivated or attenuated live vaccines exist against this disease, no recombinant live vaccine has yet evinced appropriate efficacy.

The genome of the Gumboro disease virus consists of a double-stranded RNA. The largest segment (segment A) codes for a polyprotein of 115 kDa, which is cleaved secondarily into three proteins VP2 (41 kDa), VP4 (28 kDa) and VP3 (32 kDa). VP4 appears to be a protease participating in the maturation of 115 kDa polyprotein. The position of the cleavage site between VP2 and VP4 has been determined only approximately (M. Jagadish, J. Virol. 1988. 62. 1084–1087). The protein VP2 is an immunogen inducing neutralizing antibodies and protection against Gumboro disease.

The proposal has already been made to insert genes coding for immunogenic IBDV proteins into various live vectors: EP-A-0,517,292 (insertion of sequences coding for VP2 or the polyprotein into an avipox); C. D. Bayliss 1991, H. -G. Heine 1993 and D. B. Boyle 1994 supra (VP2 into fowlpox).

The Marek's disease viruses have also been proposed in WO-A-90/02802 and WO-A-90/02803 (various insertion sites such as gC, TK, RR1, RR2), in French Patent Applications Nos. 90/03105 (RR2) and 90/11146 (US3), and also, in particular, in Patent Applications WO-A-87/04463 and WO-A-89/01040 (BamHI #16 and #19) and WO-A-93/25655 (US2).

R. J. Isfort et al. (Virology 1994. 203. 125–133) have determined a number of sites for integration of retroviruses in the HVT genome, which sites are located in the BamHI restriction fragments F, A and I.

Various promoters, including those generally available on the market, have been used in the different constructions of the prior art, among them the PRV gX, HCMV IE (human CMV immediate early) and herpes simplex alpha-4 promoters, FPV P.E/L (fowlpox promoter) (H. Heine et al., Arch. Virol. 1993. 131. 277–292), the vaccinia virus P7.5 (C. Bayliss et al., Arch. Virol. 1991. 120. 193–205) and P11 (D. Boyle et al., Vet. Microb. 1994. 41. 173–181) promoters, the promoter originating from the RSV virus (Rous sarcoma virus) LTR sequence, the SV40 early promoter and also MDV or HVT promoters, such as the promoters of the gB, gC, TK, RR2, and the like, genes, without a rule having been discernible, in particular in the case of constructions in HVT. The sequences of some promoters can inhibit the replication of recombinant HVT or MDV vectors (D. R. Marshall et al., J. Vir. Meth. 1992. 40. 195–204 and Virology 1993. 195. 638–648). Among the promoters mentioned, a number, such as, for example, SV40, RSV LTR and PRV gX, have shown some degree of efficacy, as have some promoters belonging to some genes of the Marek viruses, in particular of serotype 3.

The invention has enabled a live recombinant vaccine to be developed, based on an HVT vector into which is inserted at least one sequence coding for an avian immunogen, especially the IBDV protein VP2. Such a vaccine incorporating a sequence coding for VP2 affords satisfactory protection of animals against Gumboro disease, that is to say protection with respect to mortality and with respect to lesions of the bursa of Fabricius.

The subject of the present invention is a live recombinant avian vaccine comprising, as vector, an avian herpesvirus comprising at least one nucleotide sequence coding for and expressing an antigenic polypeptide of an avian pathogenic agent, inserted into the region lying between the ATG of ORF UL55 and the junction of $U_L$ with the adjacent repeat region, under the control of the CMV immediate early promoter. This insertion region corresponds in HVT to the BamHI fragment I and in MDV to the BamHI fragment K+H, as are presented by A. E. Buckmaster in J. Gen. Virol. 1988. 69. 2033–2042.

The avian herpesviruses according to the invention are preferably the Marek's disease viruses, in particular HVT, the infectious laryngotracheitis virus ILTV and herpes of ducks. The Marek's disease viruses, and more especially the HVT virus, are preferred.

The BamHI restriction fragment I of HVT comprises several ORFs and three intergenic regions and, as an insertion region according to the invention, comprises several preferred insertion regions, namely the three intergenic regions 1, 2 and 3 which are the preferred regions, and ORF UL55.

Insertion into the insertion region is understood to mean, in particular, insertion without deletion or with deletion of a few bases for the intergenic regions, and with total or partial deletion or without deletion for the ORFs.

CMV immediate early (IE) promoter is understood to mean the fragment given in the examples, as well as its subfragments which retain the same promoter activity.

The CMV IE promoter can be the human promoter (HCMV IE) or the murine promoter (MCMV IE), or alternatively a CMV IE promoter of some other origin, for example from rats or from guinea-pigs.

The nucleotide sequence inserted into the Marek vector, in order to be expressed, may be any sequence coding for an antigenic polypeptide of an avian pathogenic agent, capable, when expressed under the favourable conditions achieved by the invention, of affording an immunization leading to an effective protection of the vaccinated animal against the pathogenic agent. The nucleotide sequences coding for the antigens of interest for a given disease may hence be inserted under the conditions of the invention.

The vaccines according to the invention may be used for the vaccination in ovo of 1-day or older chicks and of adults.

The invention may be used, in particular, for the insertion of a nucleotide sequence coding appropriately for the polypeptide VP2 of the IBDV virus. A live recombinant vaccine is thereby obtained affording, in addition to protection against Marek's disease, satisfactory protection against Gumboro disease. If so desired, it is also possible to insert a sequence coding for another IBDV antigen, such as VP3 or alternatively the polyprotein VP2+VP4+VP3, these other possibilities not being preferred.

The recombinant vaccine against Gumboro disease will preferably be presented at a concentration of 10 to $10^4$ pfu/dose.

Other preferred cases of the invention are the insertion of nucleotide sequences coding for antigens of the Marek's disease virus, especially gB, gC, gD and gH+gL genes (WO-A-90/02803), of the Newcastle disease virus, especially F and HN genes, of the infectious bronchitis virus (IBV), especially S and M genes (M. Binns et al., J. Gen. Virol. 1985. 66. 719–726; M. Boursnell et al., Virus Research 1984. 1. 303–313), of the avian anaemia virus (CAV), especially VP1 (52 kDa)+VP2 (24 kDa) (N. H. M. Noteborn et al., J. Virol. 1991. 65. 3131–3139), and of the infectious laryngotracheitis virus (ILTV), especially gB (WO-A-90/02802), gC, gD and gH+gL.

The doses will preferably be the same as those for the Gumboro vaccine.

According to an advantageous development of the invention, the CMV IE promoter is combined with another promoter according to a head-to-tail arrangement, which enables two nucleotide sequences to be inserted into the insertion region, one under the control of the CMV IE promoter, the other under that of the promoter used in combination therewith. This construction is noteworthy for the fact that the presence of the CMV IE promoter, and in particular of its activator portion (enhancer), activates the transcription induced by the promoter used in combination. A preferred promoter used in combination is the Marek 1.8 RNA promoter, the transcriptional activity of which has been shown to be multiplied by approximately 4.4 under these conditions.

An advantageous case of the invention is a vaccine comprising a nucleotide sequence coding for IBDV VP2 under the control of CMV IE, and a nucleotide sequence coding for an antigen of another avian disease, in particular the ones mentioned above, under the control of the other promoter.

It is also possible to assemble head to tail two CMV IE promoters of different origins.

The 1.8 RNA promoter may also be used alone in place of the CMV IE promoter, in particular for vaccines against Marek's disease, Newcastle disease, infectious laryngotracheitis, infectious bronchitis and avian anaemia.

The subject of the present invention is also a polyvalent vaccine formula comprising, as a mixture or to be mixed, at least two live recombinant avian vaccines as are defined above, these vaccines comprising different inserted sequences, in particular from different pathogens.

The subject of the present invention is also a method of avian vaccination, comprising the administration of a live recombinant vaccine or of a polyvalent vaccine formula as defined above. Its subject is, in particular, a method of this kind for the vaccination in ovo of 1-day or older chicks and of adults.

The invention will now be described in greater detail by means of non-limiting examples of implementation, taken with reference to the drawing, wherein:

Listing of figures and sequences for the constructions in the intergenic sites

Figure 11:
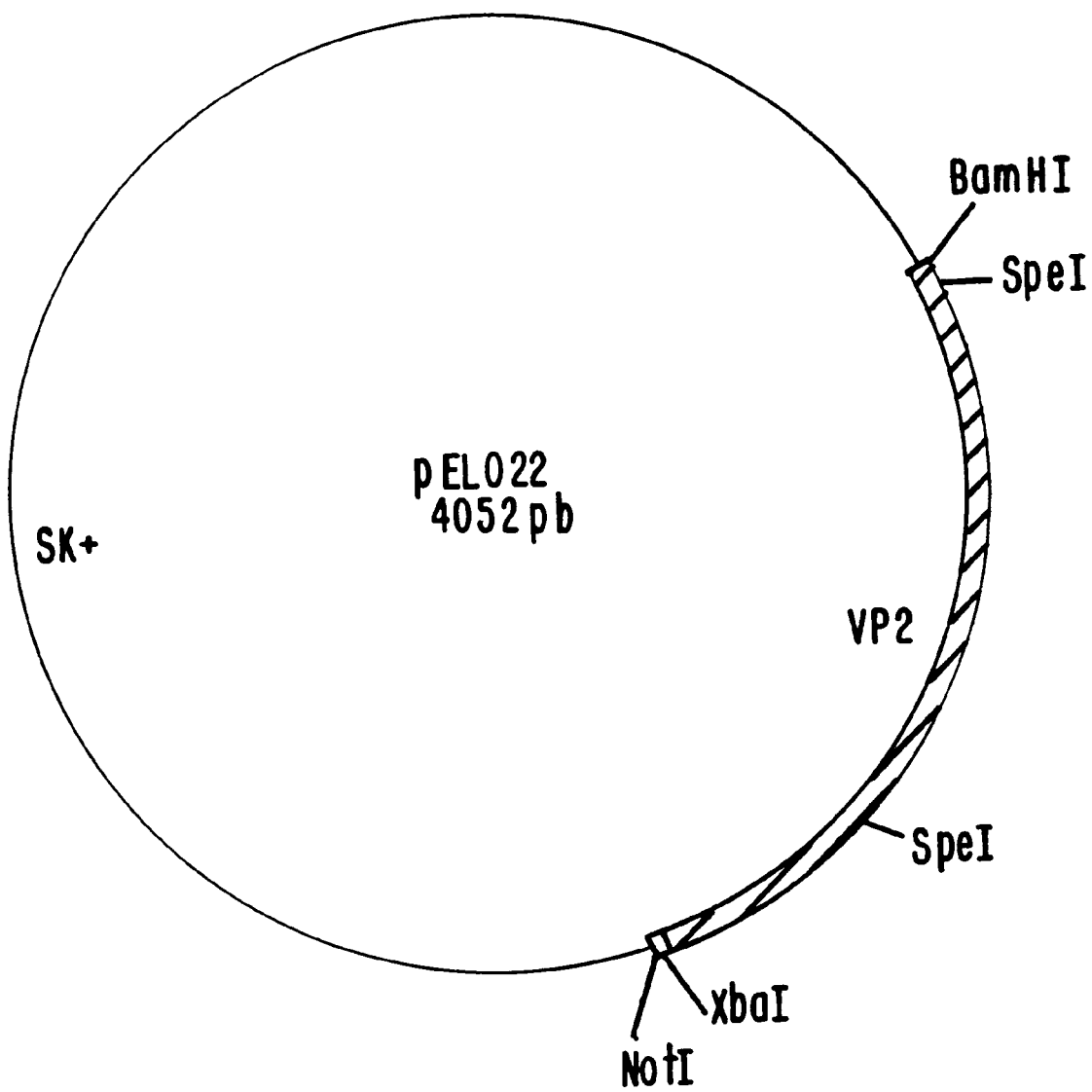
Figure 12:
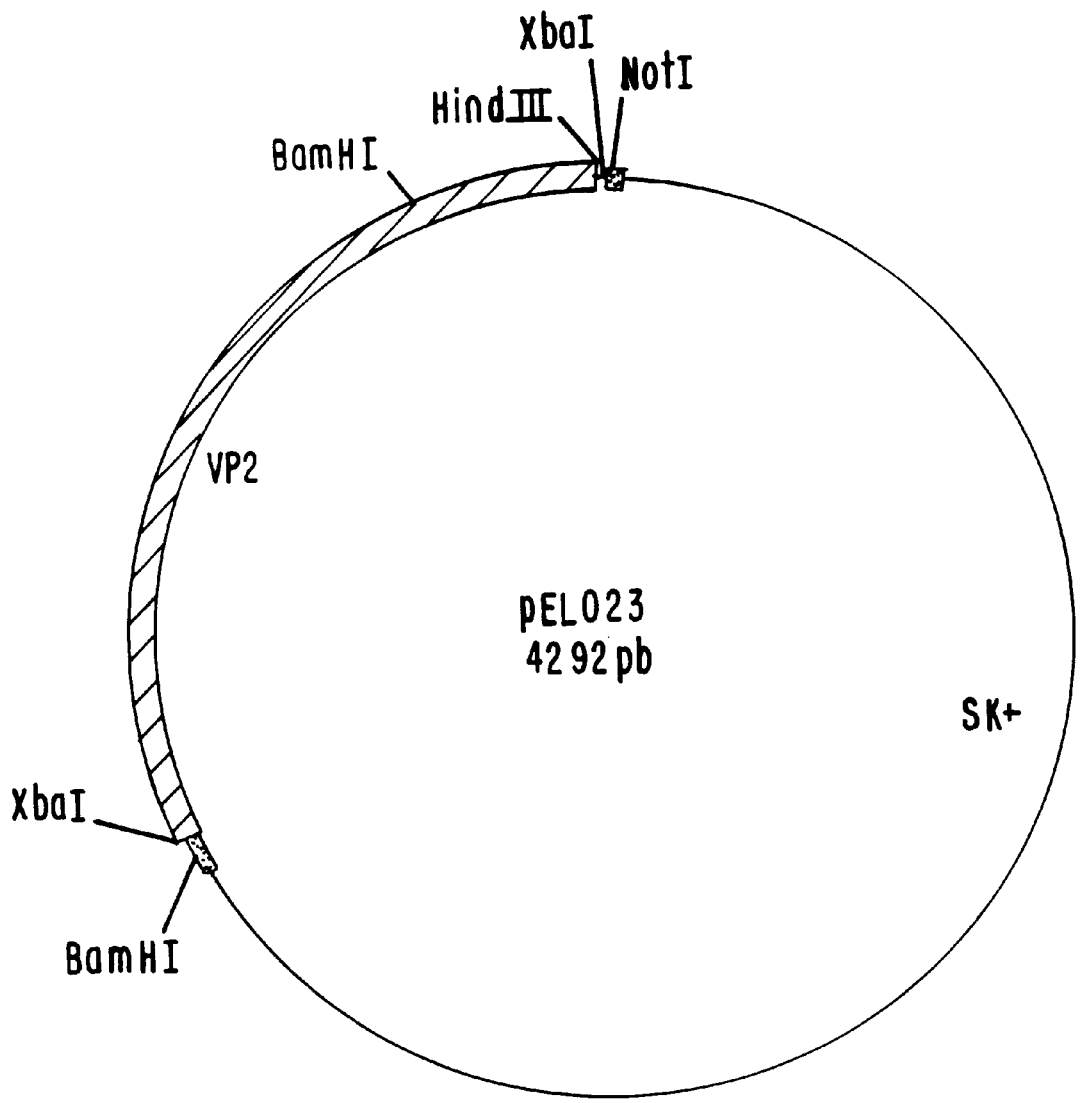
Figure 13:
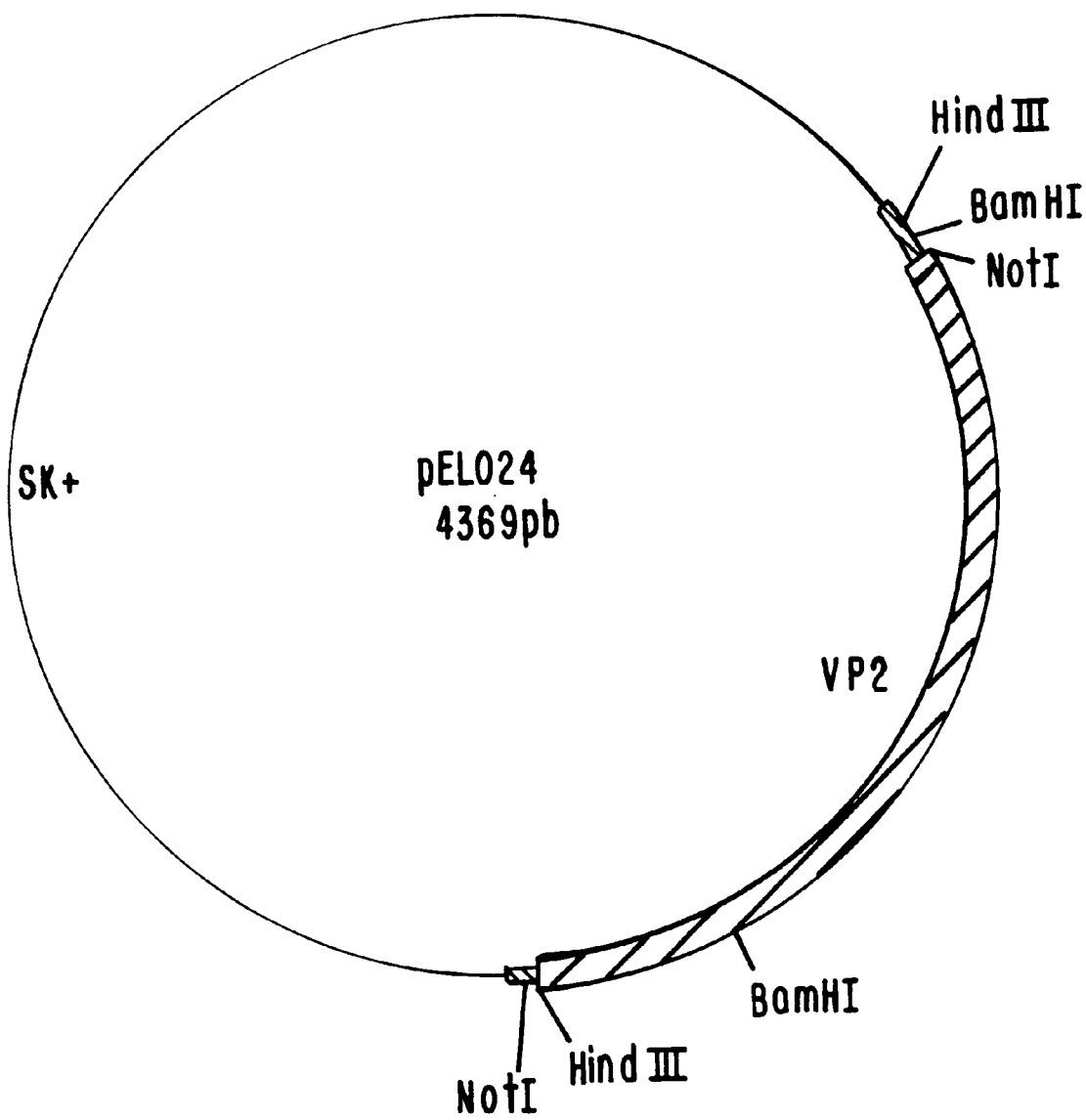
Figure 14:
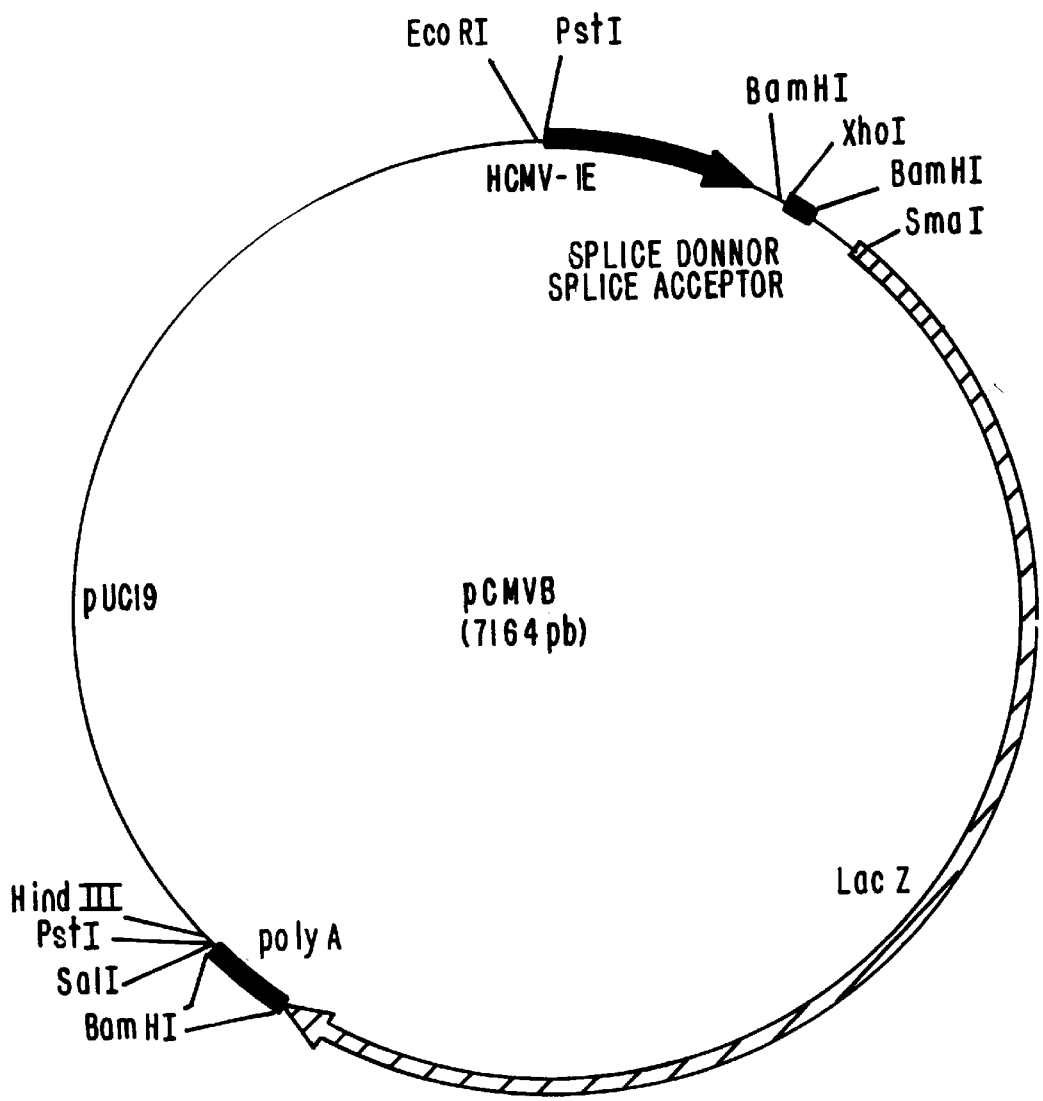
Figure 15:
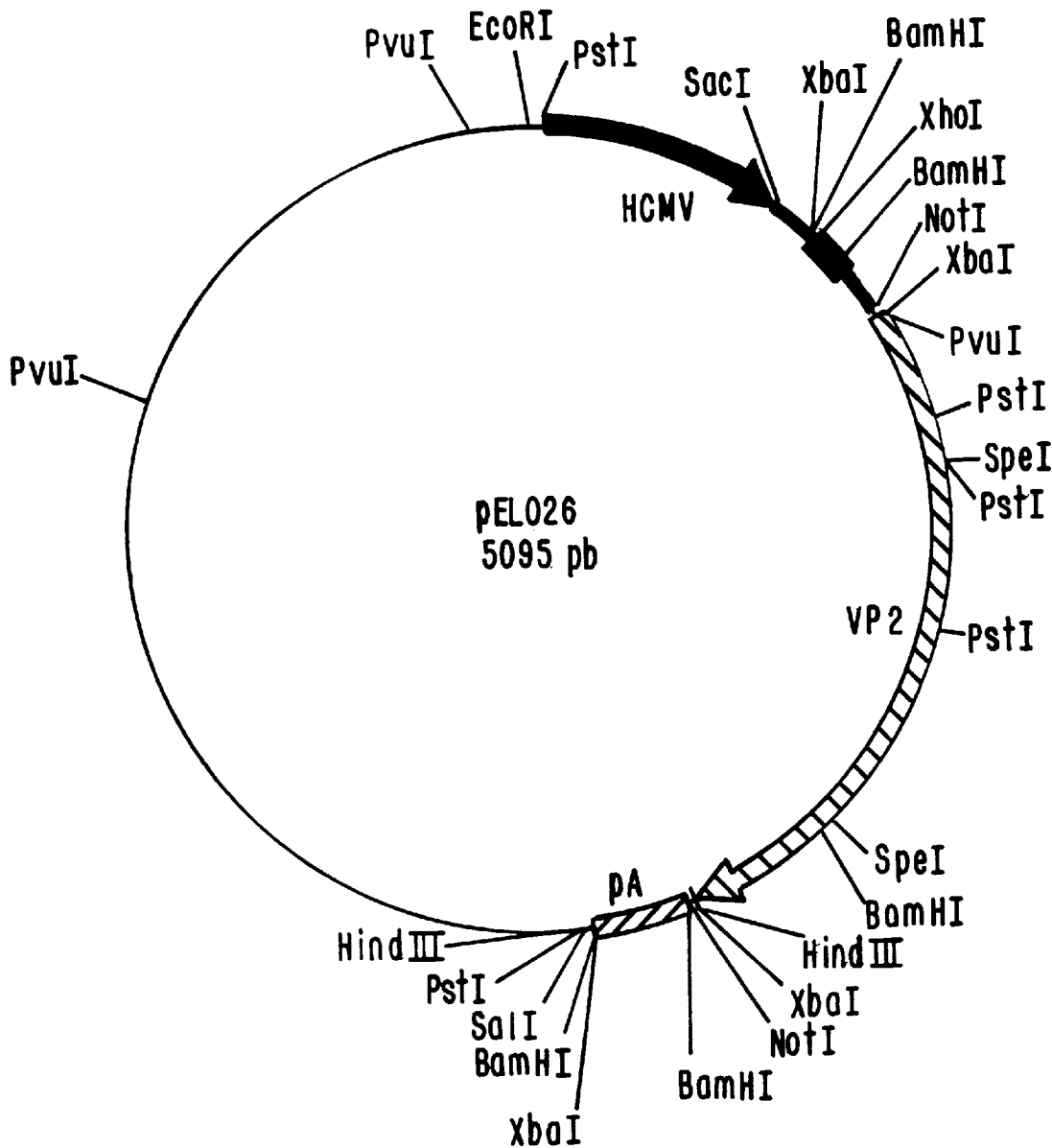
Figure 17:
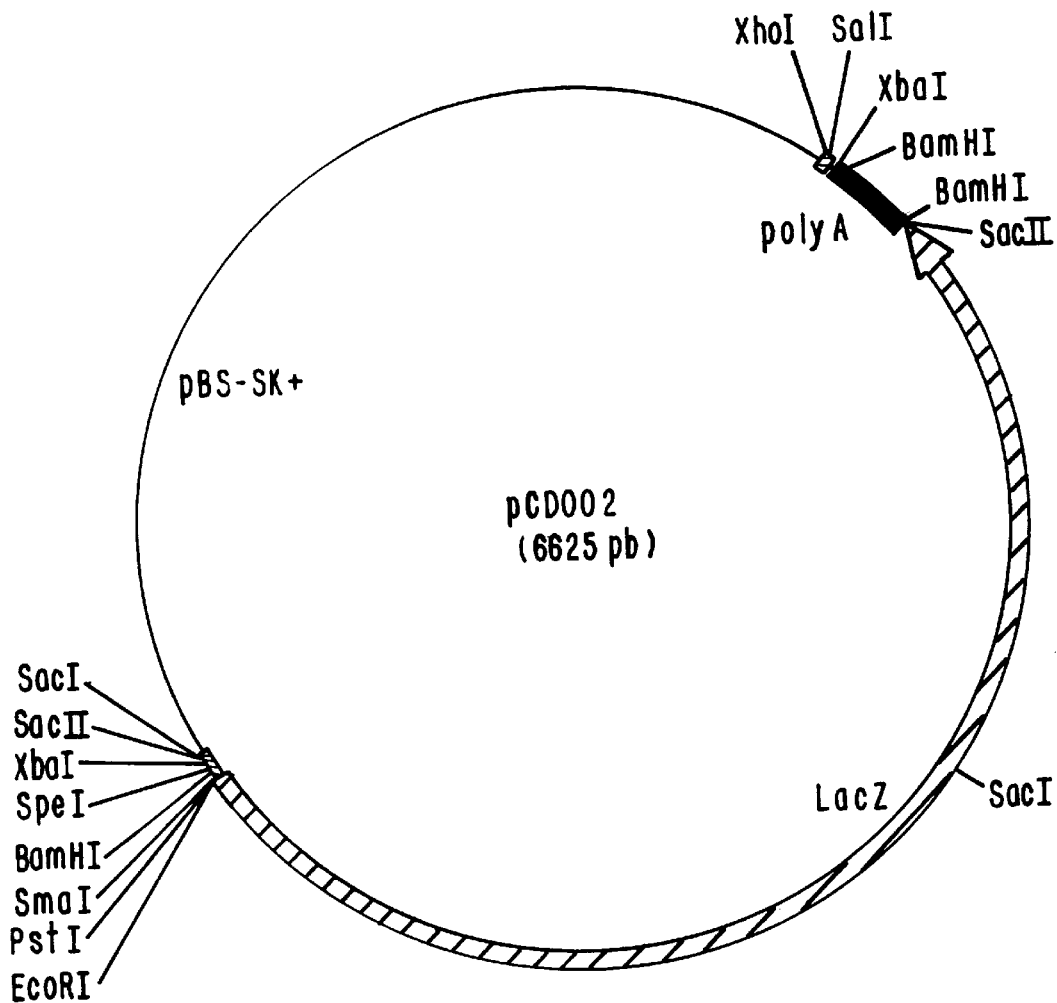
Figure 18:
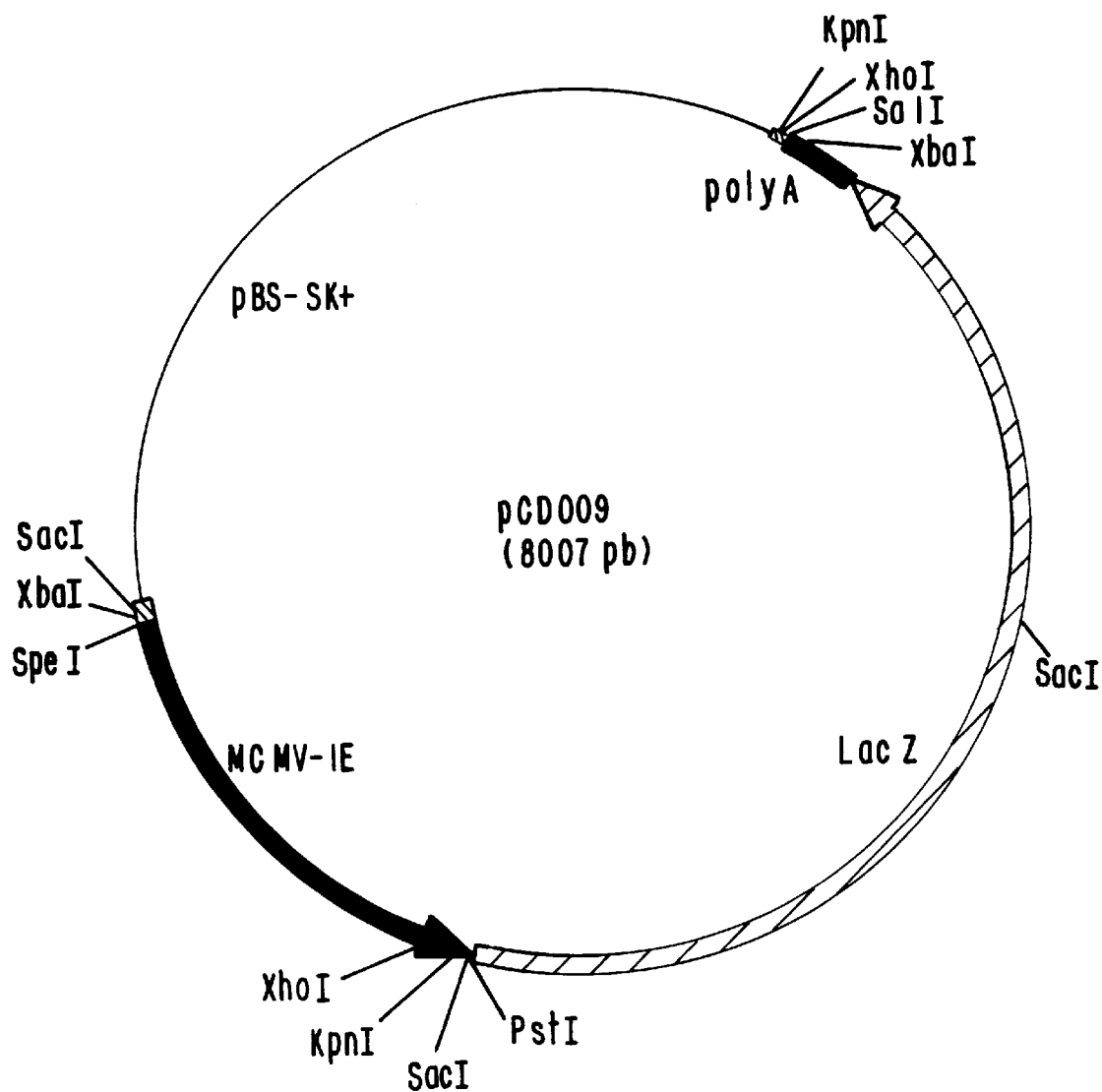
Figure 19:
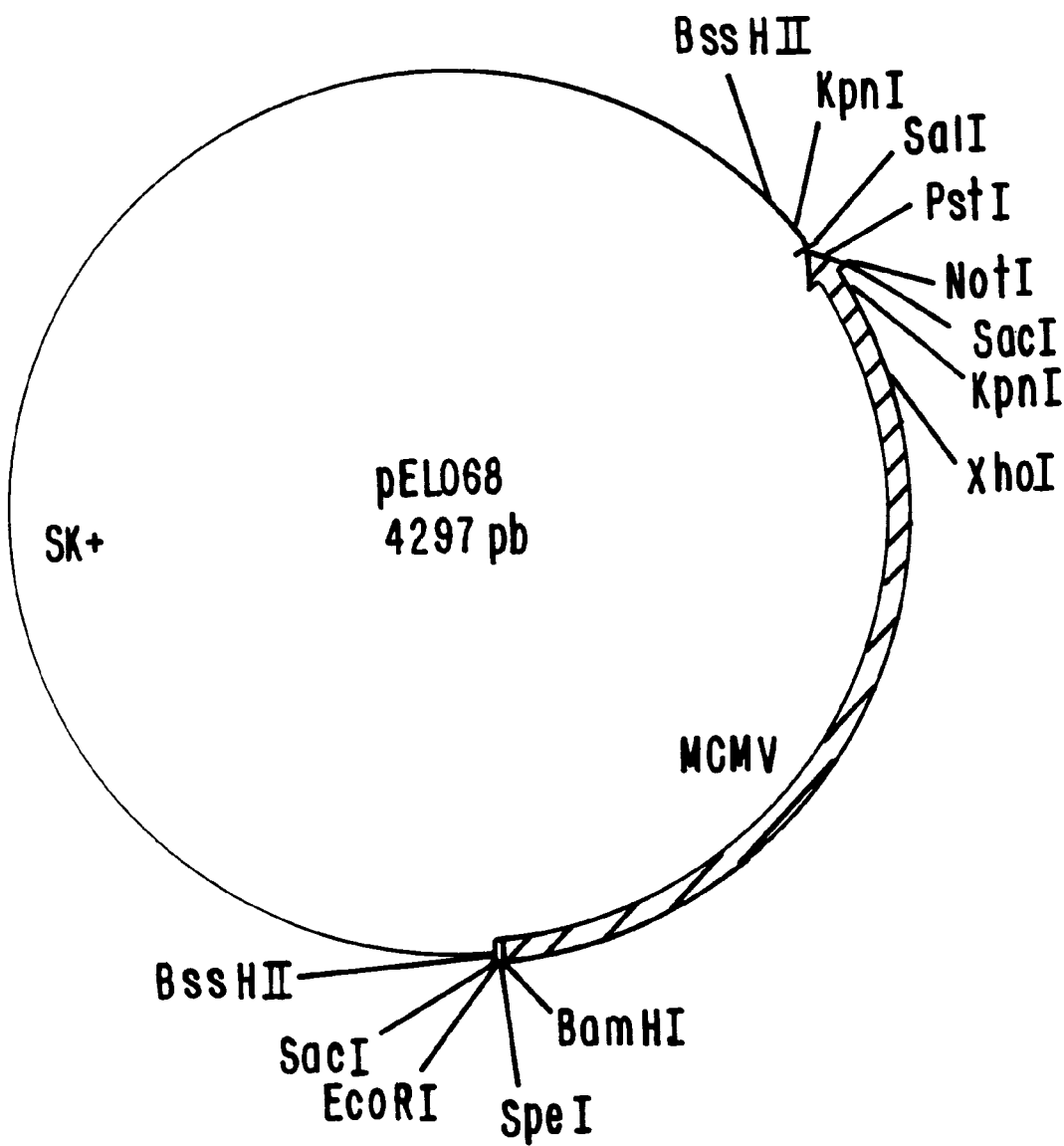
Figure 20:
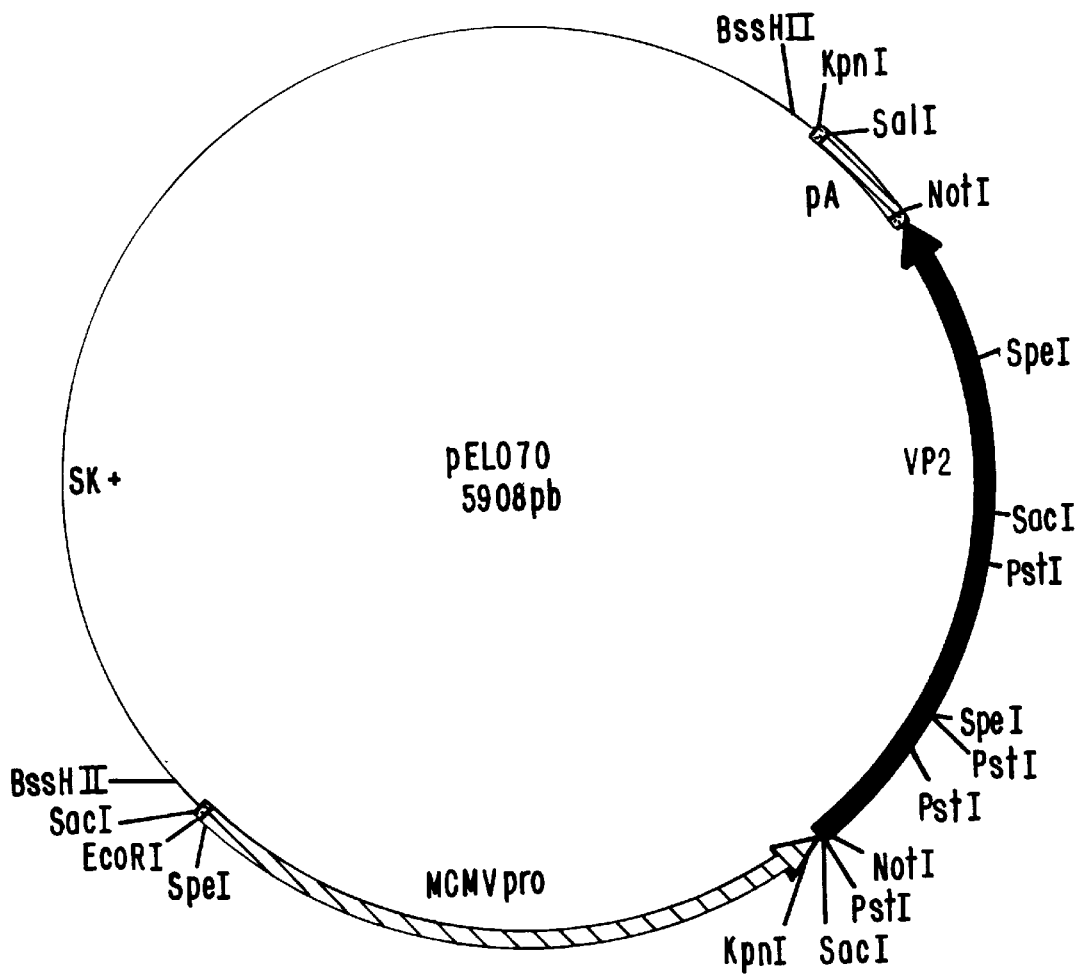
Figure 22:
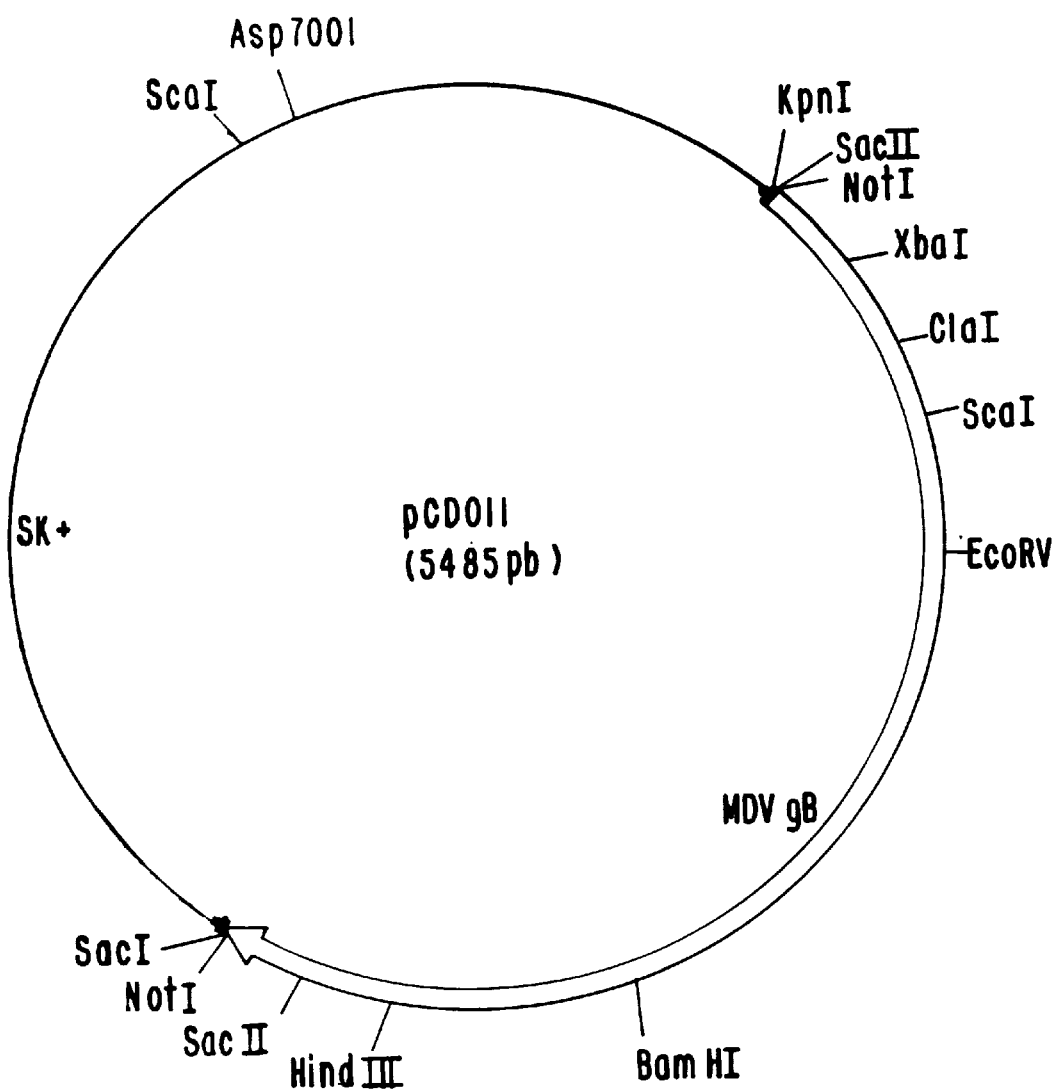
Figure 23:
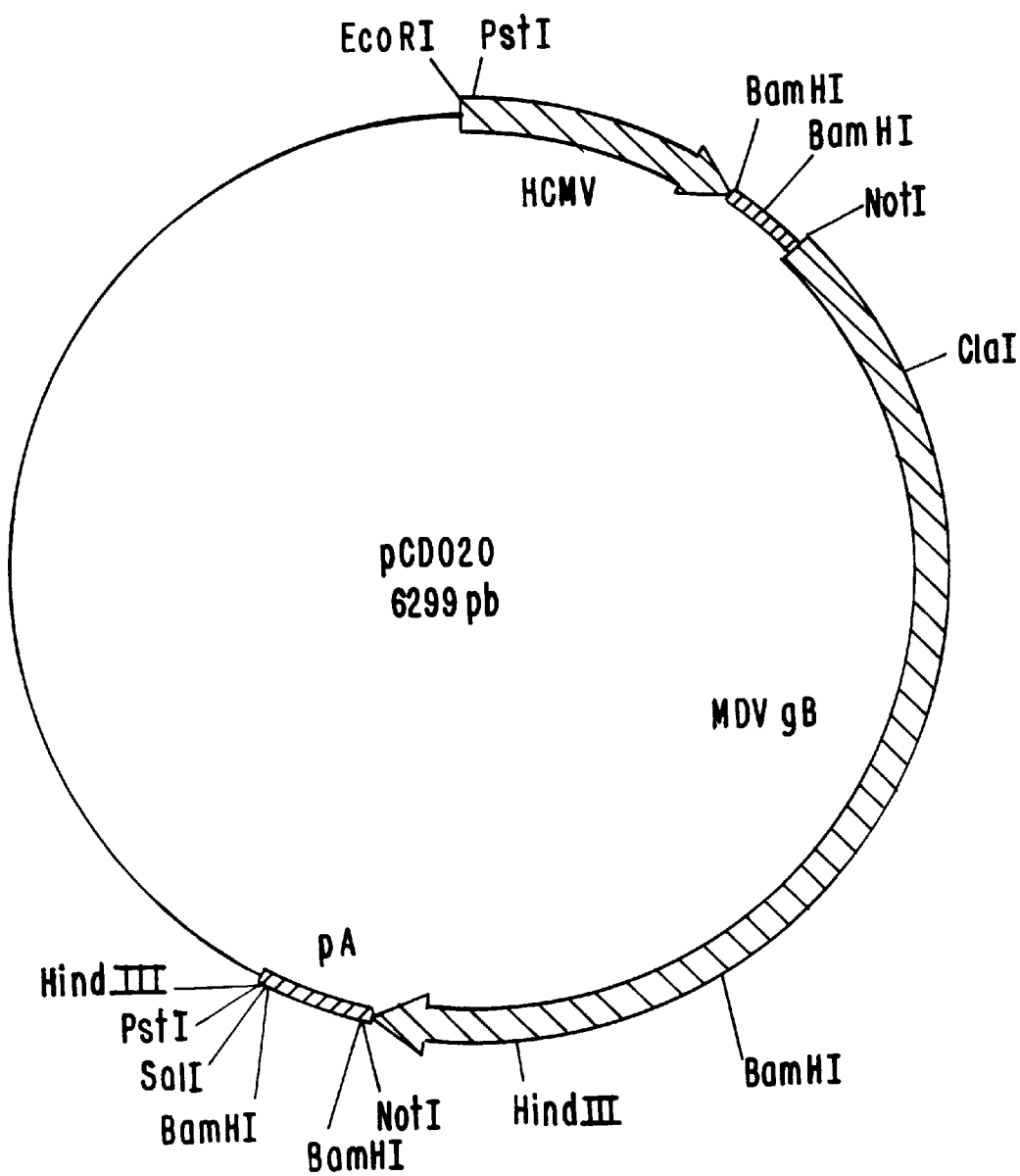
Figure 24:
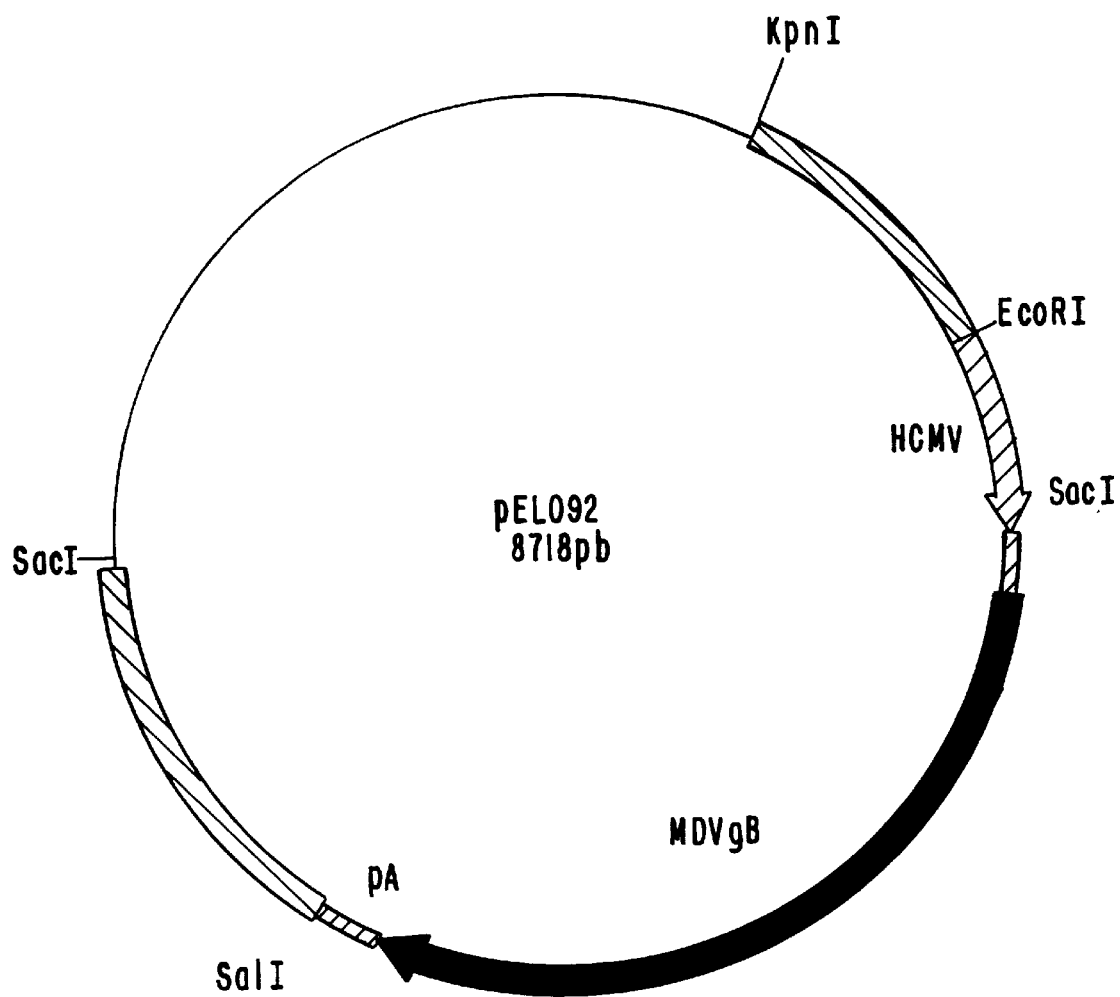
Figure 26:
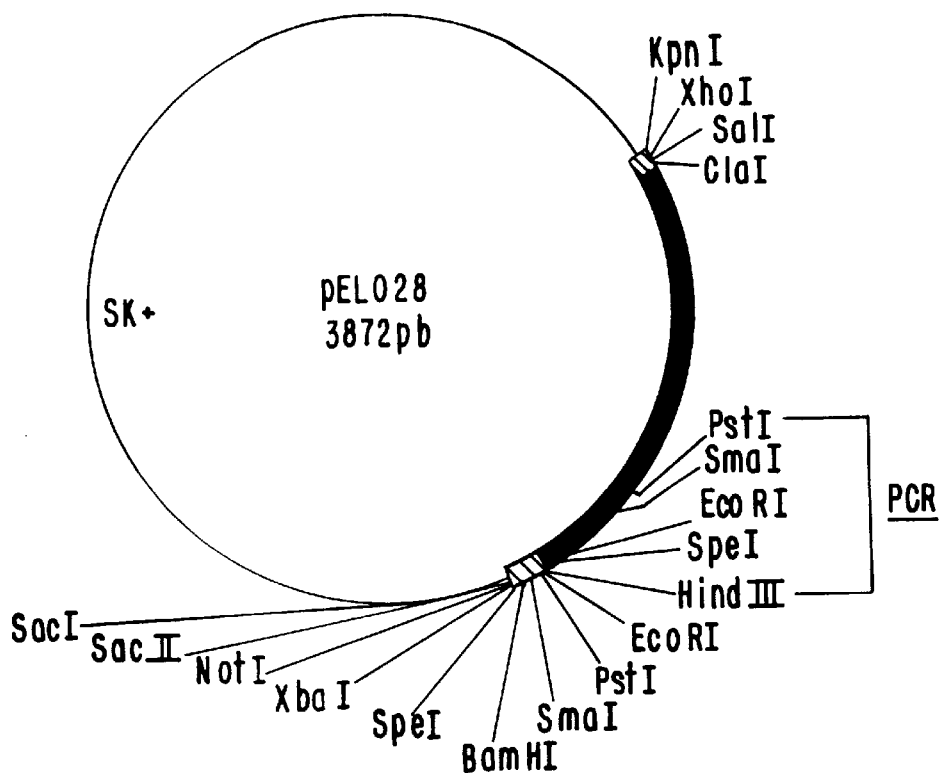
Figure 27:
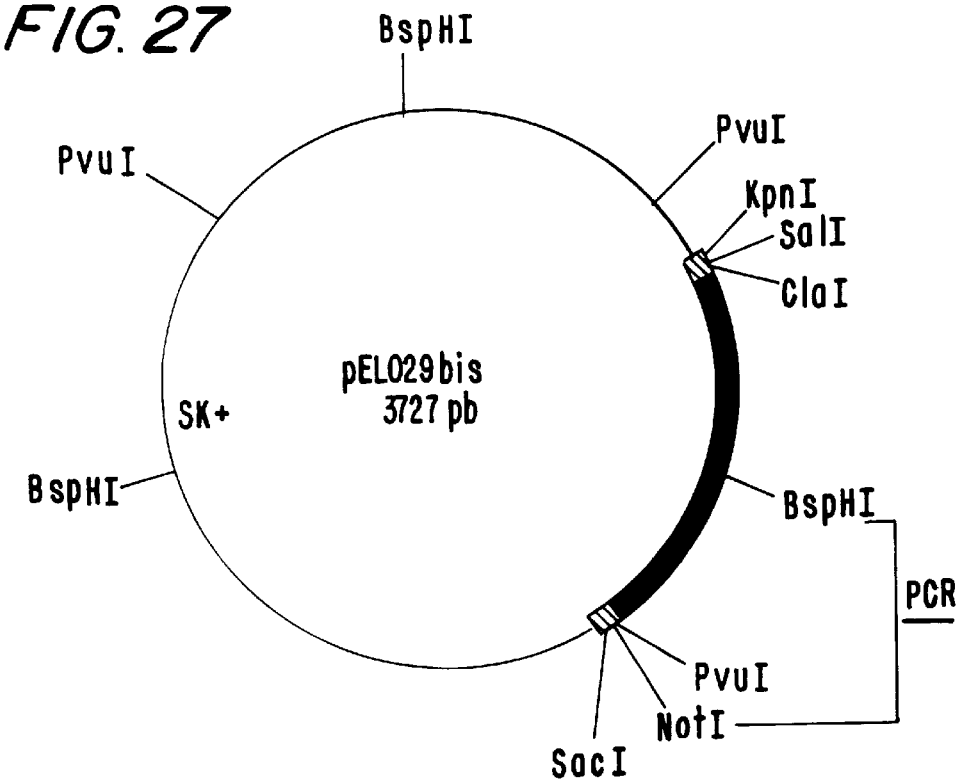
Figure 28:
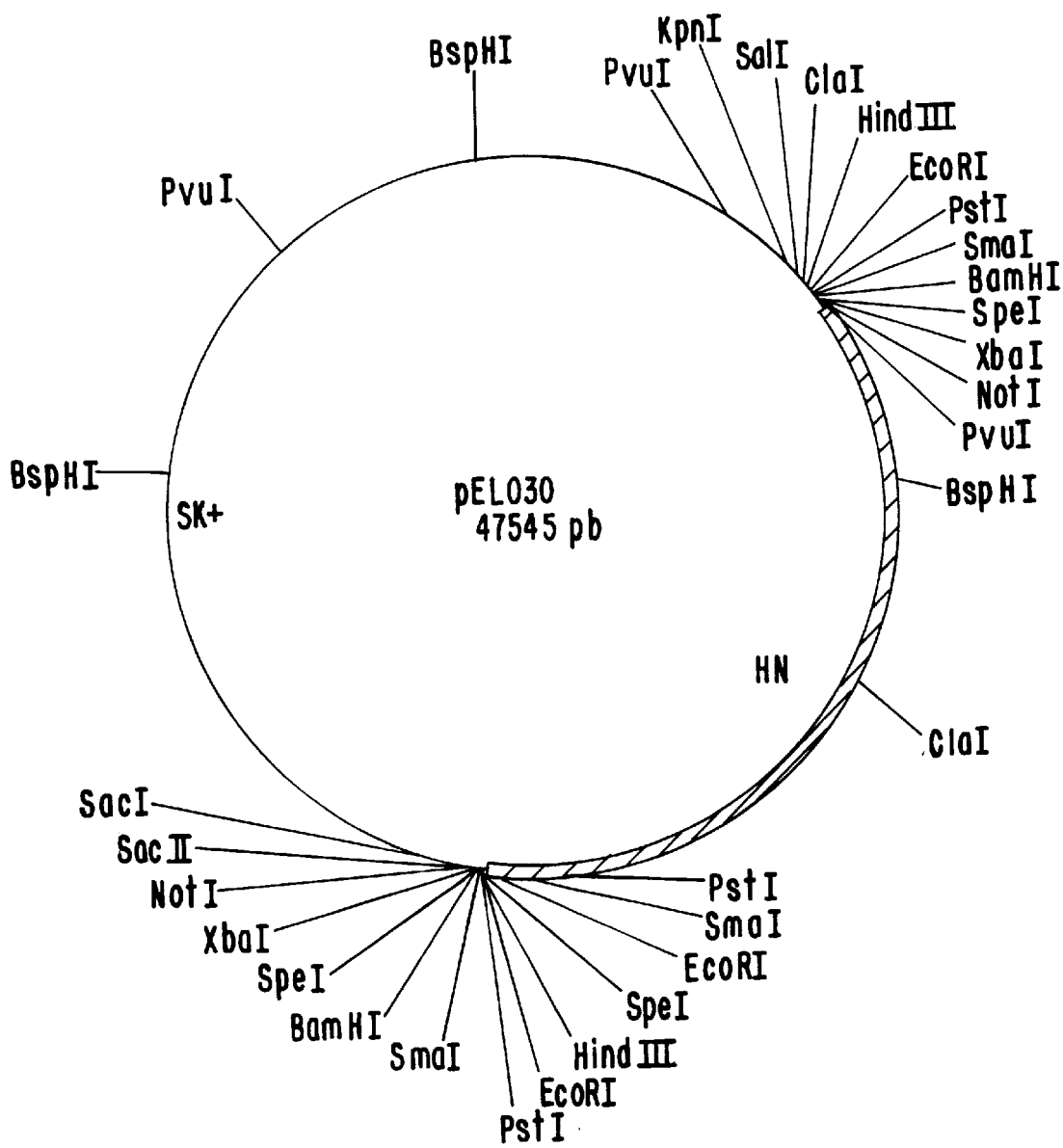
Figure 29:
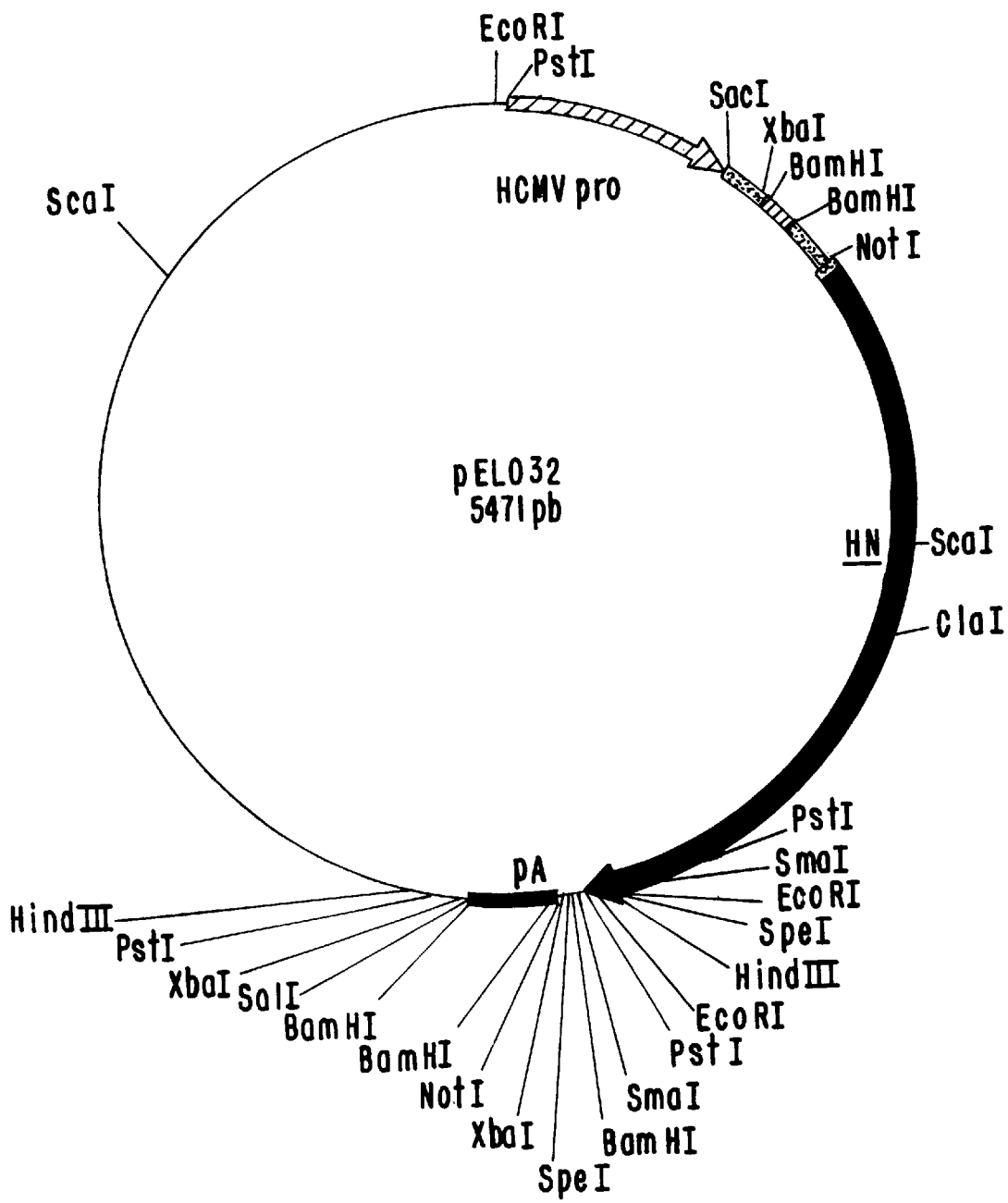
Figure 30:
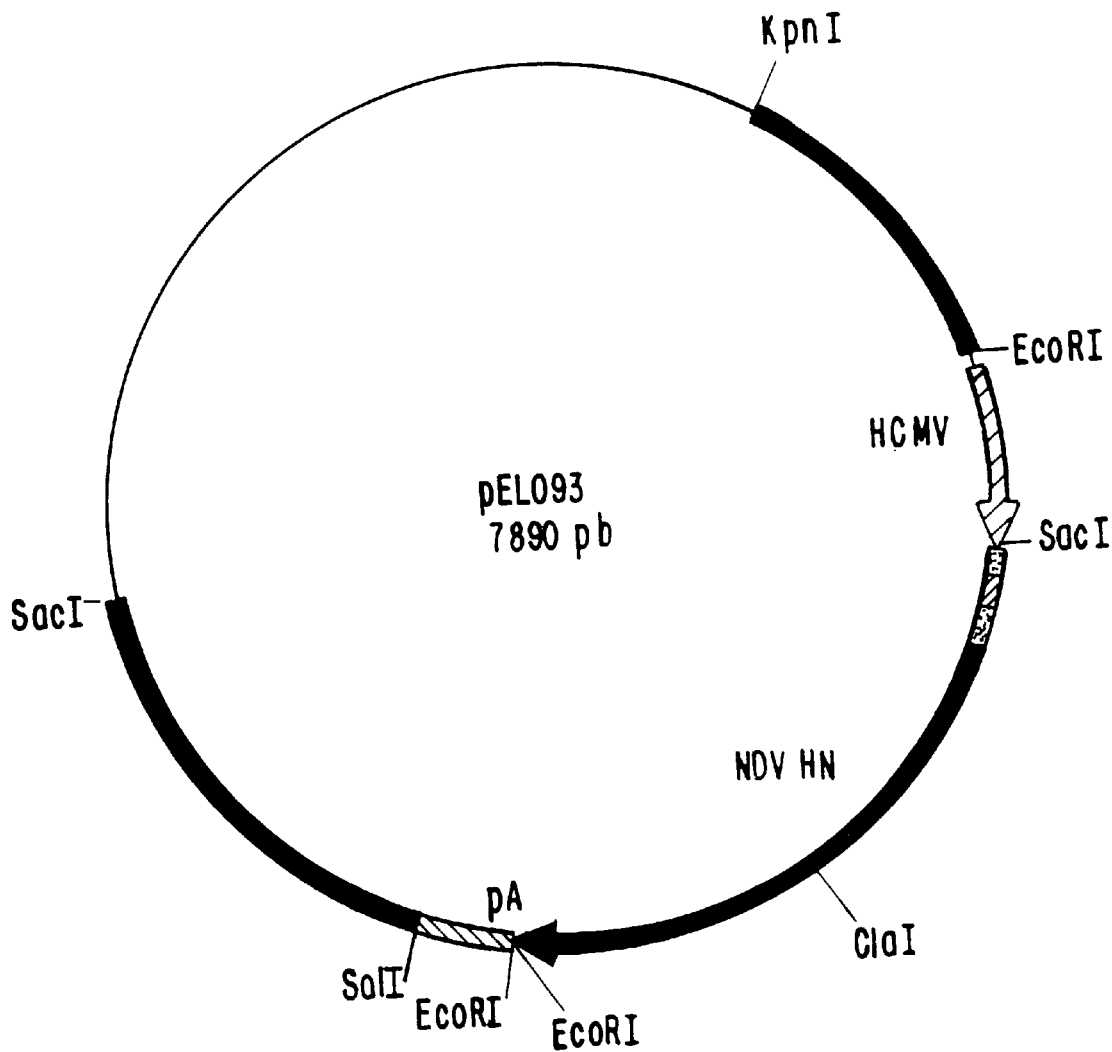
Figure 31:
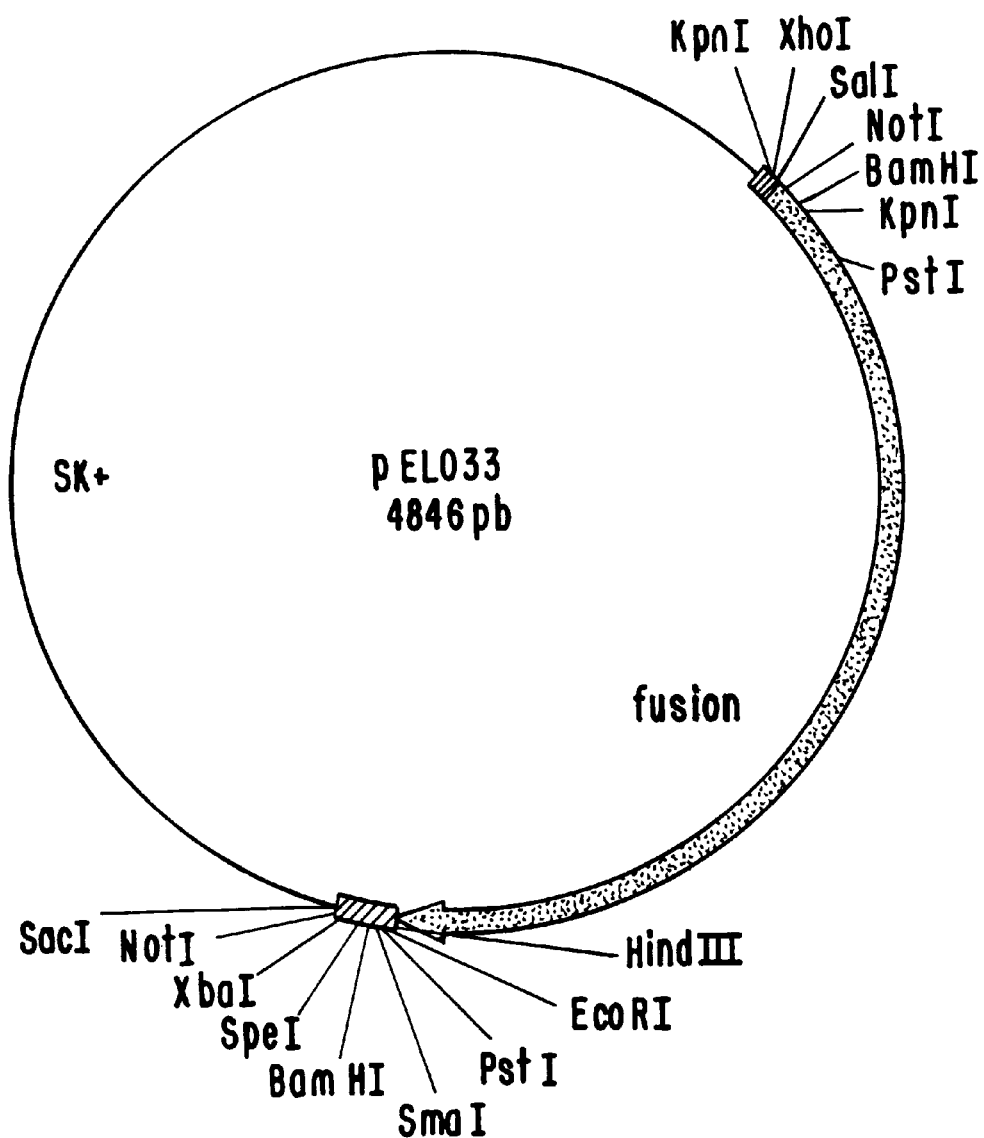
Figure 32:
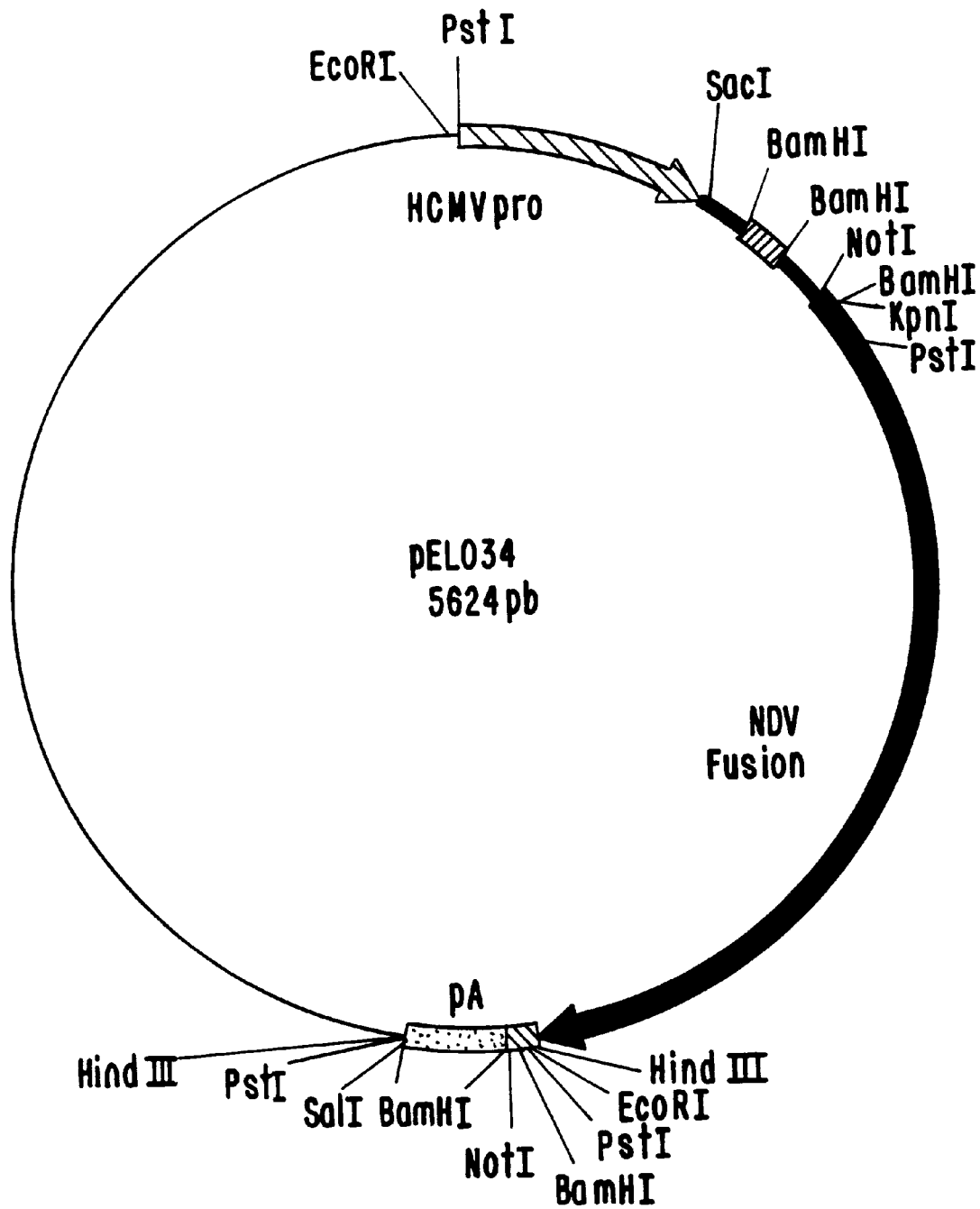
Figure 33:
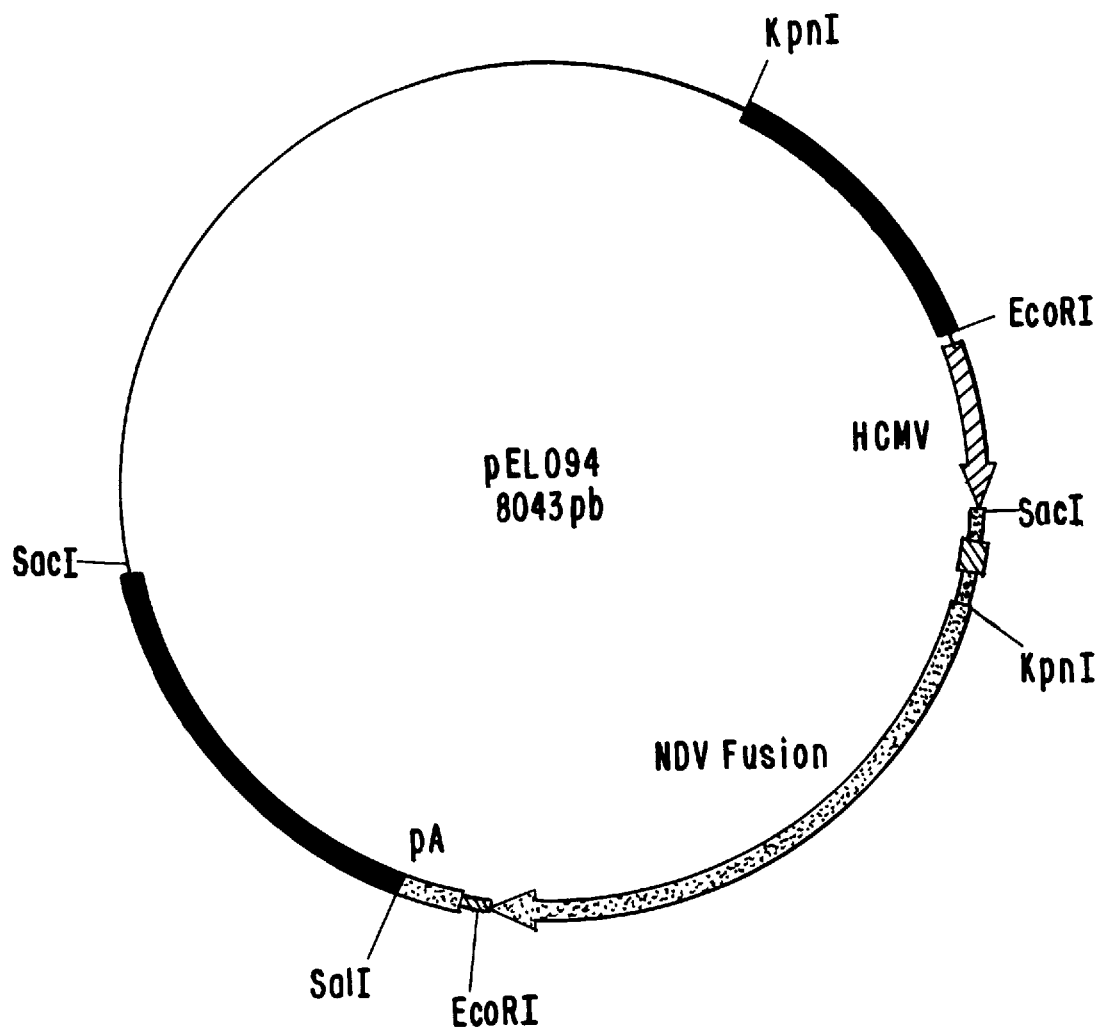
Figure 35:
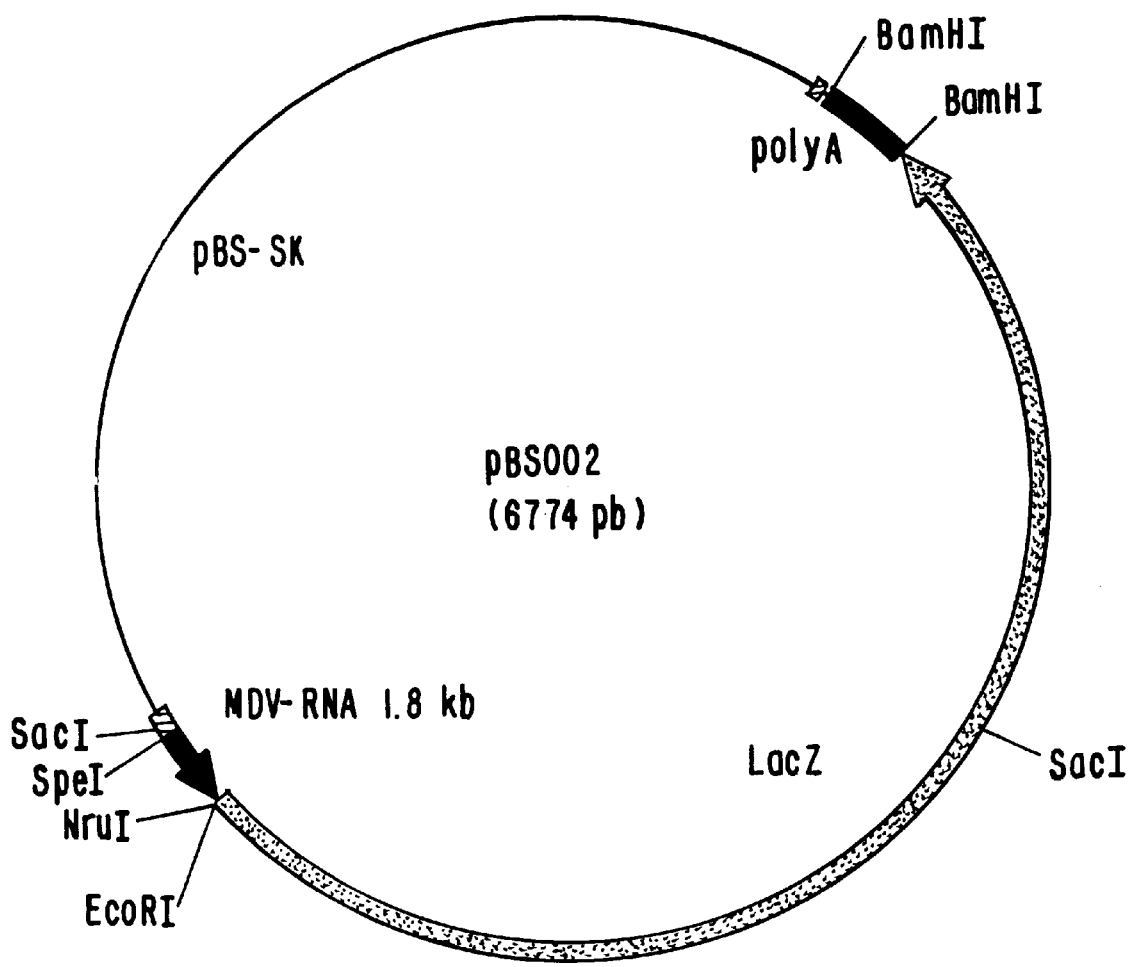
Figure 36:
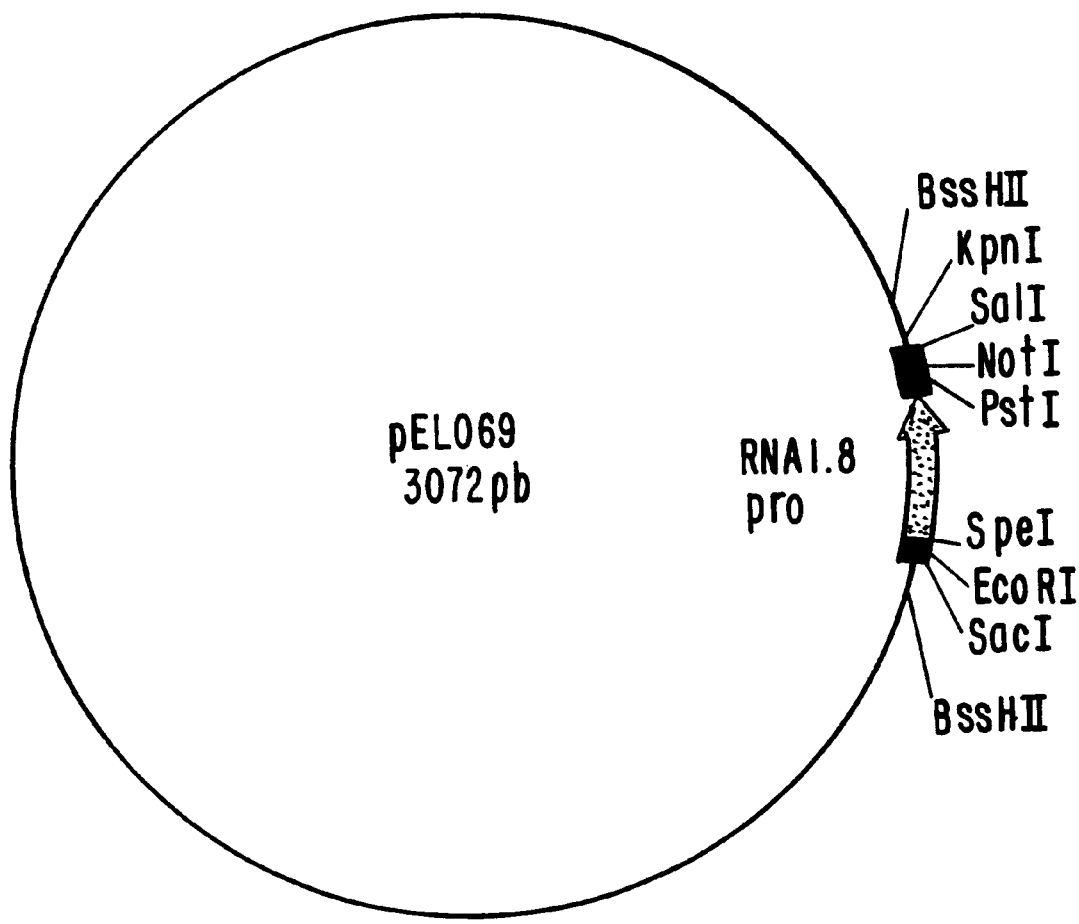

FIG. 1: Sequence of the HVT BamHI fragment I
FIG. 2: plasmid pEL039
FIG. 3: plasmid pEL077
FIG. 4: plasmid pEL079
FIG. 5: plasmid pEL076
FIG. 6: plasmid pEL078
FIG. 7: plasmid pEL054
FIG. 8: plasmid pEL055
FIG. 9: plasmid pEL062
FIG. 10: plasmid pEL066
FIG. 11: plasmid pEL022
FIG. 12: plasmid pEL023
FIG. 13: plasmid pEL024
FIG. 14: plasmid pCMVβ
FIG. 15: plasmid pEL026
FIG. 16: plasmid pEL090
FIG. 17: plasmid pCD002
FIG. 18: plasmid pCD009
FIG. 19: plasmid pEL068
FIG. 20: plasmid pEL070
FIG. 21: plasmid pEL091
FIG. 22: plasmid pCD011
FIG. 23: plasmid pCD020
FIG. 24: plasmid pEL092
FIG. 25: Sequence of the NDV HN gene
FIG. 26: plasmid pEL028
FIG. 27: plasmid pEL029bis
FIG. 28: plasmid pEL030
FIG. 29: plasmid pEL032
FIG. 30: plasmid pEL093
FIG. 31: plasmid pEL033
FIG. 32: plasmid pEL034
FIG. 33: plasmid pEL094
FIG. 34: Sequence of the MDV 1.8-kbp RNA promoter
FIG. 35: plasmid pBS002
FIG. 36: plasmid pEL069
FIG. 37: plasmid pEL080
FIG. 38: plasmid pEL081
FIG. 39: plasmid pEL095
FIG. 40: plasmid pEL098

SEQ ID sequence listing for the constructions in the intergenic sites

SEQ ID No. 1 Sequence of the HVT BamHI fragment I
SEQ ID No. 2 Oligonucleotide EL102
SEQ ID No. 3 Oligonucleotide EL161
SEQ ID No. 4 Oligonucleotide EL147
SEQ ID No. 5 Oligonucleotide EL162
SEQ ID No. 6 Oligonucleotide EL154
SEQ ID No. 7 Oligonucleotide EL163
SEQ ID No. 8 Oligonucleotide EL164
SEQ ID No. 9 Oligonucleotide EL165
SEQ ID No. 10 Oligonucleotide EL132
SEQ ID No. 11 Oligonucleotide EL133
SEQ ID No. 12 Oligonucleotide MB070
SEQ ID No. 13 Oligonucleotide MB071
SEQ ID No. 14 Oligonucleotide CD001
SEQ ID No. 15 Oligonucleotide CD002
SEQ ID No. 16 Oligonucleotide CD003

SEQ ID No. 17 Oligonucleotide CD004
SEQ ID No. 18 Sequence of the NDV HN gene
SEQ ID No. 19 Oligonucleotide EL071
SEQ ID No. 20 Oligonucleotide EL073
SEQ ID No. 21 Oligonucleotide EL074
SEQ ID No. 22 Oligonucleotide EL075
SEQ ID No. 23 Oligonucleotide EL076
SEQ ID No. 24 Oligonucleotide EL077
SEQ ID No. 25 Sequence of the MDV 1.8-kbp RNA promoter
SEQ ID No. 26 Oligonucleotide MB047
SEQ ID No. 27 Oligonucleotide MB048
SEQ ID No. 28 Oligonucleotide MB072

EXAMPLES

All the plasmid constructions were carried out using the standard techniques of molecular biology described by Sambrook J. et al. (*Molecular Cloning: A Laboratory Manual.* 2nd Edition. Cold Spring Harbor Laboratory. Cold Spring Harbor. N.Y. 1989). All the restriction fragments used for the present invention were isolated using the "Geneclean" kit (BIO 101 Inc. La Jolla, Calif.).

The virus used as parent virus is herpesvirus of turkeys (HVT) strain FC126, isolated by Dr. Witter of the Regional Poultry Research Laboratory (USDA, East Lansing, Mich.) in a flock of 23-week-old turkeys (Witter R. L. et al. Am. J. Vet. Res. 1970. 31. 525–538). The conditions of culture of this virus are those described elsewhere (French Patent Application 90/03105).

Example 1

Extraction of the DNA From Marek's Disease Virus

The whole blood of a chicken challenged at 7 days with MDV strain RB1B is harvested with a syringe onto anticoagulant (heparin solution at a concentration of 100 IU/ml) 14 days after infection. This blood is then centrifuged at 30 g for 15 minutes at room temperature. The plasma together with the buffy coat is removed and diluted in sterile PBS to have a final volume of 10 ml. After centrifugation for 15 minutes at 150 g, the cell pellet is resuspended in 2 ml of 199 culture medium (Gibco-BRL Cat# 042-01183M) containing 2% of foetal calf serum (FCS).

The total DNA of the infected lymphocytes is then extracted according to the technique described by R. Morgan et al. (Avian Diseases. 1990. 34. 345–351), and may be used directly as template for the PCR experiments. For the cloning of genomic fragments of the MDV virus, the strain RB1B was cultured on CEF and the viral DNA was prepared from purified viral particles as described by Lee Y. et al. (J. Gen. Virol. 1980. 51. 245–253).

Example 2

Preparation of MCMV Virus (Mouse Cytomegalovirus) Genomic DNA

MCMV virus strain Smith was obtained from the American Type Culture Collection, Rockville, Md., U.S.A. (ATCC No. VR-194). This virus was cultured on Balb/C mouse embryo cells and the viral DNA of this virus was prepared as described by Ebeling A. et al. (J. Virol. 1983. 47. 421–433).

Example 3

Preparation of HVT Virus Genomic DNA For the Transfection Experiments

The viral DNA used for the transfection experiments was prepared according to the technique described by R. Morgan et al. (Avian Diseases. 1990. 34. 345–351) from a culture of secondary CEC (CEC II) infected with HVT virus strain FC126.

Example 4

Description of the BamHI Fragment I

The 5.8-kbp BamHI fragment I of HVT virus strain FC126 (Igarashi T. et al. J. Gen. Virol. 1989. 70. 1789–1804) was isolated by Geneclean and cloned into the BamHI site of the vector pBS-SK+ to give the plasmid pEL037. The sequence of this fragment was established in its entirety (5838 bp) (FIG. 1 and SEQ ID No. 1). 6 open reading frames (ORFs) were identified on this sequence. A study of the proteins potentially encoded by these ORFs revealed that some of these proteins displayed a homology with proteins encoded by ORFs present in other alpha-herpesviruses. The first ORF (ORF1) (position 676 to position 1209 on SEQ ID No. 1) displays a homology with the ORFs HSV-1 UL55, EHV-1 gene 4 and VZV gene 5, and codes for a theoretical protein HVT UL55 of 178 amino acids (aa). ORF 2 is located from position 1941 to position 1387 on the sequence SEQ ID No. 1 and codes for a protein of 185 aa homologous with the protein encoded by the ORF EHV-1 gene 3. ORF 3 is incomplete. It is located from position 5838 to 3573 on SEQ ID No. 1 and displays a homology with ORF 21 of MDV (Ross No. et al. Virus Genes. 1993. 7. 33–51). Three other ORFs identified on this sequence, namely ORF4 (position 1403 to position 1957 (protein of 185 aa)), ORF5 (position 3081 to position 2287 (protein of 265 aa)), and ORF6 (incomplete; position 479 to position 1), do not have homologues in the sequence libraries. The genomic organization of the BamHI fragment I of HVT virus strain FC126 is such that there are 3 intergenic regions which may be used as insertion sites for cassettes for the expression of foreign genes:

An intergenic region (intergenic region 1) exists between ORF UL55 and ORF HVT gene 3. A second intergenic region (intergenic region 2) exists between ORF HVT gene 3 and the 265-aa ORF. A third intergenic region (intergenic region 3) exists between the 265-aa ORF and ORF 21. These three regions are useable for inserting expression cassettes without affecting the in vivo replication of the recombinant HVT viruses thereby obtained. Examples of constructions of donor plasmids for these intergenic regions 1, 2 and 3 are described below:

Example 5

Construction of the Donor Plasmid For Intergenic Region 1

Figure 3:
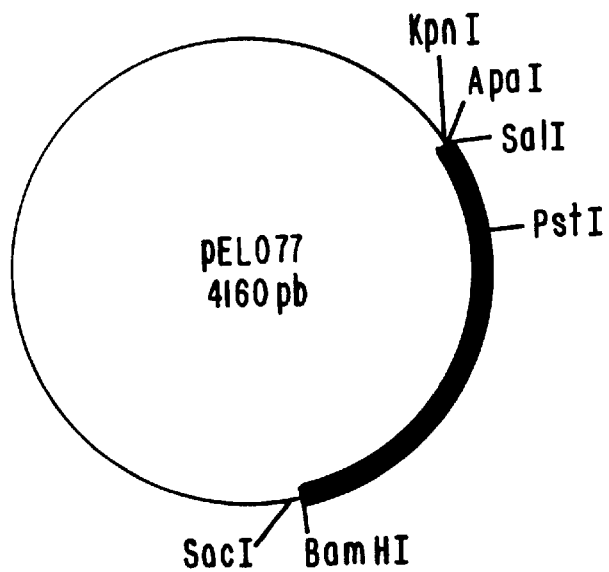
Figure 4:
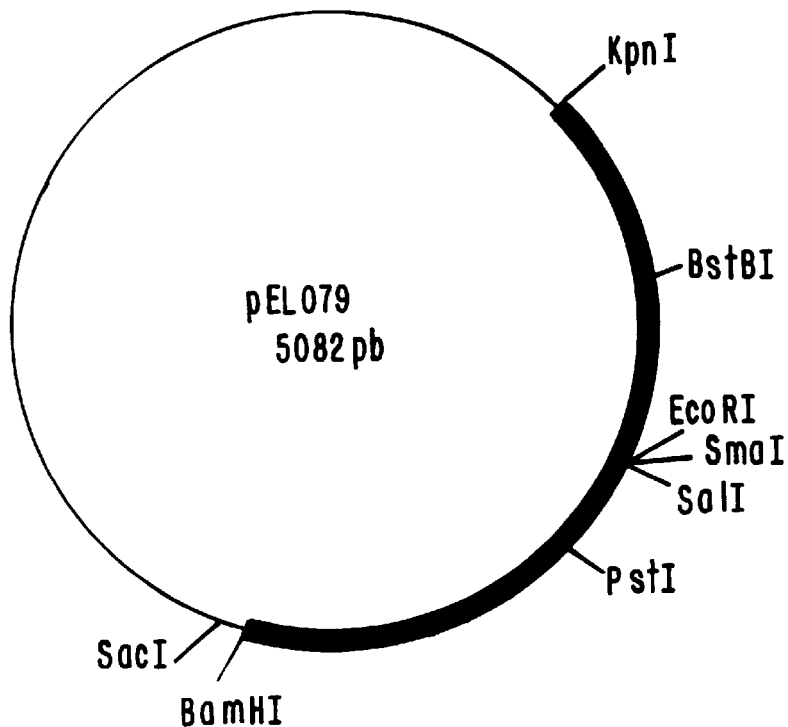

Plasmid pEL037 was digested with BamHI and EcoRI to isolate 2672-bp and 2163-bp BamHI-EcoRI fragments. These fragments were ligated with the vector pBS-SK+, previously digested with BamHI and EcoRI, to give, respectively, the plasmids pEL039 of 5167 bp and pEL040 of 6104 bp. Plasmid pEL039 (FIG. 2) was digested with BamHI and PstI to isolate the 997-bp BamHI-PstI fragment (fragment A). A PCR was carried out with the following oligonucleotides:
EL102 (SEQ ID No. 2) 5' CATTATAAGACCAACGTGC-GAGTC 3'
EL161 (SEQ ID No. 3) 5' GTTCACGTCGACAATTATTT-TATTTAATAAC 3'
and the template pEL039 to produce a 420-bp fragment. This fragment was digested with PstI and SalI to isolate a 250-bp PstI-SalI fragment (fragment B). Fragments A and B were ligated together with the vector pBSII-SK+ (Stratagene), previously digested with BamHI and SalI, to give the 4160-bp plasmid pEL077 (FIG. 3). Plasmid pEL039 was digested with BstBI and ScaI to isolate a (blunt-ended) 475-bp BstBI-ScaI fragment (fragment C). A PCR was carried out with the following oligonucleotides:
EL147 (SEQ ID No. 4) 5' AAGATAATGGGCTCCCGCTGTTC 3'
EL162 (SEQ ID No. 5) 5' TAATTGTCGACCCCGGGGAATTCGTTTAATGTTAGTTTATTC 3'
and the template pEL039 to produce a 715-bp PCR fragment. This fragment was digested with BstBI and SalI to isolate the 465-bp BstBI-SalI fragment (fragment D). Fragments C and D were ligated together with plasmid pEL077, previously digested with ApaI and repaired with Klenow polymerase and digested with SalI, to give the 5082-bp plasmid pEL079 (FIG. 4). This plasmid contains an EcoRI-SmaI-SalI polylinker in intergenic site 1.

Example 6

Construction of the Donor Plasmid For Intergenic Region 2

Figure 5:
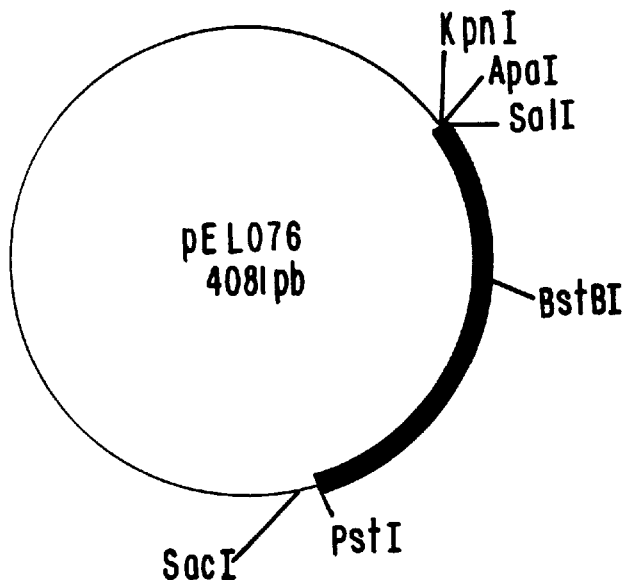
Figure 6:
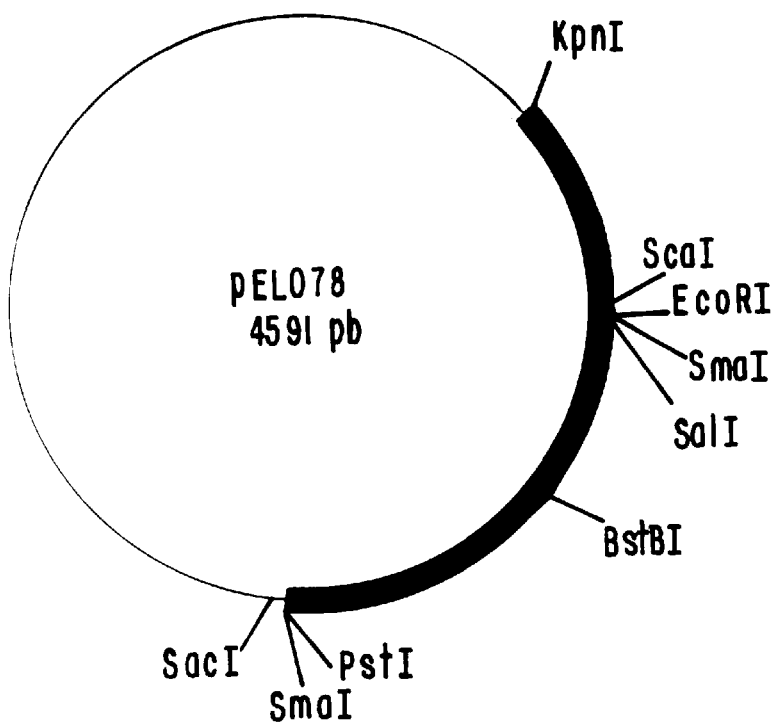

Plasmid pEL039 (Example 5) was digested with BstBI and PstI to isolate the 715-bp BstBI-PstI fragment (fragment A). A PCR was carried out with the following oligonucleotides:
EL154 (SEQ ID No. 6) 5' GAAATGCAAACTAACATTATTGTC 3'
EL163 (SEQ ID No. 7) 5' GTGTAAATAGTCGACAATATAGATAACGGGC 3'
and the template pEL039 to produce a 500-bp PCR fragment. This fragment was digested with BstBI and SalI to isolate the 430-bp BstBI-SalI fragment (fragment B). Fragments A and B were ligated together with the vector pBSII-SK+, previously digested with PstI and SalI, to give the 4081-bp plasmid pEL076 (FIG. 5).
Another PCR was carried out with the following oligonucleotides:
EL164 (SEQ ID No. 8) 5' CTATATTGTCGACCCCGGGGAATTCATCGACATGATTAAATAC 3'
EL165 (SEQ ID No. 9) 5' CAATGAAGAAATATTTTCTTTGTTCCTTGAAATGC 3'
and the template pEL039 to produce a 565-bp PCR fragment. This fragment was digested with SalI and SspI to isolate the 535-bp SalI-SspI fragment. This fragment was ligated with plasmid pEL076, previously digested with ApaI and repaired with Klenow polymerase and digested with SalI, to give the 4598-bp plasmid pEL078 (FIG. 6). This plasmid contains an EcoRI-SmaI-SalI polylinker in intergenic region 2.

Example 7

Construction of the Donor Plasmid For Intergenic Region 3

Figure 8:
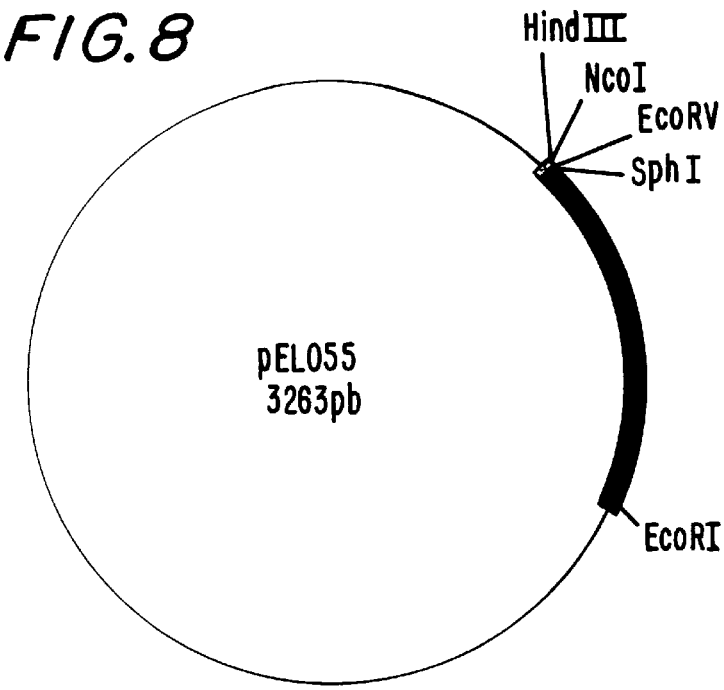
Figure 7:
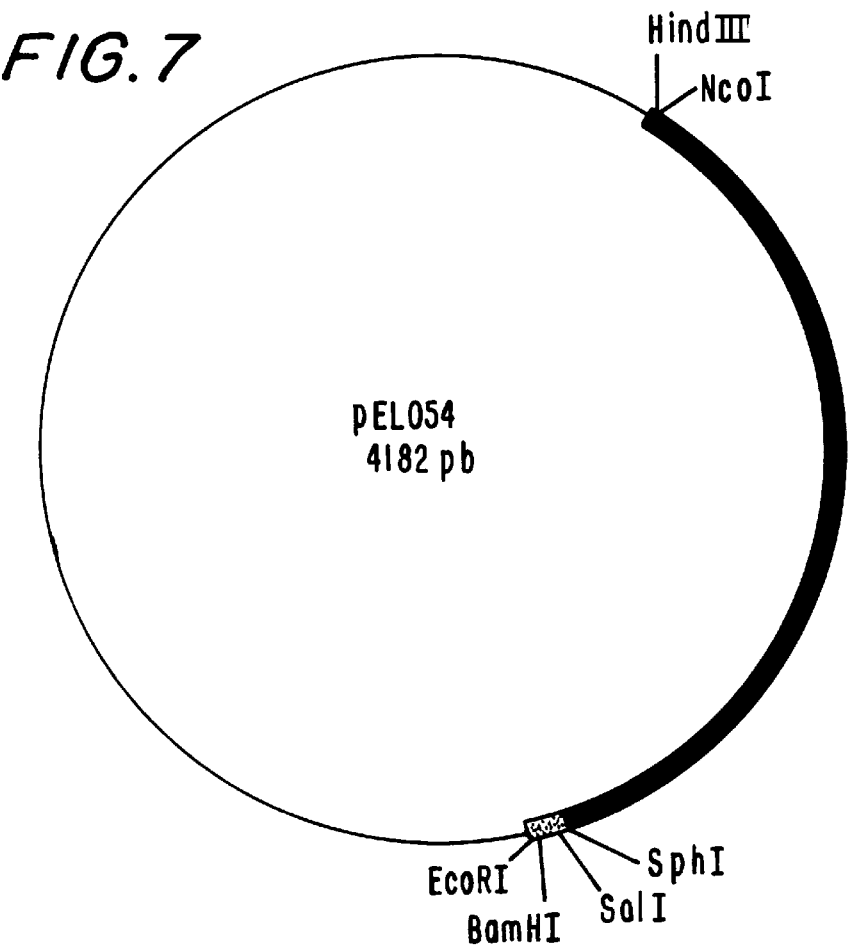
Figure 9:
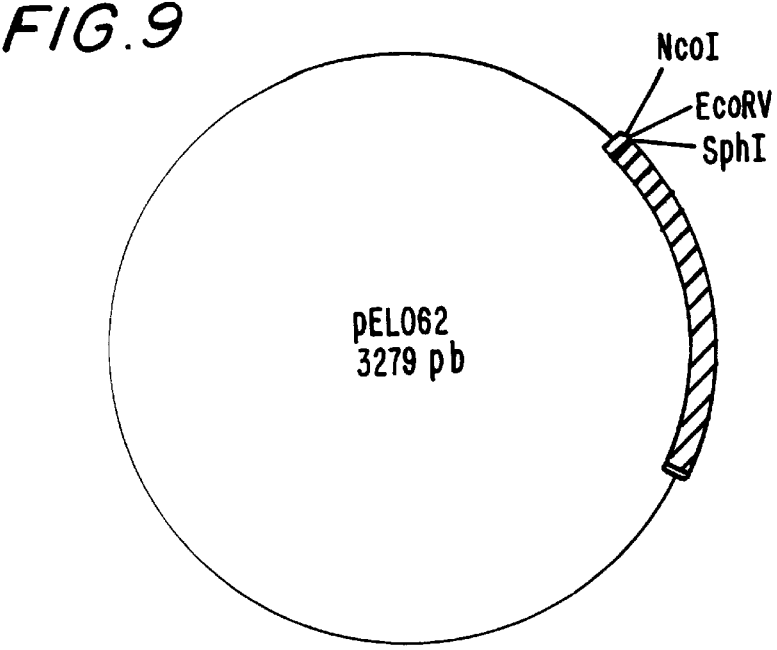
Figure 10:
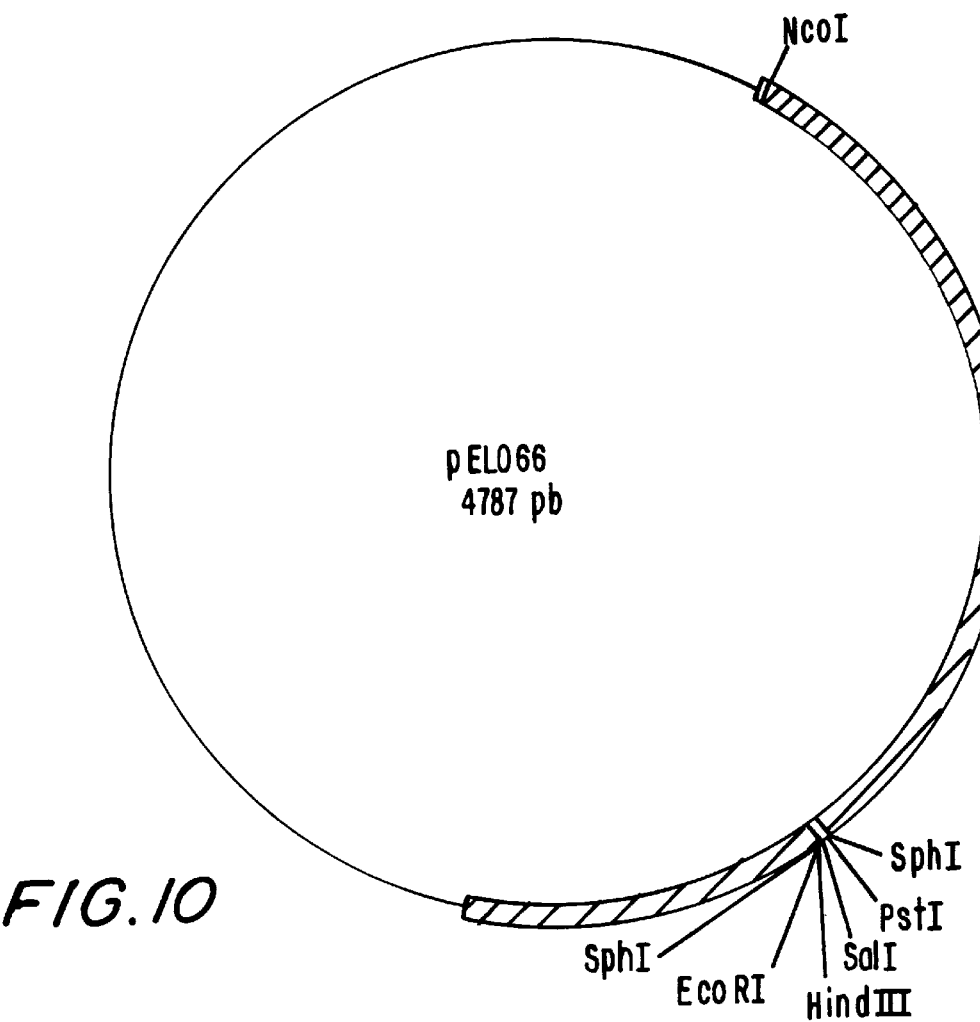

Plasmid pEL040 (see Example 5) was digested with NcoI and SphI to isolate the 1468-bp NcoI-SphI fragment. This fragment was ligated with the plasmid pUC BM20 (Boehringer Mannheim Cat# 1219235), previously digested with NcoI and SphI, to give the 4182-bp plasmid pEL054 (FIG. 7). Plasmid pEL040 was digested with EcoRI and SphI to isolate the 614-bp EcoRI-SphI fragment. This fragment was ligated with plasmid pUC BM20, previously digested with EcoRI and SphI, to give the 3263-bp plasmid pEL055 (FIG. 8). Plasmid pEL055 was digested with EcoRI, repaired with Klenow polymerase, ligated with itself, digested with HindIII, repaired with Klenow polymerase and lastly ligated with itself to give the 3279-bp plasmid pEL062 (FIG. 9). Plasmid pEL054 was digested with NcoI and SalI to isolate the 1492-bp NcoI-SalI fragment (fragment A). The following two oligonucleotides:
EL132 (SEQ ID No. 10) 5' CCGAATTCATATAAGCTTACGTG 3'
EL133 (SEQ ID No. 11) 5' TCGACACGTAACGTTATATGAATTCGGCATG 3'
were hybridized with one another to produce the 24-bp SalI-SphI fragment (fragment B). Fragments A and B were ligated together with plasmid pEL062, previously digested with NcoI and SphI, to give the 4787-bp plasmid pEL066 (FIG. 10). This plasmid contains an EcoRI-HindIII-SalI polylinker in intergenic region 3.

Example 8

Construction of the Donor Plasmid pEL090 and Isolation of vHVT16

The plasmid pEL004 (=plasmid pGH004 described in French Patent Application 92/13109), containing the IBDV VP2 gene in the form of a BamHI-HindIII cassette, was digested with BamHI and XbaI to isolate the 1104-bp BamHI-XbaI fragment (truncated VP2 gene). This fragment was cloned into the vector pBS-SK+, previously digested with XbaI and BamHI, to give the 4052-bp plasmid pEL022 (FIG. 11). The vector pBS-SK+ was digested with EcoRV and XbaI and then ligated with itself to give pBS-SK* (modified). Plasmid pEL004 was digested with KpnI and HindIII to isolate the 1387-bp KpnI-HindIII fragment containing the complete IBDV VP2 gene. This fragment was cloned into the vector pBS-SK*, previously digested with KpnI and HindIII, to give the 4292-bp plasmid pEL023 (FIG. 12). Plasmid pEL022 was digested with BamHI and NotI to isolate the 1122-bp BamHI-NotI fragment (fragment A). Plasmid pEL023 was digested with BamHI and NotI to isolate the 333-bp BamHI-NotI fragment (fragment B). Fragments A and B were ligated together with the vector pBS-SK+, previously digested with NotI and treated with alkaline phosphatase, to give the 4369-bp plasmid pEL024 (FIG. 13). Plasmid pEL024 was digested with NotI to isolate the 1445-bp NotI-NotI fragment. This fragment was ligated with the plasmid pCMVβ (Clontech Cat# 6177-1) (FIG. 14), previously digested with NotI, to give the 5095-bp plasmid pEL026 (FIG. 15). Plasmid pEL026 was digested with EcoRI, SalI and XmnI to isolate the 2428-bp EcoRI-SalI fragment. This fragment was ligated with plasmid pEL079 (see Example 5), previously digested with EcoRI and SalI, to give the 7514-bp plasmid pEL090 (FIG. 16). This plasmid permits the insertion of the HCMV-IE/IBDV VP2 expression cassette into intergenic site 1 of the HVT virus.

24-hour primary CEF cells were then transfected with the following mixture: 1 $\mu$g of linearized plasmid pEL090+5 $\mu$g of HVT viral DNA in 300 $\mu$l of OptiMEM medium (Gibco BRL Cat# 041-01985H) and 100 $\mu$g of LipofectAMINE diluted in 300 $\mu$l of medium (final volume of mixture=600 $\mu$l). These 600 $\mu$l were then diluted in 3 ml (final volume) of medium and plated out on $3\times10^6$ CEC I. The mixture was left in contact with the cells for 5 hours, then removed and replaced by 5 ml of culture medium. The cells were then left in culture for 3 days at +37° C., and were thereafter pronased, mixed with fresh CEC II (3:1 mixture) and plated out again on 1 96-well plate. This plate was left in culture for 3 days, and the cells were then pronased, mixed with fresh CEF II and plated out again on 2 96-well plates, one initial cup giving 2 sister cups. The 96-well plates were cultured until a cytopathic effect was seen. After 72 hours of culture, one of the two 96-well plates was fixed in 95% acetone for 30 minutes, and an indirect immuno-fluorescence (IIF) reaction was carried out with an anti-VP2 monoclonal antibody to test for plaques expressing the protein VP2. The "sister" cups of the cups displaying positive plaques in IIF were pronased, mixed with fresh CEF II and applied in limiting dilution to 96-well plates. After 3 days of culture, the cups displaying a cytopathic effect were pronased, mixed with CEF II and plated out again on 96-well plates, one initial cup giving 2 sister cups. 3 days later, the plaques expressing the protein VP2 were tested for again, as before, by IIF on one of the 2 sister plates.

Figure 37:
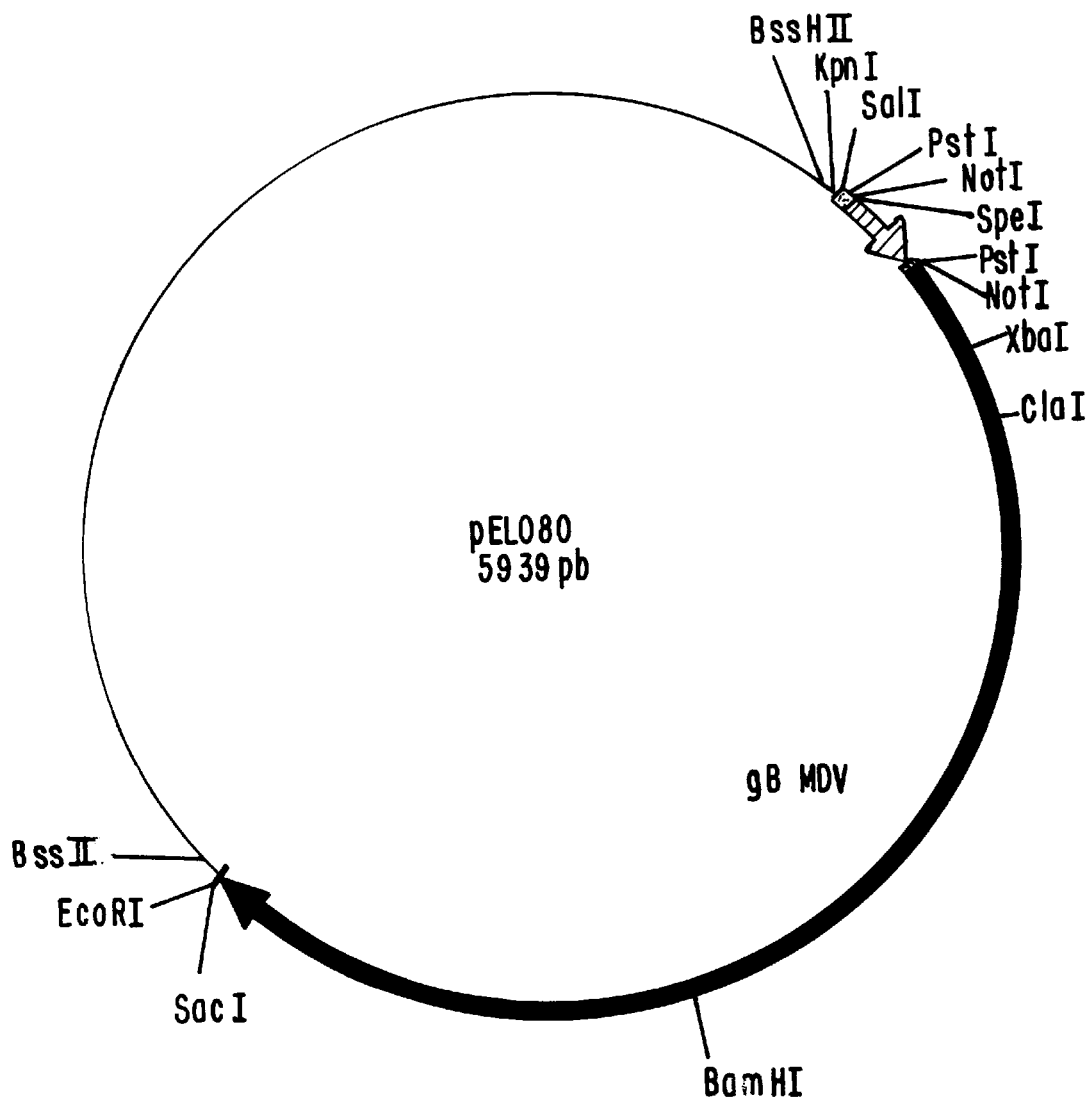
Figure 38:
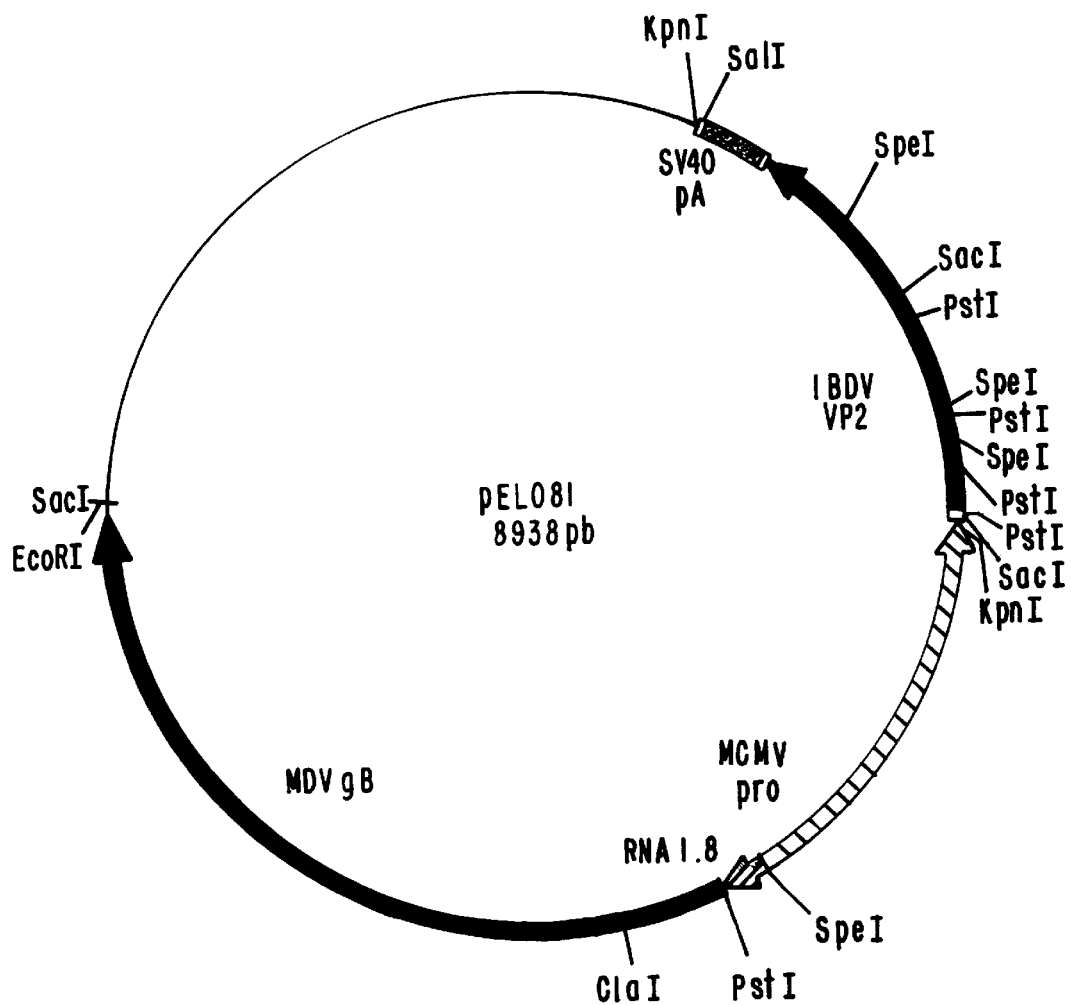

In general, 4 successive cycles of isolation (harvesting of a cup, plating out again, monitoring by IIF, subculturing of a sister cup, etc.) suffice for obtaining recombinant viruses the whole of whose progeny displays a specific fluorescence. One viral plaque which gave 100% of positive plaques in IIF with an anti-VP2 monoclonal antibody was designated vHVT16. The genomic DNA of this recombinant virus was characterized at molecular level by standard PCR and Southern blot techniques using the appropriate oligonucleotides and DNA probes.

Example 9

Construction of the Donor Plasmid pEL091 and Isolation of vHVT17

Plasmid pCMVβ (FIG. 14) was digested with SalI and SmaI to isolate the 3679-bp SalI-SmaI fragment containing the lacZ gene as well as the polyadenylation signal of the SV40 virus late gene. This fragment was inserted into the vector pBS-SK+, previously digested with SalI and EcoRV, to give the 6625-bp plasmid pCD002 (FIG. 17). This plasmid contains the lacZ reporter gene, but no promoter is located upstream of this gene. The viral genomic DNA of the MCMV virus was prepared as described in Example 2 and digested with PstI to isolate the 2285-bp PstI-PstI fragment. This fragment was cloned into the vector pBS-SK+, previously digested with PstI and treated with alkaline phosphatase, to give the plasmid pCD004. Plasmid pCD004 was digested with HpaI and PstI to isolate the 1389-bp HpaI-PstI fragment, which contains the promoter/activator region of the murine cytomegalovirus (MCMV) immediate early gene (Dorsch-Häsler K. et al. Proc. Natl. Acad. Sci. 1985. 82. 8325–8329, and Patent Application WO-A-87/03905). This fragment was cloned into plasmid pCD002. previously digested with PstI and SmaI, to give the 8007-bp plasmid pCD009 (FIG. 18).

A double-stranded oligonucleotide was obtained by hybridization of the following two oligonucleotides:

MB070 (SEQ ID No. 12) 5' CGAATTCACTAGTGTGT-GTCTGCAGGCGGCCGCGTGTGTGTCGACGGTAC 3'

MB071 (SEQ ID No. 13) 5' CGTCGACACACACGCGGC-CGCCTGCAGACACACACTAGTGAATTCGAGCT 3'

This double-stranded oligonucleotide was ligated in the vector pBS-SK+, previously digested with KpnI and SacI, to give the plasmid pEL067.

Plasmid pCD009 was digested with PstI and SpeI to isolate the 1396-bp PstI-SpeI fragment. This fragment was ligated with plasmid pEL067, previously digested with PstI and SpeI, to give the 4297-bp plasmid pEL068 (FIG. 19). Plasmid pEL026 (see Example 8) was digested with HindIII and SalI to isolate the 235-bp HindIII-SalI fragment (fragment B). Fragments A and B were ligated together with plasmid pEL068, previously digested with NotI and SalI, to give the 5908-bp plasmid pEL070 (FIG. 20). Plasmid pEL070 was digested with EcoRI, SalI and XmnI to isolate the 3035-bp EcoRI-SalI fragment. This fragment was ligated with plasmid pEL079 (see Example 5), previously digested with EcoRI and SalI, to give the 8109-bp plasmid pEL091 (FIG. 21). This plasmid permits the insertion of the MCMV-IE/IBDV VP2 expression cassette into intergenic site 1 of the HVT virus.

A cotransfection carried out as described in Example 8 with plasmid pEL091 and HVT virus genomic DNA led to the isolation and purification of the recombinant vHVT17.

Example 10

Construction of the Donor Plasmid pEL092 and Isolation of vHVT18

The 3.9-kbp EcoRI-SalI fragment of MDV virus strain RB1B genomic DNA containing the MDV gB gene (sequence published by Ross N. et al. J. Gen. Virol. 1989. 70. 1789–1804) was ligated with the vector pUC13, previously digested with EcoRI and SalI, to give the plasmid pCD007. This plasmid was digested with SacI and XhoI to isolate the 2260-bp SacI-XhoI fragment (central portion of the gB gene=fragment A). A PCR was carried out with the following oligonucleotides:

CD001 (SEQ ID No. 14) 5' GACTGGTACCGCGGCCG-CATGCACTTTTTAGGCGGAATTG 3'

CD002 (SEQ ID No. 15) 5' TTCGGGACATTTTCGCGG 3' and the template pCD007 to produce a 222-bp PCR fragment. This fragment was digested with KpnI and XbaI to isolate a 190-bp KpnI-XbaI fragment (5' end of the gB gene=fragment B). Another PCR was carried out with the following oligonucleotides:

CD003 (SEQ ID No. 16) 5' TATATGGCGTTAGTCTCC 3'

CD004 (SEQ ID No. 17) 5' TTGCGAGCTCGCGGCCGCT-TATTACACAGCATCATCTTCTG 3' and the template pCD007 to produce a 195-bp PCR fragment. This fragment was digested with SacI and SacII to isolate the 162-bp SacI-SacII fragment (3' end of the gB gene=fragment C). Fragments A, B and C were ligated together with the vector pBS-SK+, previously digested with KpnI and SacI, to give the 5485-bp plasmid pCD011 (FIG. 22). Plasmid pCD011 was digested with NotI to isolate the 2608-bp NotI-NotI fragment (whole MDV gB gene). This fragment was ligated with plasmid pCMVβ, previously digested with NotI and treated with alkaline phosphatase, to give the 6299-bp plasmid pCD020 (FIG. 23) (in this plasmid, the MDV gB gene replaces the lacZ gene). Plasmid pCD020 was digested with EcoRI and SalI to isolate the 3648-bp EcoRI-SalI fragment. This fragment was ligated with plasmid pEL079 (see Example 5) previously digested with EcoRI and SalI, to give the 8718-bp plasmid pEL092 (FIG. 24). This plasmid permits the insertion of the HCMV-IE/MDV gB expression cassette into intergenic site 1 of the HVT virus.

A cotransfection carried out as described in Example 8 with plasmid pEL092 and HVT virus genomic DNA led to the isolation and purification of the recombinant vHVT18.

Example 11

Construction of the Donor Plasmid pEL093 and Isolation of vHVT19

The building of a library of DNA complementary to the Newcastle disease virus (NDV), strain Texas, genome was carried out as described by Taylor J. et al. (J. Virol. 1990. 64. 1441–1450). A pBR322 clone containing the end of the fusion gene (F), the whole of the haemagglutinin-neuraminidase (HN) gene and the beginning of the gene for the polymerase was identified as pHN01. The sequence of the NDV HN gene present in this clone is presented in FIG. 25 (SEQ ID No. 18). Plasmid pHN01 was digested with SphI and XbaI to isolate the 2520-bp SphI-XbaI fragment. This fragment was ligated with the vector pUC19, previously digested with SphI and XbaI, to give the 5192-bp plasmid pHN02. Plasmid pHN02 was digested with ClaI and PstI to isolate the 700-bp ClaI-PstI fragment (fragment A). A PCR was carried out with the following oligonucleotides:

EL071 (SEQ ID No. 19) 5' CAGACCAAGCTTCTTAAATCCC 3'

EL073 (SEQ ID No. 20) 5' GTATTCGGGACAATGC 3' and the template pHN02 to produce a 270-bp PCR fragment. This fragment was digested with HindIII and PstI to isolate a 220-bp HindIII-PstI fragment (fragment B). Fragments A and B were ligated together with the vector pBS-SK+, previously digested with ClaI and HindIII, to give the 3872-bp plasmid pEL028 (FIG. 26). Plasmid pHN02 was digested with BsphI and ClaI to isolate the 425-bp BsphI-ClaI fragment (fragment C). A PCR was carried out with the following oligonucleotides:

EL074 (SEQ ID No. 21) 5' GTGACATCACTAGCGTCATCC 3'

EL074 (SEQ ID No. 22) 5' CCGCATCATCAGCGGCCGCGATCGGTCATGGACAGT 3' and the template pHN02 to produce a 425-bp PCR fragment. This fragment was digested with BsphI and NotI to isolate the 390-bp BsphI-NotI fragment (fragment D). Fragments C and D were ligated together with the vector pBS-SK+, previously digested with ClaI and NotI, to give 3727-bp plasmid pEL029bis (FIG. 27). Plasmid pEL028 was digested with ClaI and SacII to isolate the 960-bp ClaI-SacII fragment (fragment E). Plasmid pEL029bis was digested with ClaI and NotI to isolate the 820-bp ClaI-NotI fragment (fragment F). Fragments E and F were ligated together with the vector pBS-SK+, previously digested with NotI and SacII, to give the 4745-bp plasmid pEL030 (FIG. 28). Plasmid pEL030 was digested with NotI to isolate the 1780-bp NotI-NotI fragment (whole NDV HN gene). This fragment was ligated, in place of the lacZ gene, with plasmid pCMVβ, previously digested with NotI and treated with alkaline phosphatase, to give the 5471-bp plasmid pEL032 (FIG. 29). Plasmid pEL032 was digested with EcoRI and ClaI to isolate the 1636-bp EcoRI-ClaI fragment (fragment G). Plasmid pEL032 was digested with ClaI and SalI to isolate the 1182-bp ClaI-SalI fragment (fragment H). Fragments G and H were ligated together with plasmid pEL079 (see Example 5), previously digested with EcoRI and SalI, to give the 7890-bp plasmid pEL039 (FIG. 30). This plasmid permits the insertion of the HCMV-IE/NDV HN expression cassette into intergenic site 1 of the HVT virus.

A contransfection carried out as described in Example 8 with plasmid pEL093 and HVT virus genomic DNA led to the isolation and purification of the recombinant vHVT19.

Example 12

Construction of the Donor Plasmid pEL094 and Isolation of vHVT20

A clone originating from the library of DNA complementary to the Newcastle disease virus genome (see Example 11), and containing the whole of the fusion gene (F), was designated pNDV81. This plasmid has been described before, and the sequence of the NDV F gene present in this clone has been published (Taylor J. et al. J. Virol. 1990. 64. 1441–1450). Plasmid pNDV81 was digested with NarI and PstI to isolate the 1870-bp NarI-PstI fragment (fragment A). A PCR was carried out with the following oligonucleotides:

EL076 (SEQ ID No. 23) 5' TGACCCTGTCTGGGATGA 3'

EL077 (SEQ ID No. 24) 5' GGATCCCGGTCGACACATTGCGGCCGCAAGATGGGC 3' and the template pNDV81 to produce a 160-bp fragment. This fragment was digested with PstI and SalI to isolate the 130-bp PstI-SalI fragment (fragment B). Fragments A and B were ligated together with the vector pBS-SK+, previously digested with ClaI and SalI, to give the 4846-bp plasmid pEL033 (FIG. 31). Plasmid pEL033 was digested with NotI to isolate the 1935-bp NotI-NotI fragment (whole F gene). This fragment was ligated with plasmid pCMBβ, previously digested with NotI and treated with alkaline phosphatase, to give the 5624-bp plasmid pEL034 (the NDV F gene has replaced the lacZ gene) (FIG. 32). Plasmid pEL034 was digested with EcoRI and KpnI to isolate the 866-bp EcoRI-KpnI fragment (fragment C). Plasmid pEL034 was digested with KpnI and SalI to isolate the 2114-bp KpnI-SalI fragment (fragment D). Fragments C and D were ligated together with plasmid pEL079 (see Example 5), previously digested with EcoRI and SalI, to give the 8043-bp plasmid pEL094 (FIG. 33). This plasmid permits the insertion of the HCMV-IE/NDV F expression cassette into intergenic site 1 of the HVT virus.

A cotransfection carried out as described in Example 8 with plasmid pEL094 and HVT virus genomic DNA led to the isolation and purification of the recombinant vHVT20.

Example 13

Construction of the Donor Plasmid pEL095 and Isolation of vHVT21

The sequences located upstream of the MDV 1.8-kbp RNA gene are described in Bradley G. et al. (J. Virol. 1989. 63. 2534–2542) (FIG. 34 and SEQ ID No. 25). A PCR amplification was carried out on DNA extracted from lymphocytes harvested on chickens infected with MDV strain RB1B (see Example 1), with the following oligonucleotides:

MB047 (SEQ ID No. 26) 5' GGTCTACTAGTATTGGACTCTGGTGCGAACGC 3'

MB048 (SEQ ID No. 27) 5' GTCCAGAATTCGCGAAGAGAGAAGGAACCTC 3'

The 163-bp PCR fragment thereby obtained was digested with EcoRI and SpeI, and then ligated with plasmid pCD002 (see Example 9), previously digested with EcoRI and SpeI, to give the 6774-bp plasmid pBS002 (FIG. 35). Plasmid pBS002 contains the promoter of the MDV 1.8-kb RNA gene cloned upstream of the lacZ gene.

A PCR was carried out with the oligonucleotides:

MB047 (SEQ ID No. 26) and

MB072 (SEQ ID No. 28) 5' GTGTCCTGCAGTCGCGAAGAGAGAAGGAACCTC 3' and the template pBS002. The PCR fragment thereby obtained was digested with PstI and SpeI to isolate a 200-bp PstI-SpeI fragment. This fragment was ligated with plasmid pEL067 (see Example 9), previously digested with PstI and SpeI, to give the plasmid pEL069 (FIG. 36). Plasmid pCD007 (see Example 10) was digested with EcoRI and XbaI to isolate the 2670-bp EcoRI-XbaI fragment (fragment A). Plasmid pCD011 (see Example 10) was digested with NotI and XbaI to isolate the 180-bp NotI-KbaI fragment (fragment B). Plasmid pEL069 was digested with NotI and SpeI to isolate the 180-bp NotI-SpeI fragment (fragment C). Fragments A, B and C were ligated together with plasmid pEL067 (see Example 9), previously digested with EcoRI and SpeI, to give the 5939-bp plasmid pEL080 (FIG. 37). Plasmid pEL070 (see Example 9) was digested with KpnI and SpeI to isolate the 1345-bp KpnI-SpeI fragment (fragment D). Plasmid pEL070 was also digested with KpnI and SalI to isolate the 1658-bp KpnI-SalI fragment (fragment E). Fragments D and E were ligated together with plasmid pEL080, previously digested with SalI and SpeI, to give the 8938-bp plasmid pEL081 (FIG. 38). Plasmid pEL081 was digested with EcoRI and SalI to isolate the 6066-bp EcoRI-SalI fragment. This fragment was ligated with plasmid pEL079 (see Example 5), previously digested with EcoRI and SalI, to give finally the 11139-bp plasmid pEL095 (FIG. 39). This plasmid permits the insertion of the VP2/MCMV-IE//1.8-kbp RNA/MDV gB double expression cassette into intergenic site 1 of the HVT virus.

A cotransfection carried out as described in Example 8 with plasmid pEL095 and HVT virus genomic DNA led to the isolation and purification of the recombinant vHVT21.

Example 14

Construction of the Donor Plasmid pEL098 and Isolation of vHVT24

Figure 40:
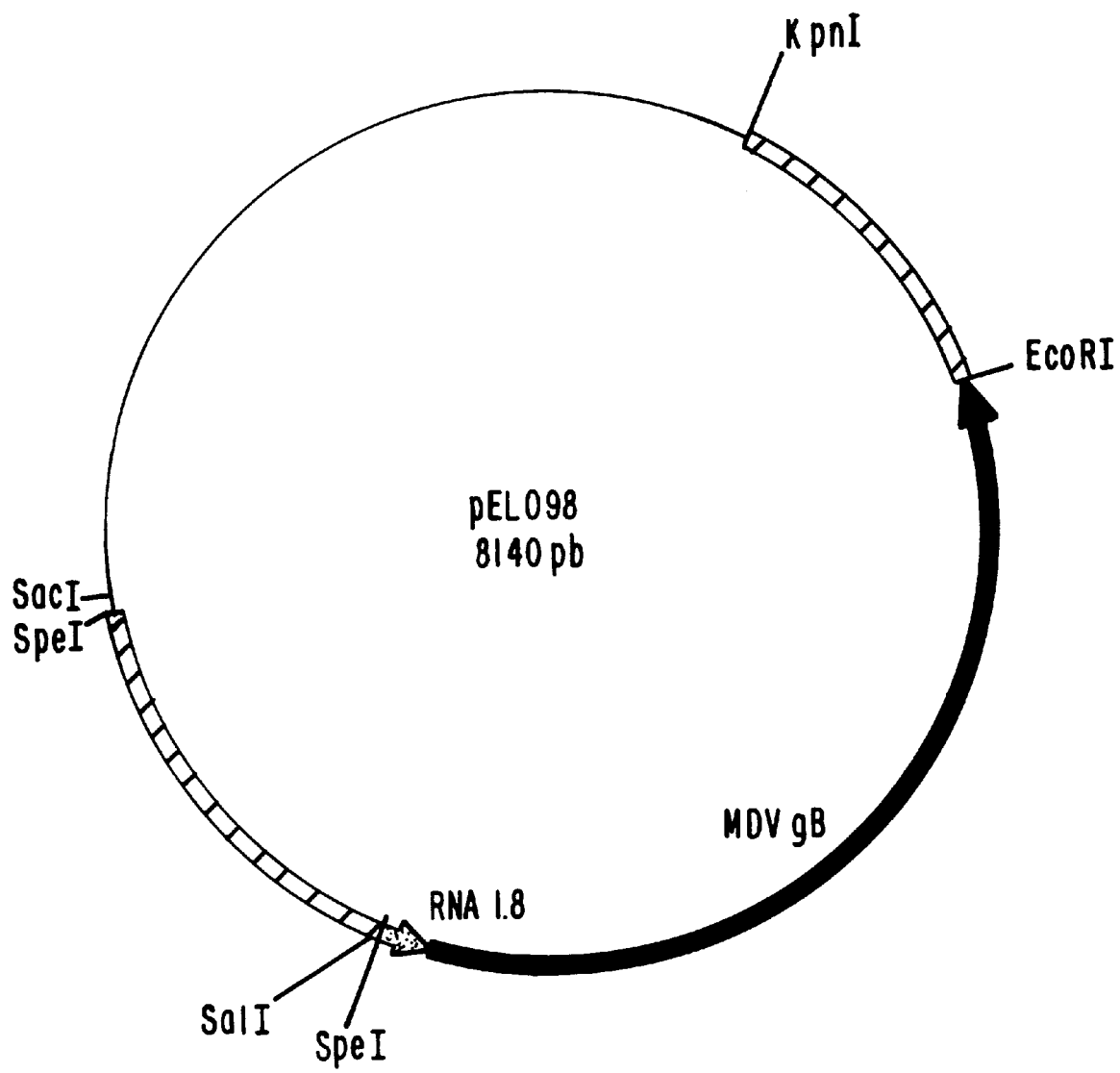

Plasmid pEL080 (see Example 13) was digested with EcoRI and SalI to isolate the 3040-bp EcoRI-SalI fragment (1.8-kbp RNA/MDV gB cassette). This fragment was ligated with plasmid pEL079 (see Example 5), previously digested with EcoRI and SalI, to give the 8140-bp plasmid pEL098 (FIG. 40). This plasmid permits the insertion of the 1.8-kbp RNA/MDV gB cassette into intergenic site 1 of the HVT virus.

A cotransfection carried out as described in Example 8 with plasmid pEL098 and HVT virus genomic DNA led to the isolation and purification of the recombinant vHVT24.

Example 15

Construction of Donor Plasmids For the Insertion of Cassettes For the Expression of IBV M and S Into Intergenic Site 1 of the HVT Virus According to the same strategy as that described above for the insertion of expression cassettes (genes placed under the control of the HCMV-IE or MCMV-IE promoters or MCMV-IE//1.8-kbp RNA double promoter) into intergenic site 1, it is possible to produce recombinant HVT viruses expressing at a high level the membrane (M) or spike (S) proteins of the avian infectious bronchitis virus (IBV). It is preferable to produce a construction in which the IBV S gene is under the control of the HCMV-IE promoter or the MCMV-IE promoter, or alternatively a construction in which the IBV M and IBV S genes are inserted together with the MCMV-IE/1.8-kbp RNA double promoter into intergenic site 1, the M gene being under the control of the 1.8-kbp RNA promoter and the S gene being under the control of the MCMV-IE promoter. In this arrangement, the 1.8-kbp RNA promoter is activated by the activator region of the MCMV-IE promoter.

Example 16

Construction of Recombinant HVT Viruses Comprising Foreign Genes Inserted Into Intergenic Sites 2 and 3

The obtaining of recombinant HVT viruses which have inserted cassettes for the expression of foreign genes into intergenic sites 2 and 3 is accomplished according to the strategy described for Examples 8 to 14, but using, respectively, plasmids pEL078 (intergenic site 2) and pEL066 (intergenic site 3) in place of plasmid pEL079 in Examples 8 to 14 in order to construct the specific donor plasmids.

Example 17

Preparation of a Vaccine According to the Invention

The preparation of the vaccines according to the invention may be accomplished by any standard technique known to a person skilled in the art, for example by culture in roller bottles. Roller bottles (175 cm$^2$), seeded with 200×10$^6$ primary chick embryo cells, are innoculated after 24 hours of incubation at 37° C. with 1 ml of a viral solution of recombinant HVT virus having a titre of 10$^5$ pfu/ml. After incubation for 4 days at 37° C., the supernatant is removed and the cells are detached with a trypsin/versene solution and thereafter harvested. The infected cells are then centrifuged. The supernatant is removed and the cells are taken up with 20 ml of a solution containing a lyophilization stabilizer (for example SPGA sucrose, phosphate, glutamate, albumin). This mixture is then sonicated, distributed in vials on the basis of 1 ml fractions and lastly lyophilized.

If necessary, the vaccine may also be distributed and frozen instead of lyophilized.

Example 18

An HVT recombinant virus obtained according to Examples 9 and 16 combined, and containing an MCMV-IE/VP2 expression cassette inserted into intergenic site 3, was used to immunize 1-day chicks intramuscularly. The chicks were then challenged at the age of 21 days with Gumboro disease virus. The results in respect of protection were evaluated 11 days after challenge by comparing the lesions of the bursa of Fabricius and the mortality between the vaccinated groups and the unvaccinated control group. The chicks vaccinated with this recombinant virus were 100% protected with respect to a Gumboro challenge, whereas no chick in the unvaccinated group was protected (observation of mortality or of lesions of the bursa of Fabricius in all the chicks in this group).

We claim:

1. A recombinant Herpesvirus of Turkeys (HVT) comprising at least one nucleotide sequence coding for and expressing an antigenic polypeptide inserted into one of intergenic regions 1, 2 and 3 or in ORF UL55 of the BamHI fragment I.

2. The recombinant HVT of claim 1 wherein the antigenic polypeptide is of an avian pathogenic agent.

3. The recombinant HVT of claim 2 wherein the nucleotide sequence is under the control of the CMV immediate early promoter or the 1.8 RNA promoter.

4. A recombinant avian vaccine comprising the recombinant HVT of claim 3.

5. The recombinant avian vaccine according to claim 4, wherein the CMV immediate early promoter is the human promoter HCMV IE or the murine promoter MCMV IE.

6. The recombinant avian vaccine according to claim 4, wherein the nucleotide sequence is inserted under the control of the CMV immediate early promoter and is a nucleotide sequence coding for an antigen of a pathogen chosen from the group consisting of Gumboro disease, Marek's disease, Newcastle disease, infectious bronchitis, infectious laryngotracheitis and avian anaemia.

7. The recombinant avian vaccine according to claim 4, wherein the nucleotide sequence inserted under the control of the CMV immediate early promoter is a nucleotide sequence coding for the polypeptide VP2 of the IBDV virus.

8. A recombinant avian vaccine according to claim 4, wherein the recombinant HVT comprises a first nucleotide sequence coding for and expressing an antigenic polypeptide of an avian pathogenic agent under the control of a first promoter comprising the CMV immediate early promoter and a second nucleotide sequence coding for and expressing an antigenic polypeptide of an avian pathogenic agent under the control of a second promoter wherein the first and second nucleotide sequences are inserted into one insertion region and the promoters are linked so that there is transcription in opposite directions.

9. The recombinant avian vaccine according to claim 8, wherein the second promoter is the Marek 1.8 RNA promoter.

10. The recombinant avian vaccine according to claim 8, wherein the first nucleotide sequence inserted under the control of the CMV immediate early promoter is a nucleotide sequence coding for the polypeptide VP2 of the IBDV virus, and the second nucleotide sequence inserted under the second control of the promoter is a nucleotide sequence coding for an antigen of another avian disease.

11. The recombinant avian vaccine according to claim 10, wherein the second nucleotide sequence coding for an antigen of another avian disease is an antigen of a pathogen chosen from the group consisting of Marek's disease, Newcastle disease, of infectious bronchitis, infectious laryngotracheitis and avian anaemia.

12. The recombinant avian vaccine according to claim 8, wherein the second promoter is a CMV immediate early promoter of different origin than the first promoter.

13. The recombinant avian vaccine according to claim 4, wherein the nucleotide sequence or sequences is/are chosen from the group consisting of sequences coding for the following genes:

VP2, VP3 and VP2+VP4+VP3 of the Gumboro disease virus, gB, gC, gD and gH+gL of the Marek's disease viruses, VP1 (52 kDa)+VP2 (24 kDa) of the avian anaemia virus, S and M of the infectious bronchitis virus, and gB, gC, gD and gH+gL of the infectious laryngotracheitis virus.

14. A recombinant avian vaccine according to claim 4, wherein the 1.8 RNA promoter is used.

15. A polyvalent vaccine comprising, as a mixture or to be mixed, a first recombinant Herpesvirus of Turkeys (HVT) comprising at least one first nucleotide sequence coding for and expressing an antigenic polypeptide of an avian pathogenic agent, inserted into one of intergenic regions 1, 2 and 3 or in ORF UL55 of the BamHI fragment I under the control of the CMV immediate early promoter or the 1.8 RNA promoter, and a second recombinant Herpesvirus of Turkeys (HVT) comprising at least one second nucleotide sequence coding for and expressing an antigenic polypeptide of an avian pathogenic agent, inserted into one of intergenic regions 1, 2 and 3 or in ORF UL55 of the BamHI fragment I under the control of the CMV immediate early promoter or the 1.8 RNA promoter, wherein the first nucleotide sequence and the second nucleotide sequence are comprised of different sequences.

16. A polyvalent vaccine according to claim 15, wherein the first nucleotide sequence and the second nucleotide sequence are from different pathogens.

17. The recombinant vaccine of any one of claims 4 to 7 or 13 wherein the nucleotide sequence is under the control of the CMV immediate early promoter.

18. The recombinant vaccine of any one of claims 4 to 7 or 13 wherein the nucleotide sequence is inserted into one of intergenic regions 1, 2 and 3 of the BamHI fragment.

19. The recombinant vaccine of any one of claims 4 to 7 or 13 wherein the nucleotide sequence is inserted into ORF UL55 of the BamHI fragment I.

20. The recombinant HVT of any one of claim 1 to 3 wherein the nucleotide sequence is inserted into one of intergenic regions 1, 2 and 3 of the BamHI fragment.

21. The recombinant HVT of any one of claim 1 to 3 wherein the nucleotide sequence is inserted into ORF UL55 of the BamHI fragment I.

22. The recombinant vaccine of any one of claims 8 to 12 wherein the one insertion region is one of intergenic regions 1, 2 and 3 of the BamHI fragment.

23. The recombinant vaccine of any one of claim 8 to 12 wherein the one insertion region is ORF UL55 of the BamHI fragment I.

24. The polyvalent vaccine of claim 15 or 16 wherein in each recombinant HVT, the nucleotide sequences are inserted into ORF UL55 of the BamHI fragment I.

25. The polyvalent vaccine of claim 15 or 16 wherein in each recombinant HVT, the nucleotide sequences are inserted into one of intergenic regions 1, 2 and 3 of the BamHI fragment.

26. The polyvalent vaccine of claim 15 or 16 wherein in each recombinant HVT, the nucleotide sequences are under the control of the CMV immediate early promoter.

27. The polyvalent vaccine of claim 15 or 16 wherein in each recombinant HVT, the nucleotide sequences are under the control of the 1.8 RNA promoter.

28. The recombinant HVT of claim 3 wherein the nucleotide sequence is under the control of the CMV immediate early promoter.

29. The recombinant HVT of claim 3 wherein the nucleotide sequence is under the control of the 1.8 RNA promoter.

* * * * *

UNITED STATES PATENT AND TRADEMARK OFFICE
CERTIFICATE OF CORRECTION

PATENT NO. : 5,980,906

DATED : NOVEMBER 9, 1999

INVENTOR(s) : AUDONNET ET AL.

It is certified that error appears in the above-identified patent and that said Letters Patent is hereby corrected as shown below:

ON THE COVER PAGE:

Under [73], change "Rhone Merieux" to --Merial--.

Under Attorney, Agent, or Firm, change "Fromer" to --Frommer--.

Signed and Sealed this

Third Day of April, 2001

*Attest:*

NICHOLAS P. GODICI

*Attesting Officer*     *Acting Director of the United States Patent and Trademark Office*